(12) United States Patent
Kwan et al.

(10) Patent No.: US 12,421,312 B2
(45) Date of Patent: Sep. 23, 2025

(54) ANTI-PD-L1 ANTIBODIES AND ANTIBODY-DRUG CONJUGATES

(71) Applicant: Seagen Inc., Bothell, WA (US)

(72) Inventors: Byron Hua Kwan, Bothell, WA (US); Heather Van Epps, Bothell, WA (US); Andrew Waight, Bothell, WA (US); Scott Jeffrey, Snohomish, WA (US); Ryan Lyski, Lynnwood, WA (US)

(73) Assignee: Seagen Inc., Bothell, WA (US)

( * ) Notice: Subject to any disclaimer, the term of this patent is extended or adjusted under 35 U.S.C. 154(b) by 1124 days.

(21) Appl. No.: 17/061,998

(22) Filed: Oct. 2, 2020

(65) Prior Publication Data

US 2021/0101982 A1 Apr. 8, 2021

Related U.S. Application Data

(60) Provisional application No. 62/910,988, filed on Oct. 4, 2019.

(51) Int. Cl.
*C07K 16/28* (2006.01)
*A61K 39/00* (2006.01)
*A61K 47/68* (2017.01)
*A61P 35/00* (2006.01)

(52) U.S. Cl.
CPC ...... *C07K 16/2827* (2013.01); *A61K 47/6801* (2017.08); *A61K 47/68031* (2023.08); *A61K 47/68037* (2023.08); *A61P 35/00* (2018.01); *A61K 2039/505* (2013.01)

(58) Field of Classification Search
CPC ............... C07K 16/2827; C07K 16/28; A61K 47/6801; A61K 2039/505; A61K 47/68037; A61P 35/00
See application file for complete search history.

(56) References Cited

U.S. PATENT DOCUMENTS

| | | |
|---|---|---|
| 4,474,893 A | 10/1984 | Reading |
| 4,714,681 A | 12/1987 | Reading |
| 4,880,935 A | 11/1989 | Thorpe |
| 4,925,648 A | 5/1990 | Hansen et al. |
| 5,122,368 A | 6/1992 | Greenfield et al. |
| 5,225,539 A | 7/1993 | Winter |
| 5,530,101 A | 6/1996 | Queen et al. |
| 5,573,920 A | 11/1996 | Randle |
| 5,585,089 A | 12/1996 | Queen et al. |
| 5,591,639 A | 1/1997 | Bebbington |
| 5,601,819 A | 2/1997 | Wong et al. |
| 5,622,929 A | 4/1997 | Willner et al. |
| 5,624,821 A | 4/1997 | Winter et al. |
| 5,658,759 A | 8/1997 | Bebbington |
| 5,824,805 A | 10/1998 | King et al. |
| 5,834,597 A | 11/1998 | Tso et al. |
| 5,859,205 A | 1/1999 | Adair et al. |
| 5,879,936 A | 3/1999 | Bebbington et al. |
| 5,891,693 A | 4/1999 | Bebbington et al. |
| 5,981,216 A | 11/1999 | Kenten et al. |
| 6,130,237 A | 10/2000 | Denny et al. |
| 6,214,345 B1 | 4/2001 | Firestone et al. |
| 6,407,213 B1 | 6/2002 | Carter et al. |
| 6,624,821 B1 | 9/2003 | Shin et al. |
| 6,881,557 B2 | 4/2005 | Foote |
| 7,498,298 B2 | 3/2009 | Doronina et al. |
| 7,659,241 B2 | 2/2010 | Senter et al. |
| 7,968,687 B2 | 6/2011 | McDonagh et al. |
| 2005/0238649 A1 | 10/2005 | Doronina et al. |
| 2006/0074008 A1 | 4/2006 | Senter et al. |
| 2009/0018086 A1 | 1/2009 | Doronina et al. |
| 2009/0111756 A1 | 4/2009 | Doronina et al. |
| 2010/0158909 A1 | 6/2010 | McDonagh et al. |
| 2018/0092984 A1 | 4/2018 | Lewis et al. |
| 2018/0154018 A1* | 6/2018 | Yurkovetskiy ......... A61K 47/65 |
| 2019/0343828 A1* | 11/2019 | Jeffrey ................... A61P 35/02 |

FOREIGN PATENT DOCUMENTS

| | | |
|---|---|---|
| EP | 0216846 | 4/1987 |
| EP | 0323997 | 7/1989 |
| EP | 0338841 | 10/1989 |
| EP | 0629240 | 12/1994 |
| WO | WO 1987/04462 | 7/1987 |
| WO | WO 1989/12624 | 12/1989 |
| WO | WO 1991/00360 | 1/1991 |
| WO | WO 1992/05793 | 4/1992 |
| WO | WO 1992/08802 | 5/1992 |
| WO | WO 1992/22653 | 12/1992 |
| WO | WO 1993/17715 | 9/1993 |
| WO | WO 2006/036291 | 4/2006 |
| WO | WO 2018/191660 | 10/2018 |
| WO | WO 2019/148089 | 8/2019 |

(Continued)

OTHER PUBLICATIONS

Michael J. Birrer, Kathleen N. Moore, Ilaria Betella, Richard C. Bate. "Antibody-Drug Conjugate-Based Therapeutics: State of the Science" JNCI J Natl Cancer Inst, Mar. 11, 2019 111(6): djz035.doi: 10.1093/jnci/djz035 (Year: 2019).*
Anastasia Constantinidou, Constantinos Alifieris, Dimitrios T. Trafalis, "Targeting Programmed Cell Death -1 (PD-1) and Ligand (PD-L1): A new era in cancer active immunotherapy", Pharmacology & Therapeutics, vol. 194, Feb. 2019, pp. 84-106, ISSN 0163-7258, https://doi.org/10.1016/j.pharmther (Year: 2019).*
Liu, Boning et al. "Acid-induced aggregation propensity of nivolumab is dependent on the Fc." mAbs vol. 8,6 (2016): 1107-17. doi: 10.1080/19420862.2016.1197443 (Year: 2016).*
Kevin O. Saunders "Conceptual Approaches to Modulating Antibody Effector Functions and Circulation Half-Life" Front. Immunol., Jun. 6, 2019, vol. 10—2019. doi: 10.3389/fimmu.2019.01296 (Year: 2019).*

(Continued)

*Primary Examiner* — Peter J Reddig
(74) *Attorney, Agent, or Firm* — Stephen E. Moyer

(57) ABSTRACT

Provided are novel anti-PD-L1 antibodies and antibody-drug conjugates and methods of using such anti-PD-L1 antibodies and antibody-drug conjugates to treat cancer.

51 Claims, 31 Drawing Sheets

Specification includes a Sequence Listing.

(56) References Cited

FOREIGN PATENT DOCUMENTS

| WO | WO 2019/195665 | 10/2019 | |
|---|---|---|---|
| WO | WO-2019195665 A1 | * 10/2019 | ......... A61K 31/4745 |

OTHER PUBLICATIONS

Powels et al. (Nature Nov. 27, 2014, 515:558-562) (Year: 2014).*
Al-Lazikani et al., "Standard conformations for the canonical structures of immunoglobulins," JMB, 273(4):927-948, Nov. 1997.
Chari et al., "Immunoconjugates containing novel maytansinoids: promising anticancer drugs," Cancer Res., 52(1):127-31, Jan. 1992.
Chothia et al., "Canonical structures for the hypervariable regions of immunoglobulins," J Mol. Biol., 196(4):901-917, Aug. 1987.
Clackson et al., "Making antibody fragments using phage display libraries," Nature, 352(6336):624-628. Aug. 1991.
Collins et al., "Product review: avelumab, an anti-PD-L1 antibody," Hum Vaccin Immunother., 15(4):891-908, 2019.
Davies et al., "Expression of GnTIII in a recombinant anti-CD20 CHO production cell line: Expression of antibodies with altered glycoforms leads to an increase in ADCC through higher affinity for FC gamma RIII," Biotech. Bioeng., 74(4):288-94, Aug. 2001.
De La Cruz Edmunds et al., "Development of transfection and high-producer screening protocols for the CHOK1SV cell system," Molecular Biotechnology, 34(2):179-190, Oct. 2006.
Dubowchik et al., "Receptor-mediated and enzyme-dependent targeting of cytotoxic anticancer drugs," Pharm, Therapeutics, 83(2):67-123, Aug. 1999.
Ghetie et al., "Multiple roles for the major histocompatibility complex class I-related receptor FcRn," Ann. Rev. Immunol., 18:739-766, 2000.
Ghetie et al., "Transcytosis and catabolismof antibody," Immunol. Res., 25(2):97-113, 2002.
Hieter et al., "Evolution of human immunoglobulin kappa J region genes," J. Biol. Chem., 257(3):1516-1522, Feb. 1982.
Hinton et al., "Engineered human IgG antibodies with longer serum half-lives in primates," J. Biol. Chem., Feb. 2004, 279(8):6213-6.
Honegger et al., "Yet another numbering scheme for immunoglobulin variable domains: an automatic modeling and analysis tool," J Mol Biol, 309(3):657-70, Jun. 2001.
Idusogie et al., "Engineered antibodies with increased activity to recruit complement," J. Immunol., 166(4):2571-75, Feb. 2001.
Iwahashi et al., "CDR substitutions of a humanized monoclonal antibody (CC49): contributions of individual CDRs to antigen binding and immunogenicity," Mol. Immunol., 36(15-16):1079-1091, 1999.
Jefferis et al., "Human immunoglobulin allotypes: possible implications for immunogenicity," MAbs, 1(4):332-8, 2009.
Johnson et al., "Anti-tumor activity of CC49-doxorubicin immunoconjugates," Anticancer Res., 15(4):1387-93, 1995, Abstract.
Kohler et al., "Continuous cultures of fused cells secreting antibody of predefined specificity," Nature, 256(5517):495-7, Aug. 1975.
Kontermann et al., "Complement recruitment using bispecific diabodies," Nat. Biotech., 15(7):629-31, Jul. 1997.
Kostelny et al., "Formation of a bispecific antibody by the use of leucine zippers," J. Immunol., 148(5):1547-1553, Mar. 1992, Abstract.
Lau et al., "Conjugation of doxorubicin to monoclonal anti-carcinoembryonic antigen antibody via novel thiol-directed cross-linking reagents," Bioorg Med Chem., 3(10):1299-1304, Oct. 1995.
Lau et al., "Novel doxorubicin-monoclonal anti-carcinoembryonic antigen antibody immunoconjugate activity in vitro," Bioorg Med Chem., 3(10):1305-12, Oct. 1995.
Lazar et al., "Engineered antibody Fc variants with enhanced effector function," Proc. Natl. Acad. Sci. USA, 103(11):4005-10, Mar. 2006.
Lefranc et al., "IMGT unique numbering for immunoglobulin and T cell receptor variable domains and Ig superfamily V-like domains," Dev Comp Immunol, 27(1):55-77, Jan. 2003.
Lund et al., "Multiple interactions of IgG with its core oligosaccharide can modulate recognition by complement and human Fc gamma receptor I and influence the synthesis of its oligosaccharide chains," J. Immunol., 157(11):4963-69, Dec. 1996, Abstract.
MacCallum et al., "Antibody-antigen interactions: contact analysis and binding site topography," J. Mol. Biol., 262(5):732-745, Oct. 1996.
Marks et al., "By-passing immunization. Human antibodies from V-gene libraries displayed on page," J Mol Biol., 222(3):581-597, Dec. 1991.
Martin et al., "Modeling antibody hypervariable loops: a combined algorithm," PNAS, 86(23):9268-9272, Dec. 1989.
Mattila et al., "Extensive allelic sequence variation in the J region of the human immunoglobulin heavy chain gene locus," Eur. J. Immunol., 25(9):2578-2582, Sep. 1995.
Nakada et al., "Novel antibody drug conjugates containing exatecan derivative-based cytotoxic payloads," Bioorg Med Chem Lett., 26(6):1542-1545, Mar. 2016.
Neville et al., "Enhancement of immunotoxin efficacy by acid-cleavable cross-linking agents utilizing diphtheria toxin and toxin mutants," Biol. Chem., 264(25):14653-14661, Sep. 1989.
Niwa et al., "Defucosylated chimeric anti-CC chemokine receptor 4 IgG1 with enhanced antibody-dependent cellular cytotoxicity shows potent therapeutic activity to T-cell leukemia and lymphoma," Cancer Res., 64(6):2127-33, Mar. 2004.
Okazaki et al., "Fucose depletion from human IgG1 oligosaccharide enhances binding enthalpy and association rate between IgG1 and FcgammaRIIIa," J. Mol. Biol., 336(5):1239-49, Mar. 2004.
Pascalis et al., "Grafting of "abbreviated" complementarity-determining regions containing specificity-determining residues essential for ligand contact to engineer a less immunogenic humanized monoclonal antibody," J. Immunol., 169(6):3076-84, Sep. 2002.
PCT International Search Report and Written Opinion in International Appln. No. PCT/US2020/054037, dated Feb. 10, 2021, 27 pages.
PCT Invitation to Pay Additional Fees in International Appln. No. PCT/US2020/054037, dated Feb. 22, 2021, 22 pages.
Queen et al., "Cell-type specific regulation of a kappa immunoglobulin gene by promoter and enhancer elements," Immunol. Rev., 89:49-68, Feb. 1986.
Rudikoff et al., "Single amino acid substitution altering antigen-binding specificity," Proc Natl Acad Sci USA, 79(6):1979-83, Mar. 1982.
Sau et al., "PDL-1 Antibody Drug Conjugate for Selective Chemo-Guided Immune Modulation of Cancer," Cancers (Basel), 11(2):232, 12 pages, Feb. 2019.
Sela-Culang et al., "The structural basis of antibody-antigen recognition," Front Immunol., 4:302, 14 pages, Oct. 2013.
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276(9):6591-604, Mar. 2001.
Shields et al., "Lack of fucose on human IgG1 N-linked oligosaccharide improves binding to human Fcgamma RIII and antibody-dependent cellular toxicity," J. Biol. Chem., 277(3):26733-40, Jul. 2002.
Shin et al., "Physical map of the 3' region of the human immunoglobulin heavy chain locus: clustering of autoantibody-related variable segments in one haplotype," EMBO J., 10(12):3641-3645, Dec. 1991.
Shopes, "A genetically engineered human IgG mutant with enhanced cytolytic activity," J. Immunol., 148(9):2918-22, May 1992, Abstract.
Smith et al., "Addition of a mu-tailpiece to IgG results in polymeric antibodies with enhanced effector functions including complement-mediated cytolysis by IgG4," J. Immunol., 154(5):2226-36, Mar. 1995. Abstract.
Storz, "Intellectual property issues of immune checkpoint inhibitors," MAbs, 8(1):10-26, 2016.
Tamura et al., "Structural correlates of an anticarcinoma antibody: identification of specificity-determining residues (SDRs) and development of a minimally immunogenic antibody variant by retention of SDRs only," Journal of Immunology, 164(3):1432-1441, Feb. 2000.

(56) References Cited

OTHER PUBLICATIONS

Tan et al., "Distinct PD-L1 binding characteristics of therapeutic monoclonal antibody durvalumab," *Protein Cell*, 9(1):135-139, Jan. 2018.

Thorpe et al., "New coupling agents for the synthesis of immunotoxins containing a hindered disulfide bond with improved stability in vivo," *Cancer Res.*, 47(22):5924-5931, Nov. 1987.

Thorpe et al., "The preparation and cytotoxic properties of antibody-toxin conjugates," *Immunol. Rev.*, 62:119-58, 1982.

Tutt et al., "Trispecific F(ab')3 derivatives that use cooperative signaling via the TCR/CD3 complex and CD2 to activate and redirect resting cytotoxic T cells," *J. Immunol.*, 147(1):60-69, Jul. 1991, Abstract.

Umana et al., "Engineered glycoforms of an antineuroblastoma IgG1 with optimized antibody-dependent cellular cytotoxic activity," *Nat. Biotechnol.*, 17(2):176-180, Feb. 1999.

UniProt Accession No. Q9NZQ7.1, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Sep. 12, 2018, 8 pages.

Vajdos et al., "Comprehensive functional maps of the antigen-binding site of an anti-ErbB2 antibody obtained with shotgun scanning mutagenesis," *Journal of Molecular Biology*, 320(2):415-428, Jul. 2002.

Wright et al., "Effect of glycosylation on antibody function: implications for genetic engineering," *Trends Biotechnol.*, 15(1):26-31, Jan. 1997.

Rudnick, S. I. et al., "Influence of Affinity and Antigen Internalization on the Uptake and Penetration of Anti-HER2 Antibodies in Solid Tumors", Cancer research, vol. 71, No. 6, Mar. 15, 2011, pp. 2250-2259.

* cited by examiner

- SG-559-01 MP-PEG8-VKG-Camptothecin ADC
- Isotype Control MP-PEG8-VKG-Camptothecin ADC
- SG-559-01 LALA MP-PEG8-VKG-Camptothecin ADC
- Isotype Control LALA MP-PEG8-VKG-Camptothecin ADC
- SG-559-01 LALA antibody

SEQUENCE LISTING

<160> NUMBER OF SEQ ID NOS: 87

<210> SEQ ID NO 1
<211> LENGTH: 123
<212> TYPE: PRT
<213> ORGANISM: Artificial
<220> FEATURE:
<223> OTHER INFORMATION: Ab1 heavy chain variable region

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val

```
                  100                 105                 110
Trp Gly Gln Gly Thr Thr Val Thr Val Ser Ser
            115                 120

<210> SEQ ID NO 2
<211> LENGTH: 106
<212> TYPE: PRT
<213> ORGANISM: Artificial
<220> FEATURE:
<223> OTHER INFORMATION: Ab1 light chain variable region

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 3
<211> LENGTH: 5
<212> TYPE: PRT
<213> ORGANISM: Artificial
<220> FEATURE:
<223> OTHER INFORMATION: Ab1 heavy chain CDR1

<400> SEQUENCE: 3

Thr Tyr Ala Ile Ser
1               5

<210> SEQ ID NO 4
<211> LENGTH: 17
<212> TYPE: PRT
<213> ORGANISM: Artificial
<220> FEATURE:
<223> OTHER INFORMATION: Ab1 heavy chain CDR2

<400> SEQUENCE: 4

Gly Ile Ile Pro Ile Phe Gly Lys Ala His Tyr Ala Gln Lys Phe Gln
1               5                   10                  15

Gly

<210> SEQ ID NO 5
<211> LENGTH: 14
<212> TYPE: PRT
<213> ORGANISM: Artificial
<220> FEATURE:
<223> OTHER INFORMATION: Ab1 heavy chain CDR3

<400> SEQUENCE: 5

Lys Phe His Phe Val Ser Gly Ser Pro Phe Gly Met Asp Val
1               5                   10

<210> SEQ ID NO 6
```

```
<211> LENGTH: 11
<212> TYPE: PRT
<213> ORGANISM: Artificial
<220> FEATURE:
<223> OTHER INFORMATION: Ab1 light chain CDR1

<400> SEQUENCE: 6

Arg Ala Ser Gln Ser Val Ser Ser Tyr Leu Ala
1               5                   10

<210> SEQ ID NO 7
<211> LENGTH: 7
<212> TYPE: PRT
<213> ORGANISM: Artificial
<220> FEATURE:
<223> OTHER INFORMATION: Ab1 light chain CDR2

<400> SEQUENCE: 7

Asp Ala Ser Asn Arg Ala Thr
1               5

<210> SEQ ID NO 8
<211> LENGTH: 8
<212> TYPE: PRT
<213> ORGANISM: Artificial
<220> FEATURE:
<223> OTHER INFORMATION: Ab1 light chain CDR3

<400> SEQUENCE: 8

Gln Gln Arg Ser Asn Trp Pro Thr
1               5

<210> SEQ ID NO 9
<211> LENGTH: 453
<212> TYPE: PRT
<213> ORGANISM: Artificial
<220> FEATURE:
<223> OTHER INFORMATION: SG-559-01 LALA hIgG1 heavy chain

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Ala
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Lys Ala His Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
                100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 10
<211> LENGTH: 213
<212> TYPE: PRT
<213> ORGANISM: Artificial
<220> FEATURE:
<223> OTHER INFORMATION: SG-559-01 kappa light chain

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Arg Ser Asn Trp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 11
<211> LENGTH: 123
<212> TYPE: PRT
<213> ORGANISM: Artificial
<220> FEATURE:
<223> OTHER INFORMATION: SG-559-01 heavy chain variable region

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Ala
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 12
<211> LENGTH: 106
<212> TYPE: PRT
<213> ORGANISM: Artificial
<220> FEATURE:
<223> OTHER INFORMATION: SG-559-01 light chain variable region

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile

```
                35                  40                  45
Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                 85                  90                  95

Phe Gly Gln Gly Thr Lys Val Glu Ile Lys
            100                 105

<210> SEQ ID NO 13
<211> LENGTH: 5
<212> TYPE: PRT
<213> ORGANISM: Artificial
<220> FEATURE:
<223> OTHER INFORMATION: SG-559-01 heavy chain CDR1

<400> SEQUENCE: 13

Thr Ala Ala Ile Ser
 1               5

<210> SEQ ID NO 14
<211> LENGTH: 17
<212> TYPE: PRT
<213> ORGANISM: Artificial
<220> FEATURE:
<223> OTHER INFORMATION: SG-559-01 heavy chain CDR2

<400> SEQUENCE: 14

Gly Ile Ile Pro Ile Phe Gly Lys Ala His Tyr Ala Gln Lys Phe Gln
 1               5                  10                  15

Gly

<210> SEQ ID NO 15
<211> LENGTH: 14
<212> TYPE: PRT
<213> ORGANISM: Artificial
<220> FEATURE:
<223> OTHER INFORMATION: SG-559-01 heavy chain CDR3

<400> SEQUENCE: 15

Lys Phe His Phe Val Ser Gly Ser Pro Phe Gly Met Asp Val
 1               5                  10

<210> SEQ ID NO 16
<211> LENGTH: 11
<212> TYPE: PRT
<213> ORGANISM: Artificial
<220> FEATURE:
<223> OTHER INFORMATION: SG-559-01 light chain CDR1

<400> SEQUENCE: 16

Arg Ala Ser Gln Ser Val Ser Ser Tyr Leu Ala
 1               5                  10

<210> SEQ ID NO 17
<211> LENGTH: 7
<212> TYPE: PRT
<213> ORGANISM: Artificial
<220> FEATURE:
<223> OTHER INFORMATION: SG-559-01 light chain CDR2

<400> SEQUENCE: 17

Asp Ala Ser Asn Arg Ala Thr
```

```
<210> SEQ ID NO 18
<211> LENGTH: 8
<212> TYPE: PRT
<213> ORGANISM: Artificial
<220> FEATURE:
<223> OTHER INFORMATION: SG-559-01 light chain CDR3

<400> SEQUENCE: 18

Gln Gln Arg Ser Asn Trp Pro Thr
1               5

<210> SEQ ID NO 19
<211> LENGTH: 453
<212> TYPE: PRT
<213> ORGANISM: Artificial
<220> FEATURE:
<223> OTHER INFORMATION: SG-559-02 LALA hIgG1 heavy chain

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

```
Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 20
<211> LENGTH: 213
<212> TYPE: PRT
<213> ORGANISM: Artificial
<220> FEATURE:
<223> OTHER INFORMATION: SG-559-02 kappa light chain

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ala
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

Cys Glu Val Thr His Gln Gly Leu Ser Ser Pro Val Thr Lys Ser Phe
            195                 200                 205

Asn Arg Gly Glu Cys
    210

<210> SEQ ID NO 21
<211> LENGTH: 123
<212> TYPE: PRT
<213> ORGANISM: Artificial
<220> FEATURE:
<223> OTHER INFORMATION: SG-559-02 heavy chain variable region

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 22
<211> LENGTH: 106
<212> TYPE: PRT
<213> ORGANISM: Artificial
<220> FEATURE:
<223> OTHER INFORMATION: SG-559-02 light chain variable region

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ala
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 23
<211> LENGTH: 5
<212> TYPE: PRT
<213> ORGANISM: Artificial
<220> FEATURE:
<223> OTHER INFORMATION: SG-559-02 heavy chain CDR1

```
<400> SEQUENCE: 23

Thr Tyr Ala Ile Ser
1               5

<210> SEQ ID NO 24
<211> LENGTH: 17
<212> TYPE: PRT
<213> ORGANISM: Artificial
<220> FEATURE:
<223> OTHER INFORMATION: SG-559-02 heavy chain CDR2

<400> SEQUENCE: 24

Gly Ile Ile Pro Ile Phe Gly Lys Ala His Tyr Ala Gln Lys Phe Gln
1               5                   10                  15

Gly

<210> SEQ ID NO 25
<211> LENGTH: 14
<212> TYPE: PRT
<213> ORGANISM: Artificial
<220> FEATURE:
<223> OTHER INFORMATION: SG-559-02 heavy chain CDR3

<400> SEQUENCE: 25

Lys Phe His Phe Val Ser Gly Ser Pro Phe Gly Met Asp Val
1               5                   10

<210> SEQ ID NO 26
<211> LENGTH: 11
<212> TYPE: PRT
<213> ORGANISM: Artificial
<220> FEATURE:
<223> OTHER INFORMATION: SG-559-02 light chain CDR1

<400> SEQUENCE: 26

Arg Ala Ser Gln Ser Val Ser Ser Ala Leu Ala
1               5                   10

<210> SEQ ID NO 27
<211> LENGTH: 7
<212> TYPE: PRT
<213> ORGANISM: Artificial
<220> FEATURE:
<223> OTHER INFORMATION: SG-559-02 light chain CDR2

<400> SEQUENCE: 27

Asp Ala Ser Asn Arg Ala Thr
1               5

<210> SEQ ID NO 28
<211> LENGTH: 8
<212> TYPE: PRT
<213> ORGANISM: Artificial
<220> FEATURE:
<223> OTHER INFORMATION: SG-559-02 light chain CDR3

<400> SEQUENCE: 28

Gln Gln Arg Ser Asn Trp Pro Thr
1               5

<210> SEQ ID NO 29
<211> LENGTH: 453
<212> TYPE: PRT
<213> ORGANISM: Artificial
<220> FEATURE:
<223> OTHER INFORMATION: SG-559-03 LALA hIgG1 heavy chain
```

<400> SEQUENCE: 29

```
Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
```

```
                    405                 410                 415
Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 30
<211> LENGTH: 213
<212> TYPE: PRT
<213> ORGANISM: Artificial
<220> FEATURE:
<223> OTHER INFORMATION: SG-559-03 kappa light chain

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Leu Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 31
<211> LENGTH: 123
<212> TYPE: PRT
<213> ORGANISM: Artificial
<220> FEATURE:
<223> OTHER INFORMATION: SG-559-03 heavy chain variable region

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30
```

```
Ala Ile Ser Trp Val Arg Gln Ala Pro Gly Gln Gly Leu Glu Trp Met
            35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120
```

<210> SEQ ID NO 32
<211> LENGTH: 106
<212> TYPE: PRT
<213> ORGANISM: Artificial
<220> FEATURE:
<223> OTHER INFORMATION: SG-559-03 light chain variable region

<400> SEQUENCE: 32

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Leu Pro Thr
                85                  90                  95

Phe Gly Gln Gly Thr Lys Val Glu Ile Lys
            100                 105
```

<210> SEQ ID NO 33
<211> LENGTH: 5
<212> TYPE: PRT
<213> ORGANISM: Artificial
<220> FEATURE:
<223> OTHER INFORMATION: SG-559-03 heavy chain CDR1

<400> SEQUENCE: 33

```
Thr Tyr Ala Ile Ser
1               5
```

<210> SEQ ID NO 34
<211> LENGTH: 17
<212> TYPE: PRT
<213> ORGANISM: Artificial
<220> FEATURE:
<223> OTHER INFORMATION: SG-559-03 heavy chain CDR2

<400> SEQUENCE: 34

```
Gly Ile Ile Pro Ile Phe Gly Lys Ala His Tyr Ala Gln Lys Phe Gln
1               5                   10                  15

Gly
```

<210> SEQ ID NO 35

```
<211> LENGTH: 14
<212> TYPE: PRT
<213> ORGANISM: Artificial
<220> FEATURE:
<223> OTHER INFORMATION: SG-559-03 heavy chain CDR3

<400> SEQUENCE: 35

Lys Phe His Phe Val Ser Gly Ser Pro Phe Gly Met Asp Val
1               5                   10

<210> SEQ ID NO 36
<211> LENGTH: 11
<212> TYPE: PRT
<213> ORGANISM: Artificial
<220> FEATURE:
<223> OTHER INFORMATION: SG-559-03 light chain CDR1

<400> SEQUENCE: 36

Arg Ala Ser Gln Ser Val Ser Ser Tyr Leu Ala
1               5                   10

<210> SEQ ID NO 37
<211> LENGTH: 7
<212> TYPE: PRT
<213> ORGANISM: Artificial
<220> FEATURE:
<223> OTHER INFORMATION: SG-559-03 light chain CDR2

<400> SEQUENCE: 37

Asp Ala Ser Asn Arg Ala Thr
1               5

<210> SEQ ID NO 38
<211> LENGTH: 8
<212> TYPE: PRT
<213> ORGANISM: Artificial
<220> FEATURE:
<223> OTHER INFORMATION: SG-559-03 light chain CDR3

<400> SEQUENCE: 38

Gln Gln Arg Ser Asn Leu Pro Thr
1               5

<210> SEQ ID NO 39
<211> LENGTH: 453
<212> TYPE: PRT
<213> ORGANISM: Artificial
<220> FEATURE:
<223> OTHER INFORMATION: SG-559-04 LALA hIgG1 heavy chain

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Gly Phe Gly Met Asp Val
```

```
            100                 105                 110
Trp Gly Gln Gly Thr Thr Val Thr Val Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Val Glu Pro Lys
            210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
        450

<210> SEQ ID NO 40
<211> LENGTH: 213
<212> TYPE: PRT
<213> ORGANISM: Artificial
<220> FEATURE:
<223> OTHER INFORMATION: SG-559-04 kappa light chain

<400> SEQUENCE: 40

Glu Ile Val Leu Thr Gln Ser Pro Ala Thr Leu Ser Leu Ser Pro Gly
```

```
  1               5                  10                 15
Glu Arg Ala Thr Leu Ser Cys Arg Ala Ser Gln Ser Val Ser Ser Tyr
                20                  25                 30
Leu Ala Trp Tyr Gln Gln Lys Pro Gly Gln Ala Pro Arg Leu Leu Ile
                35                  40                 45
Tyr Asp Ala Ser Asn Arg Ala Thr Gly Ile Pro Ala Arg Phe Ser Gly
    50                  55                 60
Ser Gly Ser Gly Thr Asp Phe Thr Leu Thr Ile Ser Ser Leu Glu Pro
65                  70                  75                 80
Glu Asp Phe Ala Val Tyr Tyr Cys Gln Gln Arg Ser Asn Trp Pro Thr
                85                  90                 95
Phe Gly Gln Gly Thr Lys Val Glu Ile Lys Arg Thr Val Ala Ala Pro
                100                 105                110
Ser Val Phe Ile Phe Pro Pro Ser Asp Glu Gln Leu Lys Ser Gly Thr
                115                 120                125
Ala Ser Val Val Cys Leu Leu Asn Asn Phe Tyr Pro Arg Glu Ala Lys
        130                 135                140
Val Gln Trp Lys Val Asp Asn Ala Leu Gln Ser Gly Asn Ser Gln Glu
145                 150                 155                160
Ser Val Thr Glu Gln Asp Ser Lys Asp Ser Thr Tyr Ser Leu Ser Ser
                165                 170                175
Thr Leu Thr Leu Ser Lys Ala Asp Tyr Glu Lys His Lys Val Tyr Ala
                180                 185                190
Cys Glu Val Thr His Gln Gly Leu Ser Ser Pro Val Thr Lys Ser Phe
                195                 200                205
Asn Arg Gly Glu Cys
    210

<210> SEQ ID NO 41
<211> LENGTH: 123
<212> TYPE: PRT
<213> ORGANISM: Artificial
<220> FEATURE:
<223> OTHER INFORMATION: SG-559-04 heavy chain variable region

<400> SEQUENCE: 41

Gln Val Gln Leu Val Gln Ser Gly Ala Glu Val Lys Lys Pro Gly Ser
1               5                   10                 15
Ser Val Lys Val Ser Cys Lys Thr Ser Gly Asp Thr Phe Ser Thr Tyr
                20                  25                 30
Ala Ile Ser Trp Val Arg Gln Ala Pro Gly Gln Gly Leu Glu Trp Met
                35                  40                 45
Gly Gly Ile Ile Pro Ile Phe Gly Lys Ala His Tyr Ala Gln Lys Phe
    50                  55                 60
Gln Gly Arg Val Thr Ile Thr Ala Asp Glu Ser Thr Ser Thr Ala Tyr
65                  70                  75                 80
Met Glu Leu Ser Ser Leu Arg Ser Glu Asp Thr Ala Val Tyr Phe Cys
                85                  90                 95
Ala Arg Lys Phe His Phe Val Ser Gly Ser Gly Phe Gly Met Asp Val
                100                 105                110
Trp Gly Gln Gly Thr Thr Val Thr Val Ser Ser
                115                 120

<210> SEQ ID NO 42
<211> LENGTH: 106
<212> TYPE: PRT
```

```
<213> ORGANISM: Artificial
<220> FEATURE:
<223> OTHER INFORMATION: SG-559-04 light chain variable region

<400> SEQUENCE: 42

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 43
<211> LENGTH: 5
<212> TYPE: PRT
<213> ORGANISM: Artificial
<220> FEATURE:
<223> OTHER INFORMATION: SG-559-04 heavy chain CDR1

<400> SEQUENCE: 43

Thr Tyr Ala Ile Ser
1               5

<210> SEQ ID NO 44
<211> LENGTH: 17
<212> TYPE: PRT
<213> ORGANISM: Artificial
<220> FEATURE:
<223> OTHER INFORMATION: SG-559-04 heavy chain CDR2

<400> SEQUENCE: 44

Gly Ile Ile Pro Ile Phe Gly Lys Ala His Tyr Ala Gln Lys Phe Gln
1               5                   10                  15

Gly

<210> SEQ ID NO 45
<211> LENGTH: 14
<212> TYPE: PRT
<213> ORGANISM: Artificial
<220> FEATURE:
<223> OTHER INFORMATION: SG-559-04 heavy chain CDR3

<400> SEQUENCE: 45

Lys Phe His Phe Val Ser Gly Ser Gly Phe Gly Met Asp Val
1               5                   10

<210> SEQ ID NO 46
<211> LENGTH: 11
<212> TYPE: PRT
<213> ORGANISM: Artificial
<220> FEATURE:
<223> OTHER INFORMATION: SG-559-04 light chain CDR1

<400> SEQUENCE: 46

Arg Ala Ser Gln Ser Val Ser Ser Tyr Leu Ala
```

```
<210> SEQ ID NO 47
<211> LENGTH: 7
<212> TYPE: PRT
<213> ORGANISM: Artificial
<220> FEATURE:
<223> OTHER INFORMATION: SG-559-04 light chain CDR2

<400> SEQUENCE: 47

Asp Ala Ser Asn Arg Ala Thr
1               5

<210> SEQ ID NO 48
<211> LENGTH: 8
<212> TYPE: PRT
<213> ORGANISM: Artificial
<220> FEATURE:
<223> OTHER INFORMATION: SG-559-04 light chain CDR3

<400> SEQUENCE: 48

Gln Gln Arg Ser Asn Trp Pro Thr
1               5

<210> SEQ ID NO 49
<211> LENGTH: 17
<212> TYPE: PRT
<213> ORGANISM: Artificial
<220> FEATURE:
<223> OTHER INFORMATION: SG-559-05 heavy chain CDR2

<400> SEQUENCE: 49

Gly Ile Ile Pro Ile Ala Gly Lys Ala His Tyr Ala Gln Lys Phe Gln
1               5                   10                  15

Gly

<210> SEQ ID NO 50
<211> LENGTH: 17
<212> TYPE: PRT
<213> ORGANISM: Artificial
<220> FEATURE:
<223> OTHER INFORMATION: SG-559-06 heavy chain CDR2

<400> SEQUENCE: 50

Gly Ile Ile Pro Ile Phe Gly Ala Ala His Tyr Ala Gln Lys Phe Gln
1               5                   10                  15

Gly

<210> SEQ ID NO 51
<211> LENGTH: 17
<212> TYPE: PRT
<213> ORGANISM: Artificial
<220> FEATURE:
<223> OTHER INFORMATION: SG-559-07 heavy chain CDR2

<400> SEQUENCE: 51

Gly Ile Ile Pro Ile Phe Gly Arg Ala His Tyr Ala Gln Lys Phe Gln
1               5                   10                  15

Gly

<210> SEQ ID NO 52
<211> LENGTH: 17
<212> TYPE: PRT
<213> ORGANISM: Artificial
<220> FEATURE:
```

```
<223> OTHER INFORMATION: SG-559-08 heavy chain CDR2

<400> SEQUENCE: 52

Gly Ile Ile Pro Ile Phe Gly Lys Ala Ala Tyr Ala Gln Lys Phe Gln
1               5                   10                  15
Gly

<210> SEQ ID NO 53
<211> LENGTH: 17
<212> TYPE: PRT
<213> ORGANISM: Artificial
<220> FEATURE:
<223> OTHER INFORMATION: SG-559-09 heavy chain CDR2

<400> SEQUENCE: 53

Gly Ile Ile Pro Ile Phe Gly Lys Ala Phe Tyr Ala Gln Lys Phe Gln
1               5                   10                  15
Gly

<210> SEQ ID NO 54
<211> LENGTH: 14
<212> TYPE: PRT
<213> ORGANISM: Artificial
<220> FEATURE:
<223> OTHER INFORMATION: SG-559-10 heavy chain CDR3

<400> SEQUENCE: 54

Lys Phe His Phe Val Ser Gly Ala Pro Phe Gly Met Asp Val
1               5                   10

<210> SEQ ID NO 55
<211> LENGTH: 14
<212> TYPE: PRT
<213> ORGANISM: Artificial
<220> FEATURE:
<223> OTHER INFORMATION: SG-559-11 heavy chain CDR3

<400> SEQUENCE: 55

Lys Phe His Phe Val Ser Gly Ser Pro Ala Gly Met Asp Val
1               5                   10

<210> SEQ ID NO 56
<211> LENGTH: 8
<212> TYPE: PRT
<213> ORGANISM: Artificial
<220> FEATURE:
<223> OTHER INFORMATION: SG-559-12 light chain CDR3

<400> SEQUENCE: 56

Gln Gln Ala Ser Asn Trp Pro Thr
1               5

<210> SEQ ID NO 57
<211> LENGTH: 8
<212> TYPE: PRT
<213> ORGANISM: Artificial
<220> FEATURE:
<223> OTHER INFORMATION: SG-559-13 light chain CDR3

<400> SEQUENCE: 57

Gln Gln Lys Ser Asn Trp Pro Thr
1               5

<210> SEQ ID NO 58
<211> LENGTH: 8
```

```
<212> TYPE: PRT
<213> ORGANISM: Artificial
<220> FEATURE:
<223> OTHER INFORMATION: SG-559-14 light chain CDR3

<400> SEQUENCE: 58

Gln Gln Arg Ser Ala Trp Pro Thr
1               5

<210> SEQ ID NO 59
<211> LENGTH: 8
<212> TYPE: PRT
<213> ORGANISM: Artificial
<220> FEATURE:
<223> OTHER INFORMATION: SG-559-15 light chain CDR3

<400> SEQUENCE: 59

Gln Gln Arg Ser Gln Trp Pro Thr
1               5

<210> SEQ ID NO 60
<211> LENGTH: 8
<212> TYPE: PRT
<213> ORGANISM: Artificial
<220> FEATURE:
<223> OTHER INFORMATION: SG-559-16 light chain CDR3

<400> SEQUENCE: 60

Gln Gln Arg Ser Asn Ala Pro Thr
1               5

<210> SEQ ID NO 61
<211> LENGTH: 8
<212> TYPE: PRT
<213> ORGANISM: Artificial
<220> FEATURE:
<223> OTHER INFORMATION: SG-559-17 light chain CDR3

<400> SEQUENCE: 61

Gln Gln Arg Ser Asn Phe Pro Thr
1               5

<210> SEQ ID NO 62
<211> LENGTH: 453
<212> TYPE: PRT
<213> ORGANISM: Artificial
<220> FEATURE:
<223> OTHER INFORMATION: SG-559-01 hIgG1 heavy chain

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Ala
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110
```

```
Trp Gly Gln Gly Thr Thr Val Thr Val Ser Ser Ala Ser Thr Lys Gly
        115                 120                 125
Pro Ser Val Phe Pro Leu Ala Pro Ser Ser Lys Ser Thr Ser Gly Gly
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
        210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
        290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
        370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450

<210> SEQ ID NO 63
<211> LENGTH: 453
<212> TYPE: PRT
<213> ORGANISM: Artificial
<220> FEATURE:
<223> OTHER INFORMATION: SG-559-02 hIgG1 heavy chain

<400> SEQUENCE: 63

Gln Val Gln Leu Val Gln Ser Gly Ala Glu Val Lys Lys Pro Gly Ser
1               5                   10                  15
```

```
Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Lys Ala His Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

Val Met His Glu Ala Leu His Asn His Tyr Thr Gln Lys Ser Leu Ser
            435                 440                 445

Leu Ser Pro Gly Lys
        450

<210> SEQ ID NO 64
<211> LENGTH: 453
<212> TYPE: PRT
<213> ORGANISM: Artificial
<220> FEATURE:
<223> OTHER INFORMATION: SG-559-03 hIgG1 heavy chain

<400> SEQUENCE: 64

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

```
Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
435                 440                 445

Leu Ser Pro Gly Lys
            450

<210> SEQ ID NO 65
<211> LENGTH: 453
<212> TYPE: PRT
<213> ORGANISM: Artificial
<220> FEATURE:
<223> OTHER INFORMATION: SG-559-04 hIgG1 heavy chain

<400> SEQUENCE: 65

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Lys Ala His Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Gly Phe Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240
```

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 66
<211> LENGTH: 369
<212> TYPE: DNA
<213> ORGANISM: Artificial
<220> FEATURE:
<223> OTHER INFORMATION: SG-559-01 variable heavy region

<400> SEQUENCE: 66
caggtccagc tggtgcagtc tggggctgag gtgaagaagc ctgggtcctc ggtgaaggtc      60
tcctgcaaga cttctggaga caccttcagc accgccgcta tcagctgggt gcgacaggcc     120
cctggacaag gcttgagtg gatgggaggg atcatcccta tatttggtaa agcacactac     180
gcacagaagt tccagggcag agtcacgatt accgcggacg aatccacgag cacagcctac     240
atggagctga gcagcctgag atctgaggac acggccgtgt attttgtgc gagaaagttt     300 cactttgttt cggggagccc cttcggtatg gacgtctggg gccaagggac cacggtcacc     360
gtctcctca                                                            369

<210> SEQ ID NO 67
<211> LENGTH: 318
<212> TYPE: DNA
<213> ORGANISM: Artificial
<220> FEATURE:
<223> OTHER INFORMATION: SG-559-01 variable light region

<400> SEQUENCE: 67
gaaattgtgt tgacacagtc tccagccacc ctgtctttgt ctccagggga aagagccacc      60
ctctcctgca gggccagtca gagtgttagc agctacttag cctggtacca acagaaacct     120

```
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagttttatta ctgtcagcag cgtagcaact ggccgacgtt cggccaaggg    300
accaaggtgg aaatcaaa                                                  318
```

<210> SEQ ID NO 68
<211> LENGTH: 369
<212> TYPE: DNA
<213> ORGANISM: Artificial
<220> FEATURE:
<223> OTHER INFORMATION: SG-559-02 variable heavy region

<400> SEQUENCE: 68

```
caggtccagc tggtgcagtc tggggctgag gtgaagaagc ctgggtcctc ggtgaaggtc     60
tcctgcaaga cttctggaga caccttcagc acctatgcta tcagctgggt gcgacaggcc    120
cctggacaag gcttgagtg gatgggaggg atcatcccta tatttggtaa agcacactac    180
gcacagaagt tccagggcag agtcacgatt accgcggacg aatccacgag cacagcctac    240
atggagctga gcagcctgag atctgaggac acggccgtgt attttttgtgc gagaaagttt    300 cactttgttt cggggagccc cttcggtatg gacgtctggg gccaagggac cacggtcacc    360
gtctcctca                                                            369
```

<210> SEQ ID NO 69
<211> LENGTH: 318
<212> TYPE: PRT
<213> ORGANISM: Artificial
<220> FEATURE:
<223> OTHER INFORMATION: SG-559-02 variable light region

<400> SEQUENCE: 69

```
Gly Ala Ala Ala Thr Thr Gly Thr Gly Thr Thr Gly Ala Cys Ala Cys
1               5                   10                  15

Ala Gly Thr Cys Thr Cys Cys Ala Gly Cys Cys Ala Cys Cys Cys Thr
                20                  25                  30

Gly Thr Cys Thr Thr Thr Gly Thr Cys Thr Cys Cys Ala Gly Gly Gly
            35                  40                  45

Gly Ala Ala Ala Gly Ala Gly Cys Cys Ala Cys Cys Cys Thr Cys Thr
        50                  55                  60

Cys Cys Thr Gly Cys Ala Gly Gly Gly Cys Cys Ala Gly Thr Cys Ala
65                  70                  75                  80

Gly Ala Gly Thr Gly Thr Thr Ala Gly Cys Ala Gly Cys Ala Gly Cys
                85                  90                  95

Thr Thr Ala Gly Cys Cys Thr Gly Gly Thr Ala Cys Cys Ala Ala Cys
                100                 105                 110

Ala Gly Ala Ala Ala Cys Cys Thr Gly Gly Cys Cys Ala Gly Gly Cys
            115                 120                 125

Thr Cys Cys Cys Ala Gly Gly Cys Thr Cys Cys Thr Cys Ala Thr Cys
        130                 135                 140

Thr Ala Thr Gly Ala Thr Gly Cys Ala Thr Cys Cys Ala Ala Cys Ala
145                 150                 155                 160

Gly Gly Gly Cys Cys Ala Cys Thr Gly Gly Cys Ala Thr Cys Cys Cys
                165                 170                 175

Ala Gly Cys Cys Ala Gly Gly Thr Thr Cys Ala Gly Thr Gly Gly Cys
            180                 185                 190
```

Ala Gly Thr Gly Gly Gly Thr Cys Thr Gly Gly Ala Cys Ala Gly
            195                 200                 205

Ala Cys Thr Thr Cys Ala Cys Thr Cys Thr Cys Ala Cys Cys Ala Thr
            210                 215                 220

Cys Ala Gly Cys Ala Gly Cys Cys Thr Ala Gly Ala Gly Cys Cys Thr
225                 230                 235                 240

Gly Ala Ala Gly Ala Thr Thr Thr Thr Gly Cys Ala Gly Thr Thr Thr
                245                 250                 255

Ala Thr Thr Ala Cys Thr Gly Thr Cys Ala Gly Cys Ala Gly Cys Gly
            260                 265                 270

Thr Ala Gly Cys Ala Ala Cys Thr Gly Gly Cys Cys Gly Ala Cys Gly
            275                 280                 285

Thr Thr Cys Gly Gly Cys Cys Ala Ala Gly Gly Gly Ala Cys Cys Ala
            290                 295                 300

Ala Gly Gly Thr Gly Gly Ala Ala Ala Thr Cys Ala Ala Ala
305                 310                 315

<210> SEQ ID NO 70
<211> LENGTH: 369
<212> TYPE: DNA
<213> ORGANISM: Artificial
<220> FEATURE:
<223> OTHER INFORMATION: SG-559-03 variable heavy region

<400> SEQUENCE: 70
caggtccagc tggtgcagtc tggggctgag gtgaagaagc ctgggtcctc ggtgaaggtc    60
tcctgcaaga cttctggaga caccttcagc acctatgcta tcagctgggt gcgacaggcc   120
cctggacaag gcttgagtg gatgggaggg atcatcccta tatttggtaa agcacactac    180
gcacagaagt tccagggcag agtcacgatt accgcggacg aatccacgag cacagcctac   240
atggagctga gcagcctgag atctgaggac acggccgtgt attttgtgc gagaaagttt    300 cactttgttt cggggagccc cttcggtatg gacgtctggg gccaagggac cacggtcacc   360
gtctcctca                                                           369

<210> SEQ ID NO 71
<211> LENGTH: 318
<212> TYPE: DNA
<213> ORGANISM: Artificial
<220> FEATURE:
<223> OTHER INFORMATION: SG-559-03 variable light region

<400> SEQUENCE: 71
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaacc tgccgacgtt cggccaaggg   300
accaaggtgg aaatcaaa                                                 318

<210> SEQ ID NO 72
<211> LENGTH: 369
<212> TYPE: DNA
<213> ORGANISM: Artificial
<220> FEATURE:
<223> OTHER INFORMATION: SG-559-04 variable heavy region

<400> SEQUENCE: 72

```
caggtccagc tggtgcagtc tggggctgag gtgaagaagc ctgggtcctc ggtgaaggtc      60
tcctgcaaga cttctggaga caccttcagc acctatgcta tcagctgggt gcgacaggcc     120
cctggacaag ggcttgagtg gatgggaggg atcatcccta tatttggtaa agcacactac     180
gcacagaagt tccagggcag agtcacgatt accgcgacg aatccacgag cacagcctac      240
atggagctga gcagcctgag atctgaggac acggccgtgt attttgtgc gagaaagttt      300 cactttgttt cggggagcgg cttcggtatg gacgtctggg gccaagggac cacggtcacc     360
gtctcctca                                                             369
```

<210> SEQ ID NO 73
<211> LENGTH: 318
<212> TYPE: DNA
<213> ORGANISM: Artificial
<220> FEATURE:
<223> OTHER INFORMATION: SG-559-04 variable light region

<400> SEQUENCE: 73

```
gaaattgtgt tgacacagtc tccagccacc ctgtctttgt ctccagggga agagccacc     60 ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggccgacgtt cggccaaggg    300
accaaggtgg aaatcaaa                                                  318
```

<210> SEQ ID NO 74
<211> LENGTH: 1359
<212> TYPE: DNA
<213> ORGANISM: Artificial
<220> FEATURE:
<223> OTHER INFORMATION: SG-559-01 LALA hIgG1 heavy chain

<400> SEQUENCE: 74

```
caggtccagc tggtgcagtc tggggctgag gtgaagaagc ctgggtcctc ggtgaaggtc     60
tcctgcaaga cttctggaga caccttcagc accgccgcta tcagctgggt gcgacaggcc    120
cctggacaag ggcttgagtg gatgggaggg atcatcccta tatttggtaa agcacactac    180
gcacagaagt tccagggcag agtcacgatt accgcgacg aatccacgag cacagcctac     240
atggagctga gcagcctgag atctgaggac acggccgtgt attttgtgc gagaaagttt     300 cactttgttt cggggagccc cttcggtatg gacgtctggg gccaagggac cacggtcacc    360
gtctcctcag ctagcaccaa gggcccatct gtcttccccc tggcaccctc ctccaagagc    420
acctctgggg gcacagctgc cctgggctgc ctggtcaagg actacttccc tgaacctgtg    480
acagtgtcct ggaactcagg agccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaaa    660
gttgagccca aatcttgtga caaaactcac acatgcccac cgtgcccagc acctgaagct    720 gctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
```

| | |
|---|---|
| aatggcaagg agtacaagtg caaggtctcc aacaaagccc tcccagcccc catcgagaaa | 1020 |
| accatctcca agccaaagg gcagccccga gaaccacagg tttacaccct gcccccatcc | 1080 |
| cgggatgagc tgaccaagaa ccaggtcagc ctgacctgcc tggtcaaagg cttctatccc | 1140 |
| agcgacatcg ccgtggagtg ggagagcaat gggcagccgg agaacaacta caagaccacg | 1200 |
| cctcccgtgc tggactccga cggctccttc ttcctctaca gcaagctcac cgtggacaag | 1260 |
| agcaggtggc agcaggggaa cgtcttctca tgctccgtga tgcatgaggc tctgcacaac | 1320 |
| cactacacac agaagagcct ctccctgtct ccgggcaaa | 1359 |

<210> SEQ ID NO 75
<211> LENGTH: 639
<212> TYPE: DNA
<213> ORGANISM: Artificial
<220> FEATURE:
<223> OTHER INFORMATION: SG-559-01 kappa light chain

<400> SEQUENCE: 75

| | |
|---|---|
| gaaattgtgt tgacacagtc tccagccacc ctgtctttgt ctccagggga aagagccacc | 60 |
| ctctcctgca gggccagtca gagtgttagc agctacttag cctggtacca acagaaacct | 120 |
| ggccaggctc ccaggctcct catctatgat gcatccaaca gggccactgg catcccagcc | 180 |
| aggttcagtg gcagtgggtc tgggacagac ttcactctca ccatcagcag cctagagcct | 240 |
| gaagattttg cagtttatta ctgtcagcag cgtagcaact ggccgacgtt cggccaaggg | 300 |
| accaaggtgg aaatcaaacg tacggtggct gcaccatctg tcttcatctt cccgccatct | 360 |
| gatgagcagt tgaaatctgg aactgcctct gttgtgtgcc tgctgaataa cttctatccc | 420 |
| agagaggcca agtacagtg gaaggtggat aacgccctcc aatcgggtaa ctcccaggag | 480 |
| agtgtcacag agcaggacag caaggacagc acctacagcc tcagcagcac cctgacgctg | 540 |
| agcaaagcag actacgagaa acacaaagtc tacgcctgcg aagtcaccca tcagggcctg | 600 |
| agctcgcccg tcacaaagag cttcaacagg ggagagtgt | 639 |

<210> SEQ ID NO 76
<211> LENGTH: 1359
<212> TYPE: DNA
<213> ORGANISM: Artificial
<220> FEATURE:
<223> OTHER INFORMATION: SG-559-01 hIgG1 heavy chain

<400> SEQUENCE: 76

| | |
|---|---|
| caggtccagc tggtgcagtc tggggctgag gtgaagaagc ctgggtcctc ggtgaaggtc | 60 |
| tcctgcaaga cttctggaga caccttcagc accgccgcta tcagctgggt gcgacaggcc | 120 |
| cctggacaag gccttgagtg gatgggaggg atcatcccta tatttggtaa agcacactac | 180 |
| gcacagaagt tccagggcag agtcacgatt accgcggacg aatccacgag cacagcctac | 240 |
| atggagctga gcagcctgag atctgaggac acggccgtgt attttgtgc gagaaagttt | 300 |
| cactttgttt cggggagccc cttcggtatg gacgtctggg gccaagggac cacggtcacc | 360 |
| gtctcctcag ctagcaccaa gggcccatct gtcttccccc tggcaccctc ctccaagagc | 420 |
| acctctgggg gcacagctgc cctgggctgc ctggtcaagg actacttccc tgaacctgtg | 480 |
| acagtgtcct ggaactcagg agccctgacc agcggcgtgc acaccttccc ggctgtccta | 540 |
| cagtcctcag gactctactc cctcagcagc gtggtgaccg tgccctccag cagcttgggc | 600 |
| acccagacct acatctgcaa cgtgaatcac aagcccagca acaccaaggt ggacaagaaa | 660 |
| gttgagccca atcttgtga caaaactcac acatgcccac cgtgcccagc acctgaactc | 720 |

```
ctgggggac cgtcagtctt cctcttcccc ccaaaaccca aggacaccct catgatctcc    780 cggaccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa    1020
accatctcca aagccaaagg gcagccccga gaaccacagg tgtacaccct gcccccatcc    1080
cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacac agaagagcct ctccctgtct ccgggcaaa    1359
```

<210> SEQ ID NO 77
<211> LENGTH: 1359
<212> TYPE: DNA
<213> ORGANISM: Artificial
<220> FEATURE:
<223> OTHER INFORMATION: SG-559-02 LALA hIgG1 heavy chain

<400> SEQUENCE: 77

```
caggtccagc tggtgcagtc tggggctgag gtgaagaagc ctgggtcctc ggtgaaggtc    60
tcctgcaaga cttctggaga caccttcagc acctatgcta tcagctgggt gcgacaggcc    120
cctggacaag gcttgagtg gatgggaggg atcatcccta tatttggtaa agcacactac    180
gcacagaagt tccagggcag agtcacgatt accgcggacg aatccacgag cacagcctac    240
atggagctga gcagcctgag atctgaggac acggccgtgt attttgtgc gagaaagttt    300 cactttgttt cggggagccc cttcggtatg gacgtctggg gccaagggac cacggtcacc    360
gtctcctcag ctagcaccaa gggcccatct gtcttccccc tggcaccctc ctccaagagc    420
acctctgggg gcacagctgc cctgggctgc ctggtcaagg actacttccc tgaacctgtg    480
acagtgtcct ggaactcagg agccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaaa    660
gttgagccca aatcttgtga caaaactcac acatgcccac cgtgcccagc acctgaagct    720 gctggggac cgtcagtctt cctcttcccc ccaaaaccca aggacaccct catgatctcc    780 cggaccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa    1020
accatctcca aagccaaagg gcagccccga gaaccacagg tttacaccct gcccccatcc    1080
cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacac agaagagcct ctccctgtct ccgggcaaa    1359
```

<210> SEQ ID NO 78
<211> LENGTH: 639
<212> TYPE: DNA
<213> ORGANISM: Artificial
<220> FEATURE:
<223> OTHER INFORMATION: SG-559-02 kappa light chain

<400> SEQUENCE: 78

```
gaaattgtgt tgacacagtc tccagccacc ctgtctttgt ctccagggga aagagccacc      60
ctctcctgca gggccagtca gagtgttagc agcgccttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggccgacgtt cggccaaggg     300
accaaggtgg aaatcaaacg tacggtggct gcaccatctg tcttcatctt cccgccatct     360
gatgagcagt tgaaatctgg aactgcctct gttgtgtgcc tgctgaataa cttctatccc     420
agagaggcca aagtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgt                           639
```

<210> SEQ ID NO 79
<211> LENGTH: 1359
<212> TYPE: DNA
<213> ORGANISM: Artificial
<220> FEATURE:
<223> OTHER INFORMATION: SG-559-02 hIgG1 heavy chain

<400> SEQUENCE: 79

```
caggtccagc tggtgcagtc tggggctgag gtgaagaagc ctgggtcctc ggtgaaggtc      60
tcctgcaaga cttctggaga caccttcagc acctatgcta tcagctgggt gcgacaggcc     120
cctggacaag gcttgagtg gatgggaggg atcatcccta tatttggtaa agcacactac     180
gcacagaagt tccagggcag agtcacgatt accgcggacg aatccacgag cacagcctac     240
atggagctga gcagcctgag atctgaggac acggccgtgt attttgtgc gagaaagttt     300
cactttgttt cggggagccc cttcggtatg gacgtctggg gccaagggac cacggtcacc     360
gtctcctcag ctagcaccaa gggcccatct gtcttccccc tggcaccctc ctccaagagc     420
acctctgggg gcacagctgc cctgggctgc ctggtcaagg actacttccc tgaacctgtg     480
acagtgtcct ggaactcagg agccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca caccaaggt ggacaagaaa     660
gttgagccca aatcttgtga caaaactcac acatgcccac cgtgcccagc acctgaactc     720
ctgggggac cgtcagtctt cctcttcccc ccaaaaccca aggacaccct catgatctcc     780
cggacccctg aggtcacatg cgtggtggtg gacgtgagcc acgaagaccc tgaggtcaag     840
ttcaactggt acgtggacgg cgtggaggtg cataatgcca agacaaagcc gcgggaggag     900
cagtacaaca gcacgtaccg tgtggtcagc gtcctcaccg tcctgcacca ggactggctg     960
aatggcaagg agtacaagtg caaggtctcc aacaaagccc tcccagcccc catcgagaaa    1020
accatctcca aagccaaagg gcagcccga gaaccacagg tgtacaccct gcccccatcc    1080
cgggatgagc tgaccaagaa ccaggtcagc ctgacctgcc tggtcaaagg cttctatccc    1140
```

```
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacac agaagagcct ctccctgtct ccgggcaaa                           1359
```

<210> SEQ ID NO 80
<211> LENGTH: 1359
<212> TYPE: DNA
<213> ORGANISM: Artificial
<220> FEATURE:
<223> OTHER INFORMATION: SG-559-03 LALA hIgG1 heavy chain

<400> SEQUENCE: 80

```
caggtccagc tggtgcagtc tggggctgag gtgaagaagc ctgggtcctc ggtgaaggtc      60
tcctgcaaga cttctggaga caccttcagc acctatgcta tcagctgggt gcgacaggcc     120
cctggacaag gcttgagtg gatgggaggg atcatcccta tatttggtaa agcacactac     180
gcacagaagt tccagggcag agtcacgatt accgcggacg aatccacgag cacagcctac     240
atggagctga gcagcctgag atctgaggac acggccgtgt attttgtgc gagaaagttt     300 cactttgttt cggggagccc cttcggtatg gacgtctggg gccaagggac cacggtcacc     360
gtctcctcag ctagcaccaa gggcccatct gtcttccccc tggcaccctc ctccaagagc     420
acctctgggg gcacagctgc cctgggctgc ctggtcaagg actacttccc tgaacctgtg     480
acagtgtcct ggaactcagg agccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca acaccaaggt ggacaagaaa     660
gttgagccca atcttgtga caaaactcac acatgcccac cgtgcccagc acctgaagct     720 gctggggac cgtcagtctt cctcttcccc ccaaaaccca aggacaccct catgatctcc     780 cggaccctg aggtcacatg cgtggtggtg gacgtgagcc acgaagaccc tgaggtcaag     840
ttcaactggt acgtggacgg cgtggaggtg cataatgcca agacaaagcc gcggaggag     900 cagtacaaca gcacgtaccg tgtggtcagc gtcctcaccg tcctgcacca ggactggctg     960
aatggcaagg agtacaagtg caaggtctcc aacaaagccc tcccagcccc catcgagaaa    1020
accatctcca aagccaaagg gcagccccga gaaccacagg tttacaccct gcccccatcc    1080
cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacac agaagagcct ctccctgtct ccgggcaaa                           1359
```

<210> SEQ ID NO 81
<211> LENGTH: 639
<212> TYPE: DNA
<213> ORGANISM: Artificial
<220> FEATURE:
<223> OTHER INFORMATION: SG-559-03 kappa light chain

<400> SEQUENCE: 81

```
gaaattgtgt tgacacagtc tccagccacc ctgtctttgt ctccagggga aagagccacc     60
ctctcctgca gggccagtca gagtgttagc agctacttag cctggtacca acagaaacct    120
```

| | |
|---|---|
| ggccaggctc ccaggctcct catctatgat gcatccaaca gggccactgg catcccagcc | 180 |
| aggttcagtg gcagtgggtc tgggacagac ttcactctca ccatcagcag cctagagcct | 240 |
| gaagattttg cagtttatta ctgtcagcag cgtagcaacc tgccgacgtt cggccaaggg | 300 |
| accaaggtgg aaatcaaacg tacggtggct gcaccatctg tcttcatctt cccgccatct | 360 |
| gatgagcagt tgaaatctgg aactgcctct gttgtgtgcc tgctgaataa cttctatccc | 420 |
| agagaggcca agtacagtg gaaggtggat aacgccctcc aatcgggtaa ctcccaggag | 480 |
| agtgtcacag agcaggacag caaggacagc acctacagcc tcagcagcac cctgacgctg | 540 |
| agcaaagcag actacgagaa acacaaagtc tacgcctgcg aagtcaccca tcagggcctg | 600 |
| agctcgcccg tcacaaagag cttcaacagg ggagagtgt | 639 |

<210> SEQ ID NO 82
<211> LENGTH: 1359
<212> TYPE: DNA
<213> ORGANISM: Artificial
<220> FEATURE:
<223> OTHER INFORMATION: SG-559-03 hIgG1 heavy chain

<400> SEQUENCE: 82

| | |
|---|---|
| caggtccagc tggtgcagtc tggggctgag gtgaagaagc ctgggtcctc ggtgaaggtc | 60 |
| tcctgcaaga cttctggaga caccttcagc acctatgcta tcagctgggt gcgacaggcc | 120 |
| cctggacaag gcttgagtg gatgggaggg atcatcccta tatttggtaa agcacactac | 180 |
| gcacagaagt tccagggcag agtcacgatt accgcggacg aatccacgag cacagcctac | 240 |
| atggagctga gcagcctgag atctgaggac acggccgtgt attttgtgc gagaaagttt | 300 |
| cactttgttt cggggagccc cttcggtatg gacgtctggg gccaagggac cacggtcacc | 360 |
| gtctcctcag ctagcaccaa gggcccatcg gtcttccccc tggcaccctc ctccaagagc | 420 |
| acctctgggg gcacagctgc cctgggctgc ctggtcaagg actacttccc tgaacctgtg | 480 |
| acagtgtcct ggaactcagg agccctgacc agcggcgtgc acaccttccc ggctgtccta | 540 |
| cagtcctcag gactctactc cctcagcagc gtggtgaccg tgccctccag cagcttgggc | 600 |
| acccagacct acatctgcaa cgtgaatcac aagcccagca acaccaaggt ggacaagaaa | 660 |
| gttgagccca aatcttgtga caaaactcac acatgcccac cgtgcccagc acctgaactc | 720 |
| ctggggggac cgtcagtctt cctcttcccc ccaaaaccca aggacaccct catgatctcc | 780 |
| cggacccctg aggtcacatg cgtggtggtg gacgtgagcc acgaagaccc tgaggtcaag | 840 |
| ttcaactggt acgtggacgg cgtggaggtg cataatgcca agacaaagcc gcgggaggag | 900 |
| cagtacaaca gcacgtaccg tgtggtcagc gtcctcaccg tcctgcacca ggactggctg | 960 |
| aatggcaagg agtacaagtg caaggtctcc aacaaagccc tcccagcccc catcgagaaa | 1020 |
| accatctcca aagccaaagg gcagccccga gaaccacagg tgtacaccct gcccccatcc | 1080 |
| cgggatgagc tgaccaagaa ccaggtcagc ctgacctgcc tggtcaaagg cttctatccc | 1140 |
| agcgacatcg ccgtggagtg ggagagcaat gggcagccgg agaacaacta caagaccacg | 1200 |
| cctcccgtgc tggactccga cggctccttc ttcctctaca gcaagctcac cgtggacaag | 1260 |
| agcaggtggc agcaggggaa cgtcttctca tgctccgtga tgcatgaggc tctgcacaac | 1320 |
| cactacacac agaagagcct ctccctgtct ccgggcaaa | 1359 |

<210> SEQ ID NO 83
<211> LENGTH: 1359
<212> TYPE: DNA
<213> ORGANISM: Artificial

```
<220> FEATURE:
<223> OTHER INFORMATION: SG-559-04 LALA hIgG1 heavy chain

<400> SEQUENCE: 83
caggtccagc tggtgcagtc tggggctgag gtgaagaagc ctgggtcctc ggtgaaggtc      60
tcctgcaaga cttctggaga caccttcagc acctatgcta tcagctgggt gcgacaggcc     120
cctggacaag gcttgagtg gatgggaggg atcatcccta tatttggtaa agcacactac     180
gcacagaagt tccagggcag agtcacgatt accgcggacg aatccacgag cacagcctac     240
atggagctga gcagcctgag atctgaggac acggccgtgt attttgtgc gagaaagttt     300
cactttgttt cggggagcgg cttcggtatg acgtctggg gccaagggac cacggtcacc     360
gtctcctcag ctagcaccaa gggcccatct gtcttcccc tggcaccctc ctccaagagc     420
acctctgggg gcacagctgc cctgggctgc ctggtcaagg actacttccc tgaacctgtg     480
acagtgtcct ggaactcagg agccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca caccaaggt ggacaagaaa     660
gttgagccca atcttgtga caaaactcac acatgcccac cgtgcccagc acctgaagct     720
gctggggac cgtcagtctt cctcttcccc ccaaaaccca aggacaccct catgatctcc     780
cggacccctg aggtcacatg cgtggtggtg gacgtgagcc acgaagaccc tgaggtcaag     840
ttcaactggt acgtggacgg cgtggaggtg cataatgcca agacaaagcc gcgggaggag     900
cagtacaaca gcacgtaccg tgtggtcagc gtcctcaccg tcctgcacca ggactggctg     960
aatggcaagg agtacaagtg caaggtctcc aacaaagccc tcccagcccc catcgagaaa    1020
accatctcca agccaaagg gcagccccga gaaccacagg tttacaccct gcccccatcc    1080
cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacac agaagagcct ctccctgtct ccgggcaaa                            1359

<210> SEQ ID NO 84
<211> LENGTH: 639
<212> TYPE: DNA
<213> ORGANISM: Artificial
<220> FEATURE:
<223> OTHER INFORMATION: SG-559-04 kappa light chain

<400> SEQUENCE: 84
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggccgacgtt cggccaaggg     300
accaaggtgg aaatcaaacg tacgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
```

-continued

| | |
|---|---|
| agcaaagcag actacgagaa acacaaagtc tacgcctgcg aagtcaccca tcagggcctg | 600 |
| agctcgcccg tcacaaagag cttcaacagg ggagagtgt | 639 |

<210> SEQ ID NO 85
<211> LENGTH: 1359
<212> TYPE: DNA
<213> ORGANISM: Artificial
<220> FEATURE:
<223> OTHER INFORMATION: SG-559-04 hIgG1 heavy chain

<400> SEQUENCE: 85

| | |
|---|---|
| caggtccagc tggtgcagtc tggggctgag gtgaagaagc ctgggtcctc ggtgaaggtc | 60 |
| tcctgcaaga cttctggaga caccttcagc acctatgcta tcagctgggt gcgacaggcc | 120 |
| cctggacaag gcttgagtg gatgggaggg atcatcccta tatttggtaa agcacactac | 180 |
| gcacagaagt tccagggcag agtcacgatt accgcggacg aatccacgag cacagcctac | 240 |
| atggagctga gcagcctgag atctgaggac acggccgtgt attttgtgc gagaaagttt | 300 |
| cactttgttt cggggagcgg cttcggtatg gacgtctggg gccaagggac cacggtcacc | 360 |
| gtctcctcag ctagcaccaa gggcccatct gtcttccccc tggcaccctc ctccaagagc | 420 |
| acctctgggg gcacagctgc cctgggctgc ctggtcaagg actacttccc tgaacctgtg | 480 |
| acagtgtcct ggaactcagg agccctgacc agcggcgtgc acaccttccc ggctgtccta | 540 |
| cagtcctcag gactctactc cctcagcagc gtggtgaccg tgccctccag cagcttgggc | 600 |
| acccagacct acatctgcaa cgtgaatcac aagcccagca acaccaaggt ggacaagaaa | 660 |
| gttgagccca aatcttgtga caaaactcac acatgcccac cgtgcccagc acctgaactc | 720 |
| ctgggggac cgtcagtctt cctcttcccc ccaaaaccca aggacaccct catgatctcc | 780 |
| cggacccctg aggtcacatg cgtggtggtg gacgtgagcc acgaagaccc tgaggtcaag | 840 |
| ttcaactggt acgtggacgg cgtggaggtg cataatgcca agacaaagcc gcgggaggag | 900 |
| cagtacaaca gcacgtaccg tgtggtcagc gtcctcaccg tcctgcacca ggactggctg | 960 |
| aatggcaagg agtacaagtg caaggtctcc aacaaagccc tcccagcccc catcgagaaa | 1020 |
| accatctcca aagccaaagg gcagcccga gaaccacagg tgtacaccct gcccccatcc | 1080 |
| cgggatgagc tgaccaagaa ccaggtcagc ctgacctgcc tggtcaaagg cttctatccc | 1140 |
| agcgacatcg ccgtggagtg ggagagcaat gggcagccgg agaacaacta caagaccacg | 1200 |
| cctcccgtgc tggactccga cggctccttc ttcctctaca gcaagctcac cgtggacaag | 1260 |
| agcaggtggc agcaggggaa cgtcttctca tgctccgtga tgcatgaggc tctgcacaac | 1320 |
| cactacacac agaagagcct ctccctgtct ccgggcaaa | 1359 |

<210> SEQ ID NO 86
<211> LENGTH: 453
<212> TYPE: PRT
<213> ORGANISM: Artificial
<220> FEATURE:
<223> OTHER INFORMATION: Ab1 hIgG1 heavy chain

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

```
Gly Gly Ile Ile Pro Ile Phe Gly Lys Ala His Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
450
```

```
<210> SEQ ID NO 87
<211> LENGTH: 213
<212> TYPE: PRT
<213> ORGANISM: Artificial
<220> FEATURE:
<223> OTHER INFORMATION: Ab1 kappa light chain

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

ANTI-PD-L1 ANTIBODIES AND ANTIBODY-DRUG CONJUGATES

CROSS-REFERENCE TO RELATED APPLICATIONS

This application claims priority to U.S. Patent Application No. 62/910,988, filed Oct. 4, 2019, which is herein incorporated by reference in its entirety.

REFERENCE TO SEQUENCE LISTING

This application is being filed electronically via EFS-Web and includes an electronically submitted sequence listing in .txt format. The .txt file contains a sequence listing entitled "20201002 USSequence Listing (1362169F).txt" created on Oct. 2, 2020 and having a size of 90 KB. The sequence listing contained in this .txt file is part of the specification and is incorporated herein by reference in its entirety.

TECHNICAL FIELD

The present invention relates to novel anti-PD-L1 antibodies and antibody-drug conjugates and methods of using such anti-PD-L1 antibodies and antibody-drug conjugates to treat cancer.

BACKGROUND

PD-L1, which is also known as Programmed Death-Ligand 1, B7-H1, or CD274, is a protein that has been shown to be expressed in a variety of cancer cells. PD-L1 is a transmembrane protein that can interact with PD-1 and act as an "off" switch to inactivate T cells. PD-L1 is commonly overexpressed on tumor cells, and binding to PD-1 allows tumors to avoid a T cell immune response.

There are several cancers that express PD-L1, including melanoma. Melanoma is the most dangerous type of skin cancer. In 2015, there were 3.1 million people with active disease and melanoma resulted in 59,800 deaths. The five-year survival rate of stage IV disease is less than 10%, with median survival of only 6-12 months. Therefore, there is a need for improved treatments for melanoma, as well as other cancers that express PD-L1. One type of treatment for cancers that express PD-L1 includes administering anti-PD-L1 antibodies as an immunotherapy. Immuno-oncology is a promising field for cancer treatment, but there is room for improvement to current therapies.

All references cited herein, including patent applications, patent publications, and scientific literature, are herein incorporated by reference in their entirety, as if each individual reference were specifically and individually indicated to be incorporated by reference.

SUMMARY

Provided herein are anti-PD-L1 antibodies and PD-L1-directed antibody-drug conjugates (ADCs). In particular, provided herein are PD-L1-directed camptothecin ADCs and MMAE ADCs. Also provided herein are methods of using anti-PD-L1-directed antibodies and ADCs to treat PD-L1-expressing disorders. Preferred anti-PD-L1 antibodies exhibit a binding affinity to the human PD-L1 protein that is between 3 nM and 300 nM. Other preferred anti-PD-L1 antibodies comprise heavy chain CDR sequences of SEQ ID NOs: 3-5 and light chain CDR sequences of SEQ ID NOs: 6-8, wherein the antibodies comprise one or more amino acid substitutions within one or more of the CDRs. Other preferred anti-PD-L1 antibodies comprise heavy chain CDR sequences of SEQ ID NOs: 13-15 and light chain CDR sequences of SEQ ID NOs: 16-18.

Also provided herein are antibodies or antigen-binding fragments thereof that specifically bind to the human Programmed Death-Ligand 1 (PD-L1) protein, where the antibody exhibits a binding affinity to the human PD-L1 protein that is between 3 and 300 nM. In some embodiments, the antibody exhibits a binding affinity to the human PD-L1 protein that is between 3 and 15 nM.

In some embodiments, the antibody further exhibits a total internalization that is higher than the total internalization of Ab1. In some embodiments, the total internalization is between a 9% and 155% increase of AUC over the AUC of Ab1. In some embodiments, the total internalization is determined by a FabFluor internalization assay.

In some embodiments, the antibody further exhibits an x50 that is lower than the x50 of Ab1. In some embodiments, the antibody is conjugated to monomethyl auristatin E (MMAE), and wherein the x50 is between 3 ng/mL and 20 ng/mL in an MDA-MB-231 cell line.

In some embodiments, the antibody is conjugated to camptothecin, and where the x50 is between 15 ng/mL and 55 ng/mL in an MDA-MB-231 cell line.

In some embodiments, the antibody includes heavy chain CDR sequences of SEQ ID NOs: 13-15 and light chain CDR sequences of SEQ ID NOs: 16-18.

In some embodiments, the antibody includes heavy chain CDR sequences of SEQ ID NOs: 3-5 and light chain CDR sequences of SEQ ID NOs: 6-8, wherein the antibody includes one or more amino acid substitutions within one or more of the CDRs.

In some embodiments, the antibody includes a heavy chain variable region sequence having at least 80% sequence identity to SEQ ID NO: 11 and a light chain variable region sequence having at least 80% sequence identity to SEQ ID NO: 12. In some embodiments, the antibody includes a heavy chain variable region sequence having at least 90% sequence identity to SEQ ID NO: 11 and a light chain variable region sequence having at least 90% sequence identity to SEQ ID NO: 12. In some embodiments, the antibody includes a heavy chain variable region sequence having at least 95% sequence identity to SEQ ID NO: 11 and a light chain variable region sequence having at least 95% sequence identity to SEQ ID NO: 12. In some embodiments, the antibody includes a heavy chain variable region sequence of SEQ ID NO: 11 and a light chain variable region sequence of SEQ ID NO: 12.

In some embodiments, the antibody includes the heavy chain sequence of SEQ ID NO: 9 and the light chain sequence of SEQ ID NO: 10.

In some embodiments, the fragment is a Fab, Fab', F(ab')$_2$, Fab'-SH, Fv, diabody, linear antibody, or single-chain antibody fragment.

In some embodiments, the antibody contains L234A and L235A mutations in the heavy chain of the antibody.

In some embodiments, the heavy chain constant region is of the IgG1 isotype.

In some embodiments, the antibody is a humanized or chimeric antibody.

In some embodiments, the antibody is conjugated to a cytotoxic agent via a linker.

In some embodiments, the antibody is conjugated to monomethyl auristatin E (MMAE). In some embodiments, the antibody is conjugated to MMAE via an enzyme-cleavable linker unit. In some embodiments, the enzyme-cleavable linker unit includes a Val-Cit linker. In some embodiments, the antibody is conjugated to MMAE via a linker forming an antibody-drug conjugate having the structure:

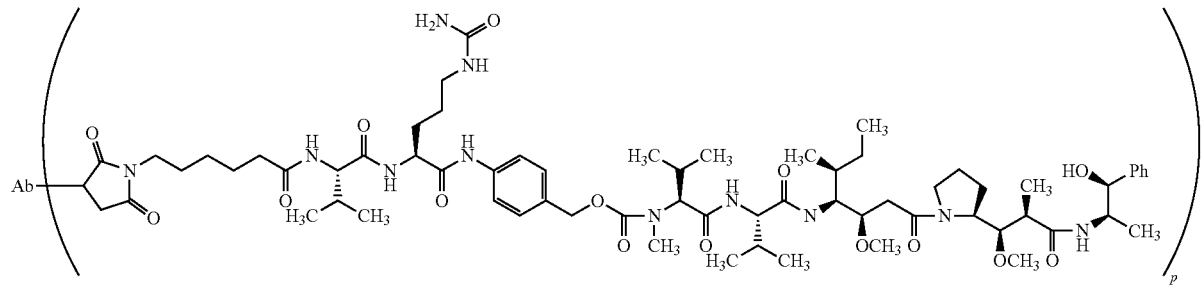

where Ab represents the antibody and p ranges from 2 to 10. In some embodiments, p is 4. In some embodiments, p is 8.

In some embodiments, the antibody is conjugated to camptothecin. In some embodiments, the antibody is conjugated to camptothecin via an enzyme-cleavable linker unit. In some embodiments, the enzyme-cleavable linker unit includes a Val-Lys-Gly linker. In some embodiments, the antibody is conjugated to camptothecin via a linker forming an antibody-drug conjugate having the structure:

tion of Ab1. In some embodiments, the total internalization is between a 9% and 155% increase of AUC over the AUC of Ab1. In some embodiments, the total internalization is determined by a FabFluor internalization assay.

In some embodiments, the antibody further exhibits an x50 that is higher than the x50 of Ab1.

In some embodiments, the antibody is conjugated to monomethyl auristatin E (MMAE), and where the x50 is between 3 ng/mL and 20 ng/mL in an MDA-MB-231 cell line.

In some embodiments, the antibody is conjugated to camptothecin, and where the x50 is between 15 ng/mL and 55 ng/mL in an MDA-MB-231 cell line.

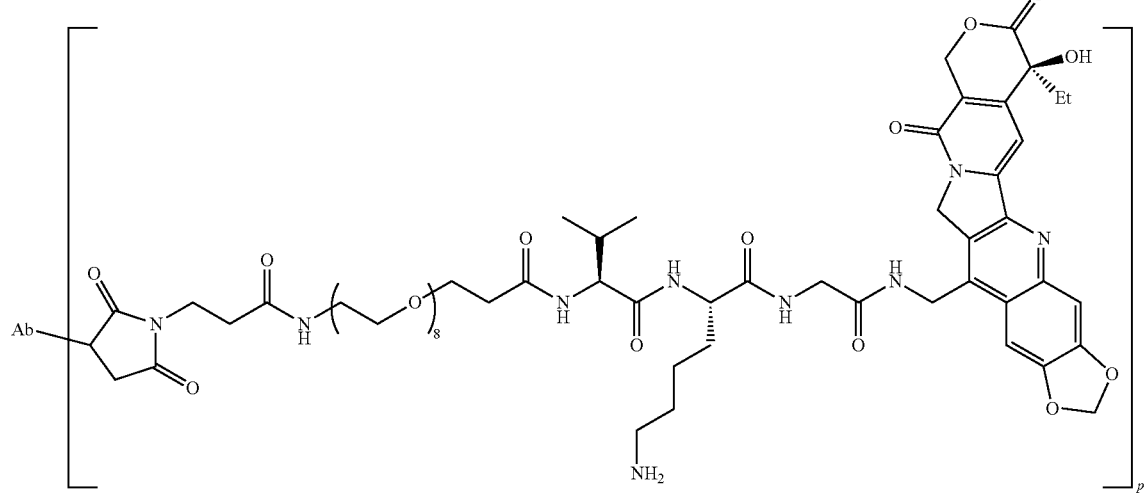

where Ab represents the antibody and p ranges from 2 to 10. In some embodiments, p is 4. In some embodiments, p is 8.

Also provided herein are antibodies or antigen-binding fragments thereof that specifically bind to the human PD-L1 protein, wherein the antibody includes heavy chain CDR sequences of SEQ ID NOs: 3-5 and light chain CDR sequences of SEQ ID NOs: 6-8, wherein the antibody includes one or more amino acid substitutions within one or more of the CDRs.

In some embodiments, the antibody exhibits a binding affinity to the human PD-L1 protein that is between 3 and 300 nM. In some embodiments, the antibody exhibits a binding affinity to the human PD-L1 protein that is between 3 and 15 nM.

In some embodiments, the antibody further exhibits a total internalization that is higher than the total internaliza- In some embodiments, the antibody includes heavy chain CDR sequences of SEQ ID NOs: 13-15 and light chain CDR sequences of SEQ ID NOs: 16-18. In some embodiments, the antibody includes a heavy chain variable region sequence having at least 80% sequence identity to SEQ ID NO: 11 and a light chain variable region sequence having at least 80% sequence identity to SEQ ID NO: 12. In some embodiments, the antibody includes a heavy chain variable region sequence having at least 90% sequence identity to SEQ ID NO: 11 and a light chain variable region sequence having at least 90% sequence identity to SEQ ID NO: 12. In some embodiments, the antibody includes a heavy chain variable region sequence having at least 95% sequence identity to SEQ ID NO: 11 and a light chain variable region sequence having at least 95% sequence identity to SEQ ID NO: 12. In some embodiments, the antibody includes a heavy chain variable region sequence of SEQ ID NO: 11 and a light chain variable region sequence of SEQ ID NO: 12.

In some embodiments, the antibody includes the heavy chain sequence of SEQ ID NO: 9 and the light chain sequence of SEQ ID NO: 10.

In some embodiments, the fragment is a Fab, Fab', F(ab')2, Fab'-SH, Fv, diabody, linear antibody, or single-chain antibody fragment.

In some embodiments, the antibody contains L234A and L235A mutations in the heavy chain of the antibody.

In some embodiments, the heavy chain constant region is of the IgG1 isotype.

In some embodiments, the antibody is a humanized or chimeric antibody.

In some embodiments, the antibody is conjugated to a cytotoxic agent via a linker. In some embodiments, the antibody is conjugated to monomethyl auristatin E (MMAE). In some embodiments, the antibody is conjugated to MMAE via an enzyme-cleavable linker unit. In some embodiments, the enzyme-cleavable linker unit includes a Val-Cit linker. In some embodiments, the antibody is conjugated to MMAE via a linker forming an antibody-drug conjugate having the structure:

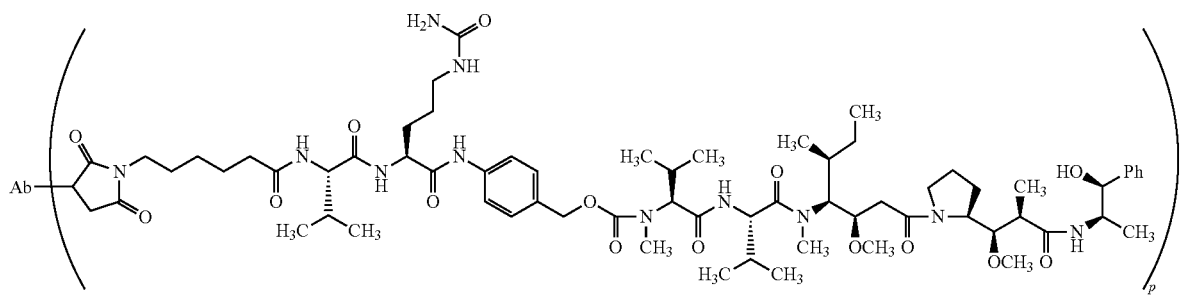

where Ab represents the antibody and p ranges from 2 to 10. In some embodiments, p is 4. In some embodiments, p is 8.

In some embodiments, the antibody is conjugated to camptothecin. In some embodiments, the antibody is conjugated to camptothecin via an enzyme-cleavable linker unit. In some embodiments, the enzyme-cleavable linker unit includes a Val-Lys-Gly linker. In some embodiments, the antibody is conjugated to camptothecin via a linker forming an antibody-drug conjugate having the structure:

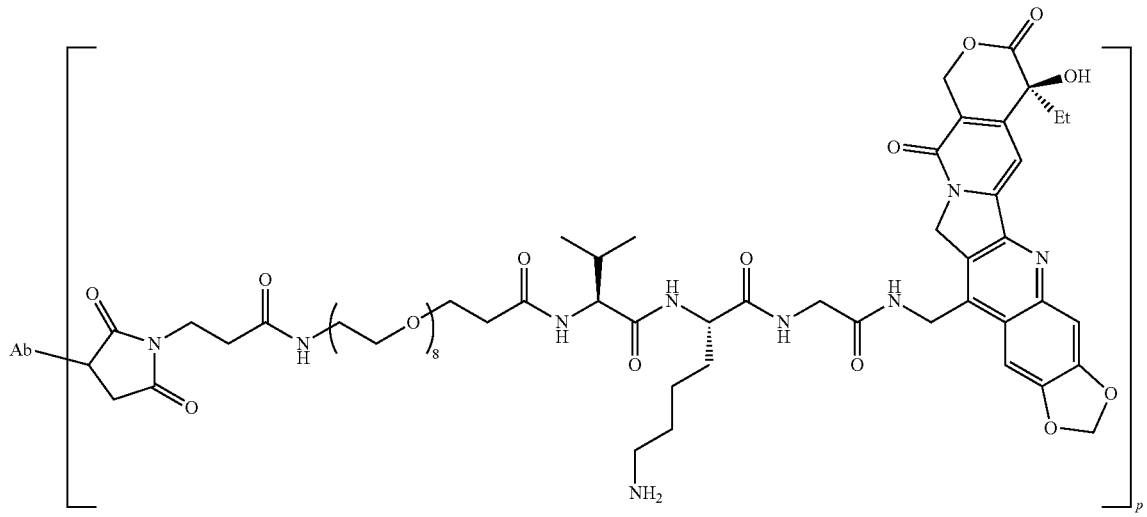

where Ab represents the antibody and p ranges from 2 to 10. In some embodiments, p is 4. In some embodiments, p is 8.

Also provided herein are antibodies or antigen-binding fragments thereof that specifically bind to the human PD-L1 protein, where the antibody includes heavy chain CDR sequences of SEQ ID NOs: 13-15 and light chain CDR sequences of SEQ ID NOs: 16-18.

In some embodiments, the antibody exhibits a binding affinity to the human PD-L1 protein that is between 3 and 300 nM. In some embodiments, the antibody exhibits a binding affinity to the human PD-L1 protein that is between 3 and 15 nM.

In some embodiments, the antibody further exhibits a total internalization that is higher than the total internalization of Ab1. In some embodiments, the total internalization is between a 9% and 155% increase of AUC over the AUC of Ab1. In some embodiments, the total internalization is determined by a FabFluor internalization assay.

In some embodiments, the antibody further exhibits an x50 that is higher than the x50 of Ab1.

In some embodiments, the antibody is conjugated to monomethyl auristatin E (MMAE), and where the x50 is between 3 ng/mL and 20 ng/mL in an MDA-MB-231 cell line.

In some embodiments, the antibody is conjugated to camptothecin, and where the x50 is between 15 ng/mL and 55 ng/mL in an MDA-MB-231 cell line.

In some embodiments, the antibody includes a heavy chain variable region sequence having at least 80% sequence identity to SEQ ID NO: 11 and a light chain variable region sequence having at least 80% sequence identity to SEQ ID NO: 12. In some embodiments, the antibody includes a heavy chain variable region sequence having at least 90% sequence identity to SEQ ID NO: 11 and a light chain variable region sequence having at least 90% sequence identity to SEQ ID NO: 12. In some embodiments, the antibody includes a heavy chain variable region sequence having at least 95% sequence identity to SEQ ID NO: 11 and a light chain variable region sequence having at least 95% sequence identity to SEQ ID NO: 12. In some embodiments, the antibody includes a heavy chain variable region sequence of SEQ ID NO: 11 and a light chain variable region sequence of SEQ ID NO: 12.

In some embodiments, the antibody includes the heavy chain sequence of SEQ ID NO: 9 and the light chain sequence of SEQ ID NO: 10.

In some embodiments, the fragment is a Fab, Fab', F(ab')$_2$, Fab'-SH, Fv, diabody, linear antibody, or single-chain antibody fragment.

In some embodiments, the antibody contains L234A and L235A mutations in the heavy chain of the antibody.

In some embodiments, the heavy chain constant region is of the IgG1 isotype.

In some embodiments, the antibody is a humanized or chimeric antibody.

In some embodiments, the antibody is conjugated to a cytotoxic agent via a linker. In some embodiments, the antibody is conjugated to monomethyl auristatin E (MMAE). In some embodiments, the antibody is conjugated to MMAE via an enzyme-cleavable linker unit. In some embodiments, the enzyme-cleavable linker unit includes a Val-Cit linker. In some embodiments, the antibody is conjugated to MMAE via a linker forming an antibody-drug conjugate having the structure:

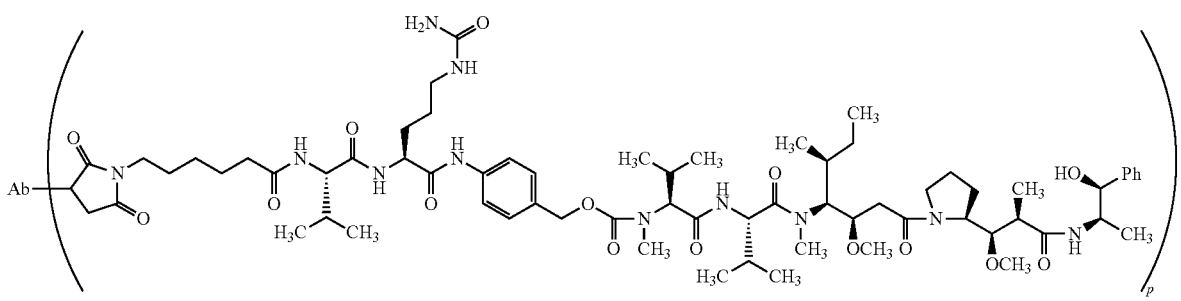

where Ab represents the antibody and p ranges from 2 to 10. In some embodiments, p is 4. In some embodiments, p is 8.

In some embodiments, the antibody is conjugated to camptothecin. In some embodiments, the antibody is conjugated to camptothecin via an enzyme-cleavable linker unit. In some embodiments, the enzyme-cleavable linker unit includes a Val-Lys-Gly linker. In some embodiments, the antibody is conjugated to camptothecin via a linker forming an antibody-drug conjugate having the structure:

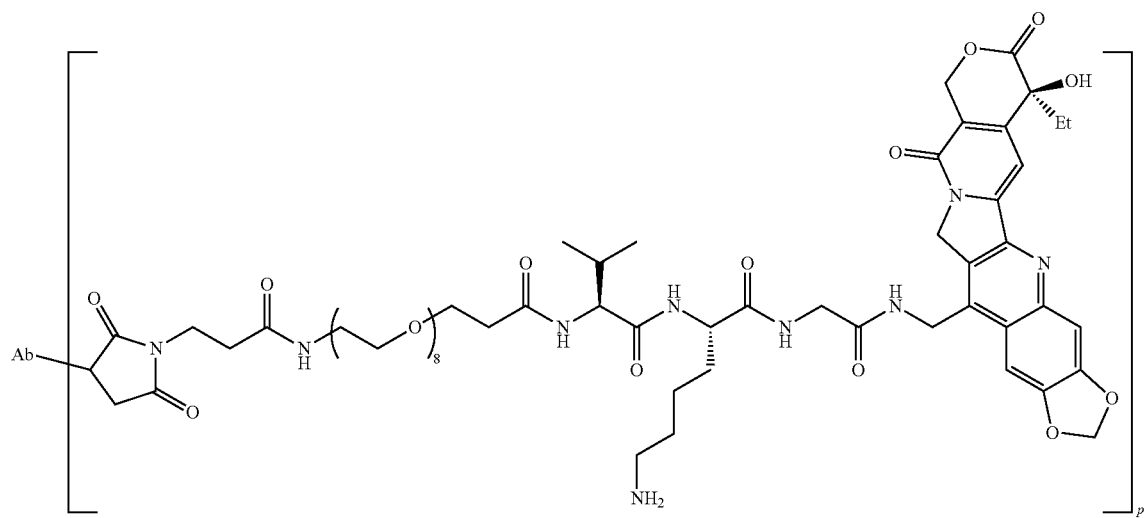

where Ab represents the antibody and p ranges from 2 to 10. In some embodiments, p is 4. In some embodiments, p is 8.

Also provided herein are antibodies or antigen-binding fragments thereof that specifically bind to the human PD-L1 protein, where the antibody is conjugated to camptothecin forming an antibody-drug conjugate, where the antibody-drug conjugate has the structure:

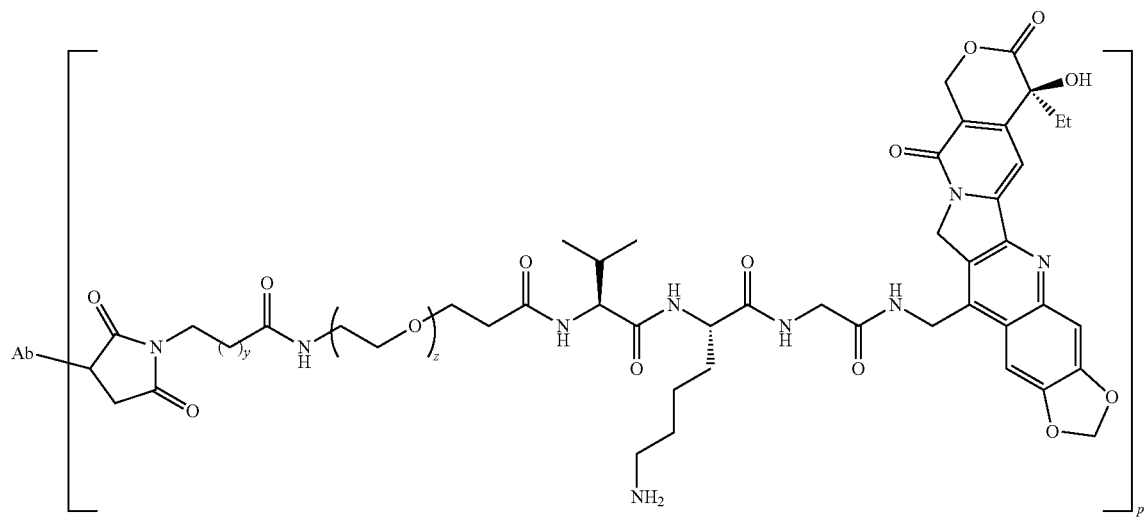

where Ab is an anti-PD-L1 antibody; y is 1, 2, 3, or 4, or is 1 or 4; and z is an integer from 2 to 12, or is 2, 4, 8, or 12; and p is 1-16.

In some embodiments, the antibody-drug conjugate has the structure:

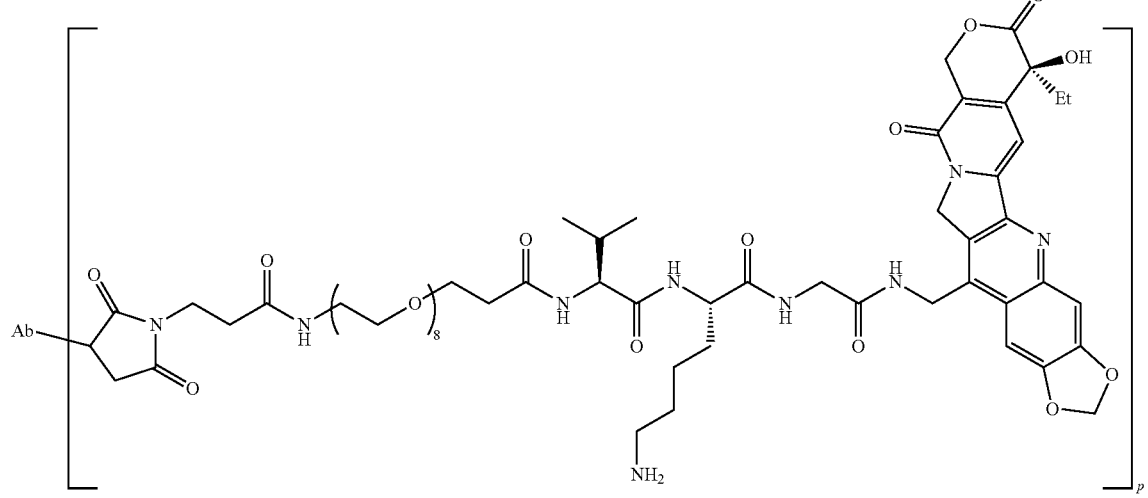

In some embodiments, p ranges from 2 to 10.

Also provided herein are antibodies or antigen-binding fragments thereof that specifically bind to the human Programmed Death-Ligand 1 (PD-L1) protein, wherein the antibody exhibits a binding affinity to the human PD-L1 protein that is greater than that of Ab1. In some embodiments, the antibody exhibits a binding affinity that is greater than 2.7 nM.

Also provided herein are antibodies or antigen-binding fragments thereof that specifically bind to the human Programmed Death-Ligand 1 (PD-L1) protein, wherein the antibody exhibits a $k_{assoc}$ to the human PD-L1 protein that is less than that of Ab1. In some embodiments, the antibody exhibits a $k_{assoc}$ to the human PD-L1 protein that is less than $5 \times 10^5$ $M^{-1}s^{-1}$.

Also provided herein are antibodies or antigen-binding fragments thereof that specifically bind to the human Programmed Death-Ligand 1 (PD-L1) protein, wherein the antibody exhibits a $k_{dissoc}$ to the human PD-L1 protein that is greater than that of Ab1. In some embodiments, the antibody exhibits a $k_{dissoc}$ to the human PD-L1 protein that is greater than $2 \times 10^3$ $s^{-1}$.

Also provided herein are antibody-drug conjugates including an antibody or antigen-binding fragment thereof that specifically binds to the human PD-L1 protein, where the antibody includes heavy chain CDR sequences of SEQ ID NOs: 3-5 and light chain CDR sequences of SEQ ID NOs: 6-8, where the antibody includes one or more amino acid substitutions within one or more of the CDRs, and where the antibody exhibits a binding affinity to the human PD-L1 protein that is between 5 nM and 15 nM, and where the antibody is conjugated to MMAE.

Also provided herein are antibody-drug conjugates including an antibody or antigen-binding fragment thereof that specifically binds to the human PD-L1 protein, where the antibody includes heavy chain CDR sequences of SEQ ID NOs: 3-5 and light chain CDR sequences of SEQ ID NOs: 6-8, where the antibody includes one or more amino acid substitutions within one or more of the CDRs, and where the antibody exhibits a binding affinity to the human PD-L1 protein that is between 5 nM and 15 nM, and where the antibody is conjugated to camptothecin.

Also provided herein are pharmaceutical compositions that include a therapeutically effective amount of the antibodies describes described herein and a pharmaceutically acceptable excipient.

Also provided herein are methods of treating cancer in a subject, including administering to the subject any of the antibodies described herein. In some embodiments, the subject is a human subject. In some embodiments, the cancer is melanoma, non-small cell lung cancer (NSCLC), small cell lung cancer (SCLC), head and neck cancer, triple negative breast cancer (TNBC), ovarian cancer, urothelial cancer, hepatocellular carcinoma (HCC), gastric cancer, or cervical cancer.

Also provided herein are nucleic acid encoding any of the antibodies described herein.

Also provided herein are vectors including any of the nucleic acids described herein.

Also provided herein are any of the host cells described herein that include any of the nucleic acids described herein. In some embodiments, the host cell is a Chinese hamster ovary (CHO) cell.

Also provided herein are methods of producing an antibody or antigen-binding fragment thereof that specifically binds to the human PD-L1 protein, including culturing any of the host cells described herein under a condition suitable for production of the antibody.

Also provided herein are methods of producing an antibody drug-conjugate that specifically binds to the human PD-L1 protein, including culturing any of the host cells described herein under a condition suitable for production of the antibody; and conjugating the antibody to a cytotoxic agent. In some embodiments, the cytotoxic agent is MMAE or camptothecin.

Also provided herein is the use of any of the anti-PD-L1 antibodies or any of the antibody drug conjugates described herein for use in the manufacture of a medicament for the treatment of cancer (e.g., a cancer associated with PD-L1+ expression).

Also provided herein are anti-PD-L1 antibodies described herein or antibody drug conjugates described herein for use in the treatment of cancer (e.g., a cancer associated with PD-L1$^+$ expression).

Also provided herein are anti-PD-L1 antibodies described herein or antibody drug conjugates described herein for use in medicine.

Also provided herein are methods of killing a PD-L1$^+$ cell in a subject in need thereof, the method comprising administering to the subject a therapeutically effective amount of any of the anti-PD-L1 antibodies described herein or any of the antibody drug conjugates described herein.

Also provided herein is the use of any of the anti-PD-L1 antibodies described herein or any of the antibody drug conjugates described herein for use in the manufacture of a medicament for killing a PD-L1$^+$ cell in a subject in need thereof.

Also provided herein are methods of reducing the volume of a solid tumor (e.g., a PD-L1$^+$ solid tumor) in a subject that comprises administering to the subject a therapeutically effective amount of any of the anti-PD-L1 antibodies described herein or any of the antibody drug conjugates described herein.

Also provided herein is the use of any of the anti-PD-L1 antibodies described herein or any of the antibody drug conjugates described herein for use in the manufacture of a medicament for reducing the volume of a solid tumor (e.g., a PD-L1$^+$ solid tumor) in a subject.

DETAILED DESCRIPTION

I. Definitions

Figure 1:
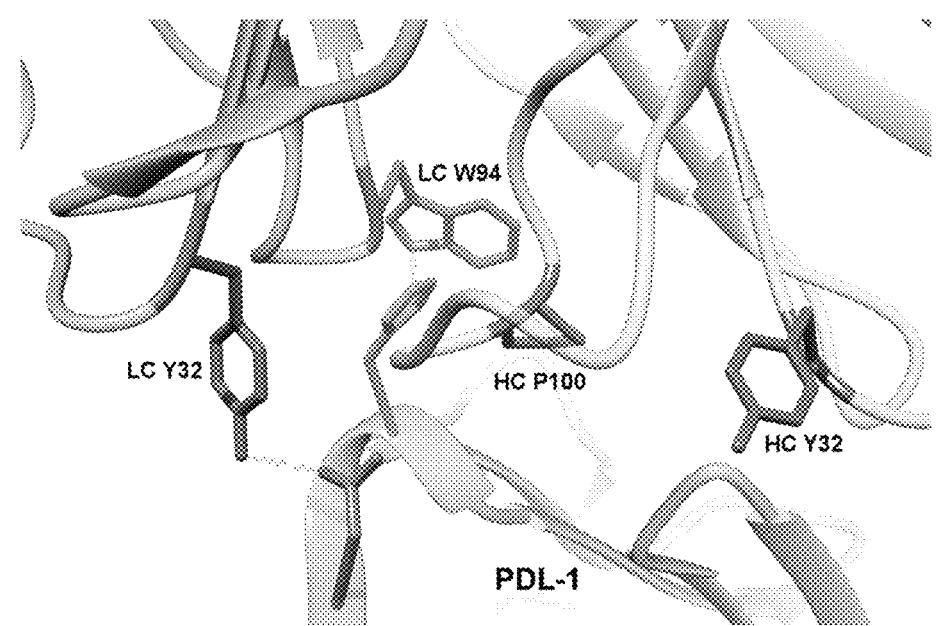
FIG. 1 shows example amino acid residues of Ab1 selected for mutation.
Figure 2A:
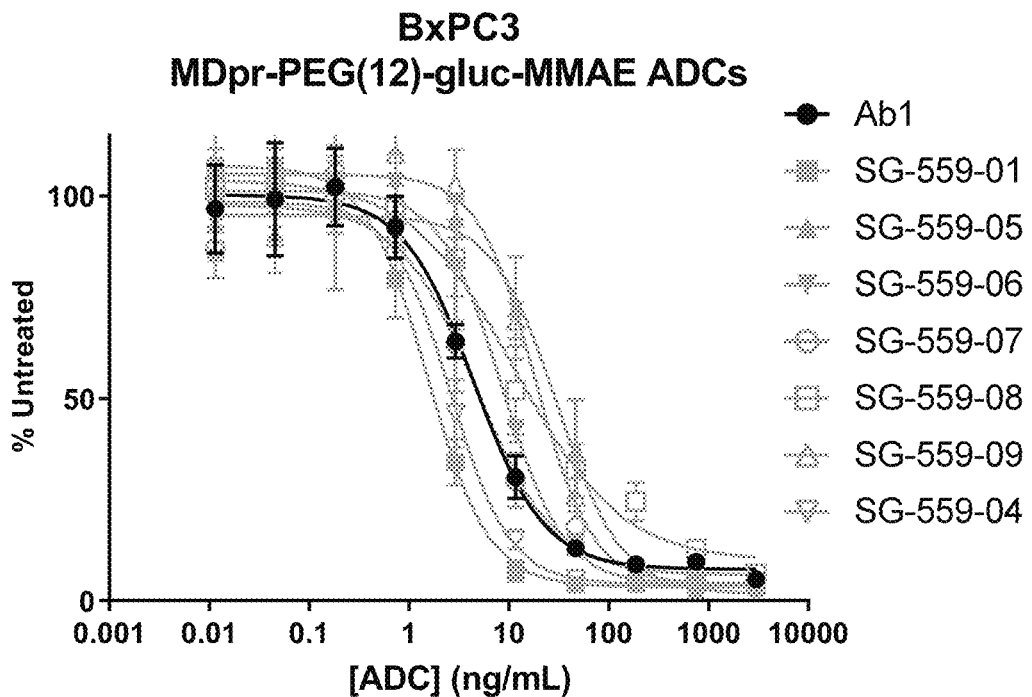
FIGS. 2A-2F shows cytotoxicity of SG-559-xx ADCs in several cell lines.
Figure 2B:
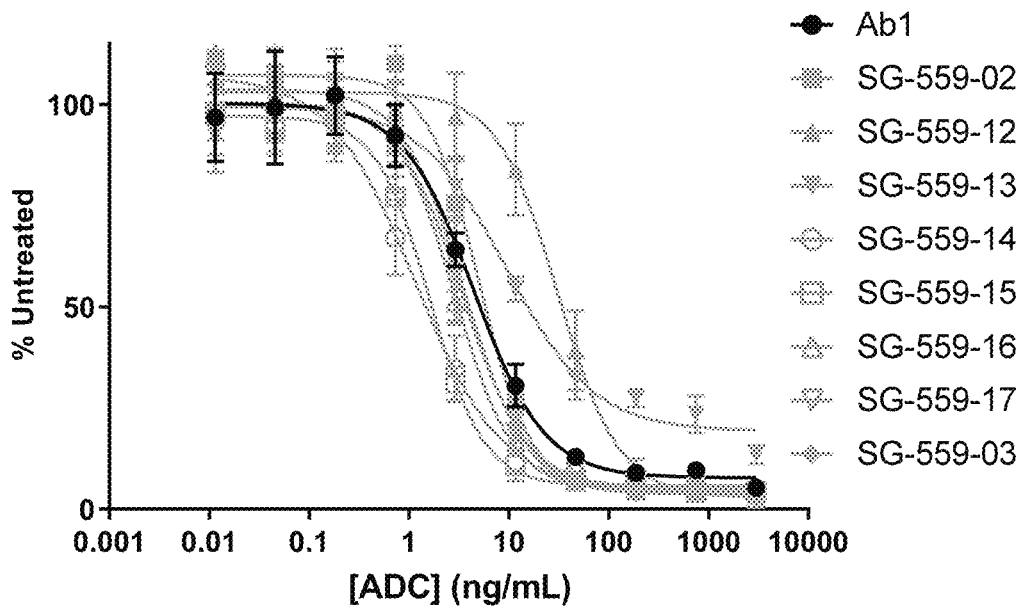
Figure 2C:
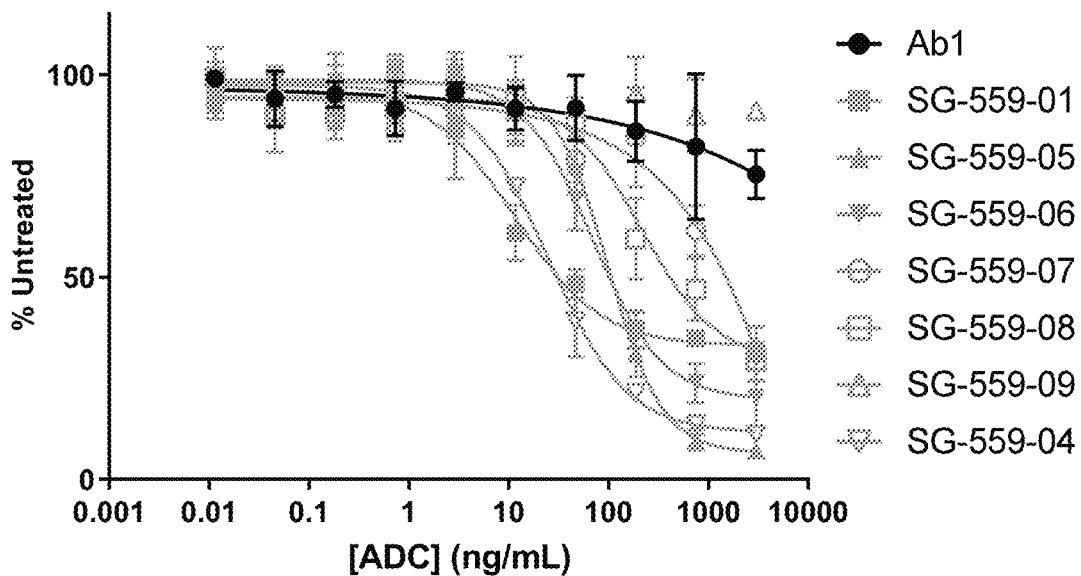
Figure 2D:
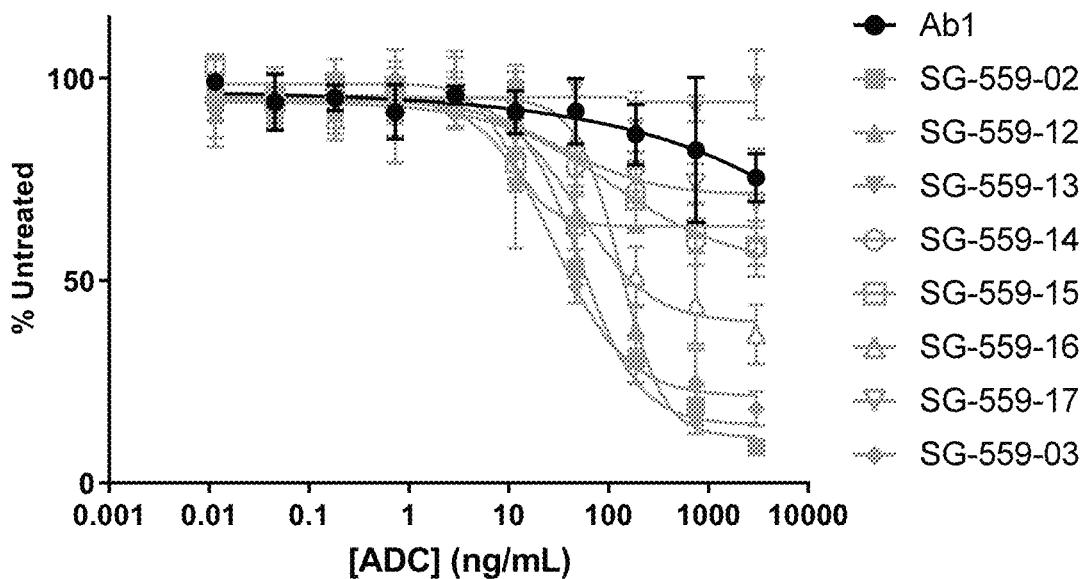
Figure 2E:
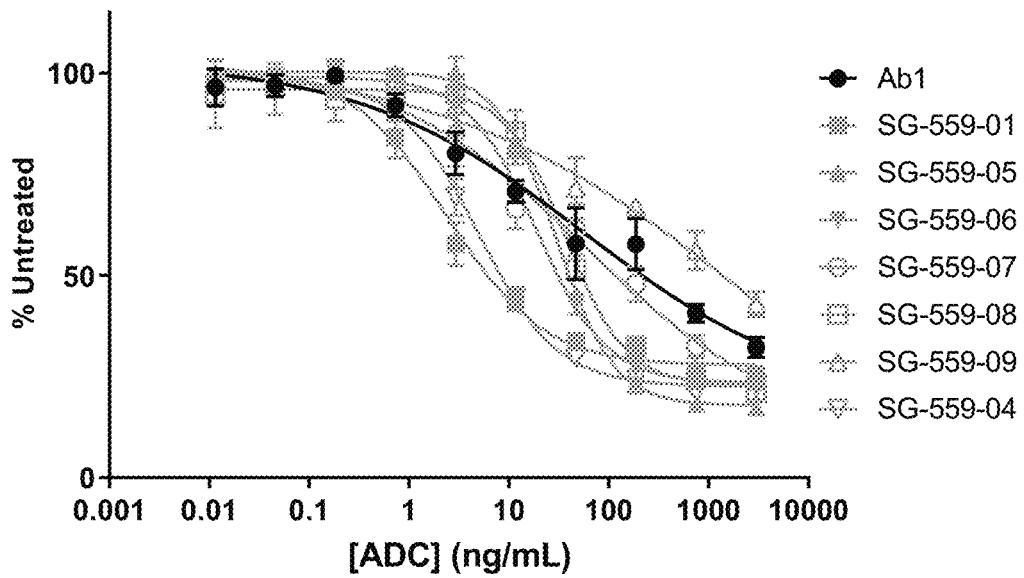
Figure 2F:
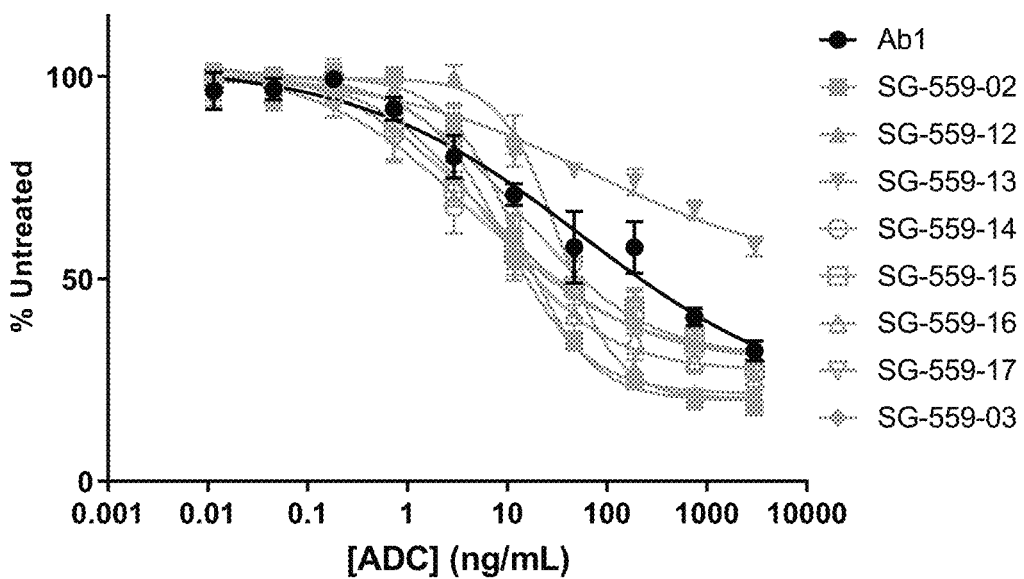

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that aspects and embodiments of the invention described herein include "comprising," "consisting," and "consisting essentially of" aspects and embodiments.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The terms "PD-L1," "CD274," "B7-H1," and "programmed cell death ligand 1" are used interchangeably herein, and, unless specified otherwise, include any variants, isoforms and species homologs of human PD-L1 which are generally expressed by cells or expressed on cells transfected with the PD-L1 gene.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as V$_H$ or VH) and a heavy chain constant region (C$_H$ or CH). The heavy chain constant region typically is comprised of three domains, C$_H$1, C$_H$2, and C$_H$3. The heavy chains are generally inter-connected via disulfide bonds in the so-called "hinge region." Each light chain typically is comprised of a light chain variable region (abbreviated herein as V$_L$ or VL) and a light chain constant region (C$_L$ or CL). The light chain constant region typically is comprised of one domain, C$_L$. The CL can be of κ (kappa) or λ (lambda) isotype. The terms "constant domain" and "constant region" are used interchangeably herein. An immunoglobulin can derive from any of the commonly known isotypes, including but not limited to IgA, secretory IgA, IgG, and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody may be further subdivided into regions of hypervariability (or hypervariable regions, which may be hypervariable in sequence and/or form of structurally defined loops), also termed complementarity-determining regions (CDRs), interspersed with regions that are more conserved, termed framework regions (FRs). The terms "complementarity determining regions" and "CDRs," synonymous with "hypervariable regions" or "HVRs" are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). Within each $V_H$ and $V_L$, three CDRs and four FRs are typically arranged from amino-terminus to carboxy-terminus in the following order: FR1, CDR1, FR2, CDR2, FR3, CDR3, FR4 (See also Chothia and Lesk *J. Mol. Biol.*, 195, 901-917 (1987)).

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half-life of significant periods of time, such as at least about 30 min, at least about 45 min, at least about one hour (h), at least about two hours, at least about four hours, at least about eight hours, at least about 12 hours (h), about 24 hours or more, about 48 hours or more, about three, four, five, six, seven or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An antibody may also be a bispecific antibody, diabody, multispecific antibody or similar molecule.

The term "monoclonal antibody" as used herein refers to a preparation of antibody molecules that are recombinantly produced with a single primary amino acid sequence. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

An "isolated antibody" refers to an antibody that is substantially free of other antibodies having different antigenic specificities (e.g., an isolated antibody that binds specifically to PD-L1 is substantially free of antibodies that bind specifically to antigens other than PD-L1). An isolated antibody that binds specifically to PD-L1 can, however, have cross-reactivity to other antigens, such as PD-L1 molecules from different species. Moreover, an isolated antibody can be substantially free of other cellular material and/or chemicals. In one embodiment, an isolated antibody includes an antibody conjugate attached to another agent (e.g., small molecule drug). In some embodiments, an isolated anti-PD-L1 antibody includes a conjugate of an anti-PD-L1 antibody with a small molecule drug (e.g., MMAE or MMAF).

A "human antibody" (HuMAb) refers to an antibody having variable regions in which both the FRs and CDRs are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibodies" and "fully human antibodies" and are used synonymously.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generic for different kinds of modifications of antibodies, and which is a well-known process for the skilled person. In particular, a chimeric antibody may be generated by using standard DNA techniques as described in Sambrook et al., 1989, Molecular Cloning: A laboratory Manual, New York: Cold Spring Harbor Laboratory Press, Ch. 15. Thus, the chimeric antibody may be a genetically or an enzymatically engineered recombinant antibody. It is within the knowledge of the skilled person to generate a chimeric antibody, and thus, generation of the chimeric antibody according to the present invention may be performed by other methods than described herein. Chimeric monoclonal antibodies for therapeutic applications are developed to reduce antibody immunogenicity. They may typically contain non-human (e.g. murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

An "anti-antigen antibody" refers to an antibody that binds to the antigen. For example, an anti-PD-L1 antibody is an antibody that binds to the antigen PD-L1.

An "antigen-binding portion" or antigen-binding fragment" of an antibody refers to one or more fragments of an antibody that retain the ability to bind specifically to the antigen bound by the whole antibody. Examples of antibody fragments (e.g., antigen-binding fragment) include but are not limited to Fv, Fab, Fab', Fab'-SH, F(ab')$_2$; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Percent (%) sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % sequence identity of a given amino acid sequence A to, with, or against a given amino acid sequence B (which can alternatively be phrased as a given amino acid sequence A that has or comprises a certain % sequence identity to, with, or against a given amino acid sequence B) is calculated as follows:

100 times the fraction $X/Y$ where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % sequence identity of A to B will not equal the % sequence identity of B to A.

As used herein, the terms "binding", "binds" or "specifically binds" in the context of the binding of an antibody to a pre-determined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ of binding to a non-specific antigen (e.g., BSA, casein) other than the predetermined antigen or a closely related antigen. The amount with which the $K_D$ of binding is lower is dependent on the $K_D$ of the antibody, so that when the $K_D$ of the antibody is very low, then the amount with which the $K_D$ of binding to the antigen is lower than the $K_D$ of binding to a non-specific antigen may be at least 10,000-fold (that is, the antibody is highly specific).

The term "$K_D$" (M), as used herein, refers to the dissociation equilibrium constant of a particular antibody-antigen interaction. Affinity, as used herein, and $K_D$ are inversely related, that is that higher affinity is intended to refer to lower $K_D$, and lower affinity is intended to refer to higher $K_D$.

The term "ADC" refers to an antibody-drug conjugate, which in the context of the present invention refers to an anti-PD-L1 antibody, which is coupled to a drug moiety (e.g., MMAE or MMAF) as described in the present application.

The abbreviations "vc" and "val-cit" refer to the dipeptide linker valine-citrulline.

The abbreviation VKG refers to the tripeptide linker valine-lysine-glycine.

The abbreviation "MC" refers to the stretcher maleimidocaproyl:

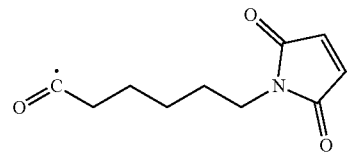

The abbreviation "MP" refers to the stretcher maleimidopropionyl:

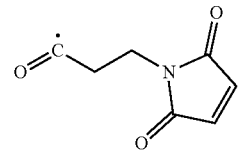

"PEG Unit" as used herein is an organic moiety comprised of repeating ethylene-oxy subunits (PEGs or PEG subunits) and may be polydisperse, monodisperse or discrete (i.e., having discrete number of ethylene-oxy subunits). Polydisperse PEGs are a heterogeneous mixture of sizes and molecular weights whereas monodisperse PEGs are typically purified from heterogeneous mixtures and are therefore provide a single chain length and molecular weight. Preferred PEG Units comprises discrete PEGs, compounds that are synthesized in step-wise fashion and not via a polymerization process. Discrete PEGs provide a single molecule with defined and specified chain length.

The PEG Unit provided herein comprises one or multiple polyethylene glycol chains, each comprised of one or more ethyleneoxy subunits, covalently attached to each other. The polyethylene glycol chains can be linked together, for example, in a linear, branched or star shaped configuration. Typically, at least one of the polyethylene glycol chains prior to incorporation into a camptothecin conjugate is derivatized at one end with an alkyl moiety substituted with an electrophilic group for covalent attachment to the carbamate nitrogen of a methylene carbamate unit (i.e., represents an instance of R). Typically, the terminal ethyleneoxy subunit in each polyethylene glycol chains not involved in covalent attachment to the remainder of the Linker Unit is modified with a PEG Capping Unit, typically an optionally substituted alkyl such as —$CH_3$, $CH_2CH_3$ or $CH_2CH_2CO_2H$. A preferred PEG Unit has a single polyethylene glycol chain with 2 to 24 —$CH_2CH_2O$— subunits covalently attached in series and terminated at one end with a PEG Capping Unit.

A "cancer" refers to a broad group of various diseases characterized by the uncontrolled growth of abnormal cells in the body. A "cancer" or "cancer tissue" can include a tumor. Unregulated cell division and growth results in the formation of malignant tumors that invade neighboring tissues and can also metastasize to distant parts of the body through the lymphatic system or bloodstream. Following metastasis, the distal tumors can be said to be "derived from" the pre-metastasis tumor.

The term "antibody-dependent cellular cytotoxicity", or ADCC, is a mechanism for inducing cell death that depends upon the interaction of antibody-coated target cells with immune cells possessing lytic activity (also referred to as effector cells). Such effector cells include natural killer cells, monocytes/macrophages and neutrophils. The effector cells attach to an Fc effector domain(s) of Ig bound to target cells via their antigen-combining sites. Death of the antibody-coated target cell occurs as a result of effector cell activity.

The term "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an Fc effector domain(s) of Ig.

The term "complement-dependent cytotoxicity", or CDC, refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

"Treatment" or "therapy" of a subject refers to any type of intervention or process performed on, or the administration of an active agent to, the subject with the objective of reversing, alleviating, ameliorating, inhibiting, slowing down, or preventing the onset, progression, development, severity, or recurrence of a symptom, complication, condition, or biochemical indicia associated with a disease. In some embodiments, the disease is cancer.

A "subject" includes any human or non-human animal. The term "non-human animal" includes, but is not limited to, vertebrates such as non-human primates, sheep, dogs, and rodents such as mice, rats, and guinea pigs. In some embodiments, the subject is a human. The terms "subject" and "patient" and "individual" are used interchangeably herein.

An "effective amount" or "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example for the treatment of tumors, a therapeutically effective amount of an anti-cancer agent inhibits cell growth or tumor growth by at least about 10%, by at least about 20%, by at least about 30%, by at least about 40%, by at least about 50%, by at least about 60%, by at least about 70%, or by at least about 80%, by at least about 90%, by at least about 95%, by at least about 96%, by at least about 97%, by at least about 98%, or by at least about 99% in a treated subject(s) (e.g., one or more treated subjects) relative to an untreated subject(s) (e.g., one or more untreated subjects). In some embodiments, a therapeutically effective amount of an anti-cancer agent inhibits cell growth or tumor growth by 100% in a treated subject(s) (e.g., one or more treated subjects) relative to an untreated subject(s) (e.g., one or more untreated subjects).

In other embodiments of the disclosure, tumor regression can be observed and continue for a period of at least about 20 days, at least about 30 days, at least about 40 days, at least about 50 days, or at least about 60 days.

A therapeutically effective amount of a drug (e.g., anti-PD-L1 antibody-drug conjugate) includes a "prophylactically effective amount," which is any amount of the drug that, when administered alone or in combination with an anti-cancer agent to a subject at risk of developing a cancer (e.g., a subject having a pre-malignant condition) or of suffering a recurrence of cancer, inhibits the development or recurrence of the cancer. In some embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

As used herein, "subtherapeutic dose" means a dose of a therapeutic compound (e.g., an anti-PD-L1 antibody-drug conjugate) that is lower than the usual or typical dose of the therapeutic compound when administered alone for the treatment of a hyperproliferative disease (e.g., cancer).

An "immune-related response pattern" refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

By way of example, an "anti-cancer agent" promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-cancer agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity or other adverse physiological effects at the cellular, organ and/or organism level (adverse effects) resulting from administration of the drug.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration that is at least the same as the treatment duration, or at least 1.5, 2.0, 2.5, or 3 times longer than the treatment duration.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progression free survival" or "PFS" refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" or "ORR" refers to the sum of complete response (CR) rate and partial response (PR) rate.

As used herein, "overall survival" or "OS" refers to the percentage of individuals in a group who are likely to be alive after a particular duration of time.

The phrase "pharmaceutically acceptable" indicates that the substance or composition must be compatible chemically and/or toxicologically, with the other ingredients comprising a formulation, and/or the mammal being treated therewith.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 4,4'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Administering" or "administration" refer to the physical introduction of a therapeutic agent to a subject, using any of the various methods and delivery systems known to those skilled in the art. Exemplary routes of administration for the anti-PD-L1 antibody-drug conjugate include intravenous, intramuscular, subcutaneous, intraperitoneal, spinal or other parenteral routes of administration, for example by injection or infusion (e.g., intravenous infusion). The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A therapeutic agent can be administered via a non-parenteral route, or orally. Other non-parenteral routes include a topical, epidermal or mucosal route of administration, for example, intranasally, vaginally, rectally, sublingually or topically. Administration can also be performed, for example, once, a plurality of times, and/or over one or more extended periods.

The terms "baseline" or "baseline value" used interchangeably herein can refer to a measurement or characterization of a symptom before the administration of the therapy (e.g., an anti-PD-L1 antibody-drug conjugate as described herein) or at the beginning of administration of the therapy. The baseline value can be compared to a reference value in order to determine the reduction or improvement of a symptom of a PD-L1-associated disease contemplated herein (e.g., cancer). The terms "reference" or "reference value" used interchangeably herein can refer to a measurement or characterization of a symptom after administration of the therapy (e.g., an anti-PD-L1 antibody-drug conjugate as described). The reference value can be measured one or more times during a dosage regimen or treatment cycle or at the completion of the dosage regimen or treatment cycle. A "reference value" can be an absolute value; a relative value; a value that has an upper and/or lower limit; a range of values; an average value; a median value: a mean value; or a value as compared to a baseline value.

Similarly, a "baseline value" can be an absolute value; a relative value; a value that has an upper and/or lower limit; a range of values; an average value; a median value; a mean value; or a value as compared to a reference value. The reference value and/or baseline value can be obtained from one individual, from two different individuals or from a group of individuals (e.g., a group of two, three, four, five or more individuals).

The term "monotherapy" as used herein means that the anti-PD-L1 antibody-drug conjugate is the only anti-cancer agent administered to the subject during the treatment cycle. Other therapeutic agents, however, can be administered to the subject. For example, anti-inflammatory agents or other agents administered to a subject with cancer to treat symptoms associated with cancer, but not the underlying cancer itself, including, for example inflammation, pain, weight loss, and general malaise, can be administered during the period of monotherapy.

An "adverse event" (AE) as used herein is any unfavorable and generally unintended or undesirable sign (including an abnormal laboratory finding), symptom, or disease associated with the use of a medical treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

A "serious adverse event" or "SAE" as used herein is an adverse event that meets one of the following criteria:

Is fatal or life-threatening (as used in the definition of a serious adverse event, "life-threatening" refers to an event in which the patient was at risk of death at the time of the event; it does not refer to an event which hypothetically might have caused death if it was more severe.

Results in persistent or significant disability/incapacity

Constitutes a congenital anomaly/birth defect

Is medically significant, i.e., defined as an event that jeopardizes the patient or may require medical or surgical intervention to prevent one of the outcomes listed above. Medical and scientific judgment must be exercised in deciding whether an AE is "medically significant"

Requires inpatient hospitalization or prolongation of existing hospitalization, excluding the following: 1) routine treatment or monitoring of the underlying disease, not associated with any deterioration in condition; 2) elective or pre-planned treatment for a pre-existing condition that is unrelated to the indication under study and has not worsened since signing the informed consent; and 3) social reasons and respite care in the absence of any deterioration in the patient's general condition.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

Reference to "about" a value or parameter herein includes (and describes) embodiments that are directed to that value or parameter per se. For example, description referring to "about X" encompasses and describes "X."

As described herein, any concentration range, percentage range, ratio range, or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

II. General

The invention provides antibodies and ADCs that specifically bind PD-L1 The present invention is based, in part, on the discovery that antibody-drug conjugates, including MMAE antibody-drug conjugates and camptothecin anybody-drug conjugates, targeted to PD-L1 are particularly effective at killing PD-L1+ expressing cells. PD-L1 has been shown to be expressed in a variety of cancers, including melanoma, non-small cell lung cancer (NSCLC), small cell lung cancer (SCLC), head and neck cancer, triple negative breast cancer (TNBC), ovarian cancer, urothelial cancer, hepatocellular carcinoma (HCC), gastric cancer, and cervical cancer.

III. Target Molecules

Unless otherwise indicated, PD-L1 refers to human PD-L1. An exemplary human protein sequence is assigned UniProt ID NO. Q9NZQ7.

IV. Antibodies of the Invention

Previously, select antibodies already being used to treat cancer have been conjugated, without sequence modification, to cytotoxic agents to produce antibody-drug conjugates (ADCs). These ADCs have often proven as effective or more effective than the unconjugated antibody at killing tumor cells. Previously, if modifications to the antibody were contemplated during the process of preparing an ADC, some possible modifications were to increase binding affinity of the antibody or increase antibody action such as ADCC. However, it has been discovered that at least in some situations, modifying or tuning an ADC antibody by, for example, reducing its binding affinity or decreasing its ADCC activity, results in improving the effectiveness of the ADC compared to an ADC with the unmodified antibody. Some examples of this include ADCs with anti-PD-L1 antibodies (such as Ab1), which are surprisingly optimized by modifying the antibodies e.g., reducing their binding affinities. For example, in some cases an anti-PD-L1 ADC is more effective at killing tumor cells in vitro when the binding affinity of the antibody conjugated to a cytotoxic agent is reduced. In another example, in some cases an anti-PD-L1 ADC is more effective at killing tumor cells in vitro and in vivo when the binding affinity of the antibody conjugated to a cytotoxic agent is reduced.

The invention provides antibodies, such as humanized antibodies, that bind PD-L1 with binding affinities between 3 nM and 300 nM. In some embodiments, the antibodies described herein can bind to PD-L1 with a $K_D$ of between about 3 nM and 300 nM (e.g., about 3 nM to about 275 nM, about 3 nM to about 250 nM, about 3 nM to about 225 nM, about 3 nM to about 200 nM, about 3 nM to about 175 nM, about 3 nM to about 150 nM, about 3 nM to about 125 nM, about 3 nM to about 100 nM, about 3 nM to about 90 nM, about 3 nM to about 80 nM, about 3 nM to about 70 nM, about 3 nM to about 60 nM, about 3 nM to about 50 nM, about 3 nM to about 40 nM, about 3 nM to about 30 nM, about 3 nM to about 20 nM, about 3 nM to about 10 nM, about 10 nM to about 300 nM, about 10 nM to about 275 nM, about 10 nM to about 250 nM, about 10 nM to about 225 nM, about 10 nM to about 200 nM, about 10 nM to about 175 nM, about 10 nM to about 150 nM, about 10 nM to about 125 nM, about 10 nM to about 100 nM, about 10 nM to about 90 nM, about 10 nM to about 80 nM, about 10 nM to about 70 nM, about 10 nM to about 60 nM, about 10 nM to about 50 nM, about 10 nM to about 40 nM, about 10 nM to about 30 nM, about 10 nM to about 20 nM, about 20 nM to about 300 nM, about 20 nM to about 275 nM, about 20 nM to about 250 nM, about 20 nM to about 225 nM, about 20 nM to about 200 nM, about 20 nM to about 175 nM, about 20 nM to about 150 nM, about 20 nM to about 125 nM, about 20 nM to about 100 nM, about 20 nM to about 90 nM, about 20 nM to about 80 nM, about 20 nM to about 70 nM, about 20 nM to about 60 nM, about 20 nM to about 50 nM, about 20 nM to about 40 nM, about 20 nM to about 30 nM, about 30 nM to about 300 nM, about 30 nM to about 275 nM, about 30 nM to about 250 nM, about 30 nM to about 225 nM, about 30 nM to about 200 nM, about 30 nM to about 175 nM, about 30 nM to about 150 nM, about 30 nM to about 125 nM, about 30 nM to about 100 nM, about 30 nM to about 90 nM, about 30 nM to about 80 nM, about 30 nM to about 70 nM, about 30 nM to about 60 nM, about 30 nM to about 50 nM, about 30 nM to about 40 nM, about 40 nM to about 300 nM, about 40 nM to about 275 nM, about 40 nM to about 250 nM, about 40 nM to about 225 nM, about 40 nM to about 200 nM, about 40 nM to about 175 nM, about 40 nM to about 150 nM, about 40 nM to about 125 nM, about 40 nM to about 100 nM, about 40 nM to about 90 nM, about 40 nM to about 80 nM, about 40 nM to about 70 nM, about 40 nM to about 60 nM, about 40 nM to about 50 nM, about 50 nM to about 300 nM, about 50 nM to about 275 nM, about 50 nM to about 250 nM, about 50 nM to about 225 nM, about 50 nM to about 200 nM, about 50 nM to about 175 nM, about 50 nM to about 150 nM, about 50 nM to about 125 nM, about 50 nM to about 100 nM, about 50 nM to about 90 nM, about 50 nM to about 80 nM, about 50 nM to about 70 nM, about 50 nM to about 60 nM, about 60 nM to about 300 nM, about 60 nM to about 275 nM, about 60 nM to about 250 nM, about 60 nM to about 225 nM, about 60 nM to about 200 nM, about 60 nM to about 175 nM, about 60 nM to about 150 nM, about 60 nM to about 125 nM, about 60 nM to about 100 nM, about 60 nM to about 90 nM, about 60 nM to about 80 nM, about 60 nM to about 70 nM, about 70 nM to about 300 nM, about 70 nM to about 275 nM, about 70 nM to about 250 nM, about 70 nM to about 225 nM, about 70 nM to about 200 nM, about 70 nM to about 175 nM, about 70 nM to about 150 nM, about 70 nM to about 125 nM, about 70 nM to about 100 nM, about 70 nM to about 90 nM, about 70 nM to about 80 nM, about 80 nM to about 300 nM, about 80 nM to about 275 nM, about 80 nM to about 250 nM, about 80 nM to about 225 nM, about 80 nM to about 200 nM, about 80 nM to about 175 nM, about 80 nM to about 150 nM, about 80 nM to about 125 nM, about 80 nM to about 100 nM, about 80 nM to about 90 nM, about 90 nM to about 300 nM, about 90 nM to about 275 nM, about 90 nM to about 250 nM, about 90 nM to about 225 nM, about 90 nM to about 200 nM, about 90 nM to about 175 nM, about 90 nM to about 150 nM, about 90 nM to about 125 nM, about 90 nM to about 100 nM, about 100 nM to about 300 nM, about 100 nM to about 275 nM, about 100 nM to about 250 nM, about 100 nM to about 225 nM, about 100 nM to about 200 nM, about 100 nM to about 175 nM, about 100 nM to about 150 nM, about 100 nM to about 125 nM, about 125 nM to about 300 nM, about 125 nM to about 275 nM, about 125 nM to about 250 nM, about 125 nM to about 225 nM, about 125 nM to about 200 nM, about 125 nM to about 175 nM, about 125 nM to about 150 nM, about 150 nM to about 300 nM, about 150 nM to about 275 nM, about 150 nM to about 250 nM, about 150 nM to about 225 nM, about 150 nM to about 200 nM, about 150 nM to about 175 nM, about 175 nM to about 300 nM, about 175 nM to about 275 nM, about 175 nM to about 250 nM, about 175 nM to about 225 nM, about 175 nM to about 200 nM, about 200 nM to about 300 nM, about 200 nM to about 275 nM, about 200 nM to about 250 nM, about 200 nM to about 225 nM, about 225 nM to about 300 nM, about 225 nM to about 275 nM, about 225 nM to about 250 nM, about 250 nM to about 300 nM, about 250 nM to about 275 nM, or about 275 nM to about 30 nM) (e.g., as measured by biolayer interferometry (BLI) in phosphate buffered saline).

In some embodiments, the binding affinities are monovalent binding affinities. In some embodiments, these antibodies are point mutants of fully human anti-PD-L1 antibody Ab1. Ab1 is defined by the CDR regions of SEQ ID NOs: 3-5 and SEQ ID NOs: 6-8, the variable regions of SEQ ID NOs: 1 and 2, and the heavy and light chains of SEQ ID NOs: 86 and 87. In further embodiments, the point mutations are found in the CDR regions. In some embodiments, the point mutants exhibit reduced binding affinity and/or increased cytotoxicity and/or internalization rates as compared to Ab1. In some embodiments, the point mutants exhibit reduced binding affinity and increased cytotoxicity in vitro. In some embodiments, the point mutants exhibit reduced binding affinity and increased cytotoxicity in vivo. In some embodiments, the point mutants exhibit reduced binding affinity and increased cytotoxicity both in vitro and in vivo. In some embodiments, the point mutants exhibit reduced binding affinity and increased internalization rates in vitro. In some embodiments, the point mutants exhibit reduced binding affinity and increased internalization rates in vivo. In some embodiments, the point mutants exhibit reduced binding affinity and increased internalization rates both in vitro and in vivo.

In some embodiments, an anti-PD-L1 antibody provided herein can have one or two total amino acid substitutions in the set of six CDRs of heavy chain CDRs of SEQ ID NOs. 3-5 and light chain CDRs of SEQ ID NOs. 6-8, and binds to PD-L1 with a KD of between 3 nM and 300 nM. In some embodiments, an anti-PD-L1 antibody provided herein can have one amino acid substitution in the set of six CDRs of heavy chain CDRs of SEQ ID NOs. 3-5 and light chain CDRs of SEQ ID NOs. 6-8, and binds to PD-L1 with a KD of between 3 nM and 300 nM.

In some embodiments, an anti-PD-L1 antibody provided herein can have a heavy chain CDR1 having one amino substitution in SEQ ID NO: 3, a heavy chain CDR2 of SEQ ID NO: 4, a heavy chain CDR3 of SEQ ID NO: 5, a light chain CDR1 of SEQ ID NO: 6, a light chain CDR2 of SEQ ID NO: 7, and a light chain CDR3 of SEQ ID NO: 8, and binds to PD-L1 with a KD of between 3 nM and 300 nM. In some embodiments, the one amino acid substitution in SEQ ID NO: 3 is at amino acid position 2 of SEQ ID NO: 3. In some embodiments, the one amino acid substitution at amino acid position 2 of SEQ ID NO: 3 is a tyrosine to alanine amino acid substitution. In some embodiments, the one amino acid substitution at amino acid position 2 of SEQ ID NO: 3 is a tyrosine to serine amino acid substitution. In some embodiments, the one amino acid substitution at amino acid position 2 of SEQ ID NO: 3 is a tyrosine to glycine amino acid substitution. In some embodiments, the one amino acid substitution at amino acid position 2 of SEQ ID NO: 3 is a tyrosine to threonine amino acid substitution. In some embodiments, the one amino acid substitution at amino acid position 2 of SEQ ID NO: 3 is a tyrosine to valine amino acid substitution. In some embodiments, the one amino acid substitution at amino acid position 2 of SEQ ID NO: 3 is a tyrosine to cysteine amino acid substitution.

In some embodiments, an anti-PD-L1 antibody provided herein binds to both glycosylated and non-glycosylated PD-L1 with a $K_D$ between 3 nM and 300 nM (or any of the subrange of this range described herein).

In some embodiments, an anti-PD-L1 antibody provided herein has increased (e.g., at least a 5% increase, at least a 10% increase, at least a 20% increase, at least a 30% increase, at least a 40% increase, at least a 50% increase, at least a 60% increase, at least a 70% increase, at least a 80% increase, at least a 90% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, at least a 300% increase, or between a 5% increase and a 300% increase, between a 5% increase and a 280% increase, between a 5% increase and a 260% increase, between a 5% increase and a 240% increase, between a 5% increase and a 220% increase, between a 5% increase and a 200% increase, between a 5% increase and a 180% increase, between a 5% increase and a 160% increase, between a 5% increase and a 140% increase, between a 5% increase and a 120% increase, between a 5% increase and a 100% increase, between a 5% increase and a 80% increase, between a 5% increase and a 60% increase, between a 5% increase and a 40% increase, between a 5% increase and a 20% increase, between a 5% increase and a 10% increase, between a 10% increase and a 300% increase, between a 10% increase and a 280% increase, between a 10% increase and a 260% increase, between a 10% increase and a 240% increase, between a 10% increase and a 220% increase, between a 10% increase and a 200% increase, between a 10% increase and a 180% increase, between a 10% increase and a 160% increase, between a 10% increase and a 140% increase, between a 10% increase and a 120% increase, between a 10% increase and a 100% increase, between a 10% increase and a 80% increase, between a 10% increase and a 60% increase, between a 10% increase and a 40% increase, between a 10% increase and a 20% increase, between a 20% increase and a 300% increase, between a 20% increase and a 280% increase, between a 20% increase and a 260% increase, between a 20% increase and a 240% increase, between a 20% increase and a 220% increase, between a 20% increase and a 200% increase, between a 20% increase and a 180% increase, between a 20% increase and a 160% increase, between a 20% increase and a 140% increase, between a 20% increase and a 120% increase, between a 20% increase and a 100% increase, between a 20% increase and a 80% increase, between a 20% increase and a 60% increase, between a 20% increase and a 40% increase, between a 40% increase and a 300% increase, between a 40% increase and a 280% increase, between a 40% increase and a 260% increase, between a 40% increase and a 240% increase, between a 40% increase and a 220% increase, between a 40% increase and a 200% increase, between a 40% increase and a 180% increase, between a 40% increase and a 160% increase, between a 40% increase and a 140% increase, between a 40% increase and a 120% increase, between a 40% increase and a 100% increase, between a 40% increase and a 80% increase, between a 40% increase and a 60% increase, between a 60% increase and a 300% increase, between a 60% increase and a 280% increase, between a 60% increase and a 260% increase, between a 60% increase and a 240% increase, between a 60% increase and a 220% increase, between a 60% increase and a 200% increase, between a 60% increase and a 180% increase, between a 60% increase and a 160% increase, between a 60% increase and a 140% increase, between a 60% increase and a 120% increase, between a 60% increase and a 100% increase, between a 60% increase and a 80% increase, between a 80% increase and a 300% increase, between a 80% increase and a 280% increase, between a 80% increase and a 260% increase, between a 80% increase and a 240% increase, between a 80% increase and a 220% increase, between a 80% increase and a 200% increase, between a 80% increase and a 180% increase, between a 80% increase and a 160% increase, between a 80% increase and a 140% increase, between a 80% increase and a 120% increase, between a 80% increase and a 100% increase, between a 100% increase and a 300% increase, between a 100% increase and a 280% increase, between a 100% increase and a 260% increase, between a 100% increase and a 240% increase, between a 100% increase and a 220% increase, between a 100% increase and a 200% increase, between a 100% increase and a 180% increase, between a 100% increase and a 160% increase, between a 100% increase and a 140% increase, between a 100% increase and a 120% increase, between a 120% increase and a 300% increase, between a 120% increase and a 280% increase, between a 120% increase and a 260% increase, between a 120% increase and a 240% increase, between a 120% increase and a 220% increase, between a 120% increase and a 200% increase, between a 120% increase and a 180% increase, between a 120% increase and a 160% increase, between a 120% increase and a 140% increase, between a 140% increase and a 300% increase, between a 140% increase and a 280% increase, between a 140% increase and a 260% increase, between a 140% increase and a 240% increase, between a 140% increase and a 220% increase, between a 140% increase and a 200% increase, between a 140% increase and a 180% increase, between a 140% increase and a 160% increase, between a 160% increase and a 300% increase, between a 160% increase and a 280% increase, between a 160% increase and a 260% increase, between a 160% increase and a 240% increase, between a 160% increase and a 220% increase, between a 160% increase and a 200% increase, between a 160% increase and a 180% increase, between a 180% increase and a 300% increase, between a 180% increase and a 280% increase, between a 180% increase and a 260% increase, between a 180% increase and a 240% increase, between a 180% increase and a 220% increase, between a 180% increase and a 200% increase, between a 200% increase and a 300% increase, between a 200% increase and a 280% increase, between a 200% increase and a 260% increase, between a 200% increase and a 240% increase, between a 200% increase and a 220% increase, between a 220% increase and a 300% increase, between a 220% increase and a 280% increase, between a 220% increase and a 260% increase, between a 220% increase and a 240% increase, between a 240% increase and a 300% increase, between a 240% increase and a 280% increase, between a 240% increase and a 260% increase, between a 260% increase and a 300% increase, between a 260% increase and a 280% increase, or between a 280% increase and a 300% increase) in vitro and/or in vivo cytotoxicity of PD-L1+ cells as compared to Ab1.

In some embodiments, an anti-PD-L1 antibody provided herein has increased (e.g., at least a 5% increase, at least a 10% increase, at least a 20% increase, at least a 30% increase, at least a 40% increase, at least a 50% increase, at least a 60% increase, at least a 70% increase, at least a 80% increase, at least a 90% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, at least a 300% increase, or between a 5% increase and a 300% increase (or any of the subranges of this range described herein)) in cellular internalization rate by PD-L1+ cells as compared to Ab1.

In some embodiments, an anti-PD-L1 antibody provided herein has increased (e.g., at least a 5% increase, at least a 10% increase, at least a 20% increase, at least a 30% increase, at least a 40% increase, at least a 50% increase, at least a 60% increase, at least a 70% increase, at least a 80% increase, at least a 90% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, at least a 300% increase, or between a 5% increase and a 300% increase (or any of the subranges of this range described herein)) immune cell infiltration upon administration to a mammal as compared to Ab1.

In some embodiments, an anti-PD-L1 antibody provided herein has increased (e.g., at least a 5% increase, at least a 10% increase, at least a 20% increase, at least a 30% increase, at least a 40% increase, at least a 50% increase, at least a 60% increase, at least a 70% increase, at least a 80% increase, at least a 90% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, at least a 300% increase, or between a 5% increase and a 300% increase (or any of the subranges of this range described herein)) inflammatory cytokine production (e.g., one or more of any of the cytokines described herein) upon administration to a mammal as compared to Ab1.

In some embodiments, an anti-PD-L1 antibody provided herein has increased (e.g., at least a 5% increase, at least a 10% increase, at least a 20% increase, at least a 30% increase, at least a 40% increase, at least a 50% increase, at least a 60% increase, at least a 70% increase, at least a 80% increase, at least a 90% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, at least a 300% increase, or between a 5% increase and a 300% increase (or any of the subranges of this range described herein)) intracellular digestion by PD-L1+ cells as compared to Ab1.

In some embodiments, an anti-PD-L1 antibody provided herein has less than a 10% change (e.g., less than a 8% change, less than a 6% change, less than a 4% change, less than a 2% change, or less than a 1% change) in neutrophil and/or platelet counts upon administration to a mammal as compared to Ab1.

The binding affinity of the PD-L1 antibodies of the invention (i.e., dissociation constant, $K_D$) is preferably greater than that of Ab1. Preferred PD-L1 antibodies bind to the same epitope and/or compete with Ab1 for binding to human PD-L1. In an embodiment, the binding affinity of the PD-L1 antibodies of the invention is greater than 2.7 nM. In a further embodiment, the monovalent binding affinity of the PD-L1 antibodies of the invention is greater than 2.7 nM. In another embodiment, the $k_{assoc}$ (or on rate) is less than that of Ab1. In a further embodiment, the $k_{assoc}$ is less than $5.5 \times 10^5$ $M^{-1}s^{-1}$. In another embodiment, the $k_{dissoc}$ (or off rate) is greater than that of Ab1. In a further embodiment, the $k_{dissoc}$ is greater than $1.50 \times 10^3$ $s^{-1}$.

Anti-PD-L1 antibodies of the present invention may also be described or specified in terms of their binding affinity to PD-L1 (e.g., human PD-L1). In some embodiments, preferred binding affinities include those with a dissociation constant or $K_D$ greater than 2.7 nM, 5 nM, 6 nM, 7 nM, 8 nM, 9 nM, 10 nM, 15 nM, 20 nM, 25 nM, 30 nM, 40 nM, 50 nM, 60 nM, 70 nM, 80 nM, 90 nM, 100 nM, 110 nM, 120 nM, 130 nM, 140 nM, 150 nM, 200 nM, 250 nM, 300 nM, 400 nM, or 500 nM. In some embodiments, preferred PD-L1 antibodies have a binding affinity between 3 nM and 300 nM, 3 nM and 200 nM, 3 nM and 100 nM, 3 nM and 50 nM, 3 nM and 40 nM, 3 nM and 20 nM, 3 nM and 15 nM, 5 nM and 300 nM, and 5 nM and 15 nM. In some embodiments, preferred PD-L1 antibodies have a binding affinity at least 2-fold, 3-fold, 3.7-fold, 4-fold, or 5-fold greater than the binding affinity of Ab1. In some of the above embodiments, the binding affinity is a monovalent binding affinity.

In some embodiments, the binding of an anti-PD-L1 antibody of the present invention is pH dependent, such that the antibody displays differential binding across a pH gradient. In some embodiments, the anti-PD-L1 antibody displays maximal binding between a pH of about 4 and a pH of about 10. In some embodiments, the maximal binding is between a pH of about 6 and a pH of about 9. In some embodiments, the maximal binding is between a pH of about 6.5 and a pH of about 8.

Preferred antibodies of the invention inhibit cancer (e.g., growth of cells, metastasis and/or lethality to the organisms) as shown on cancerous cells propagating in culture, in an animal model or clinical trial. Animal models can be formed by implanting PD-L1-expressing human tumor cell lines into appropriate immunodeficient rodent strains, e.g., athymic nude mice or SCID mice. These tumor cell lines can be established in immunodeficient rodent hosts either as solid tumor by subcutaneous injections or as disseminated tumors by intravenous injections.

Once established within a host, these tumor models can be applied to evaluate the therapeutic efficacies of the anti-PD-L1 antibodies or conjugated forms thereof as described in the Examples.

Generally, anti-PD-L1 antibodies and/or anti-PD-L1 antibody-drug conjugates of the disclosure bind PD-L1, e.g., human PD-L1, and exert cytostatic and cytotoxic effects on malignant cells, such as cancer cells. The concentration required to yield a 50% reduction in viability compared to untreated cells, or x50, or $IC_{50}$, is one way of measuring cytotoxicity of anti-PD-L1 antibodies and/or anti-PD-ADCs. Preferred antibodies and/or ADCs of the invention show increased cytotoxicity and x50 compared to that of Ab1 antibodies and/or ADCs. In an embodiment, an anti-PD-L1 antibody conjugated to vcMMAE of the invention exhibits an x50 between 10 ng/mL and 30 ng/mL, or between 15 ng/mL and 25 ng/mL in a BXPC3 cell line. In another embodiment, an anti-PD-L1 antibody conjugated to vcMMAE of the invention exhibits an x50 between 15 ng/mL and 55 ng/mL, or between 20 ng/mL and 50 ng/mL in an MDA-MB-231 cell line. In another embodiment, an anti-PD-L1 antibody conjugated to vcMMAE of the invention exhibits an x50 between 1 ng/mL and 7 ng/mL, or between 2 ng/mL and 5 ng/mL in a KARPAS 299 cell line. In another embodiment, an anti-PD-L1 antibody conjugated to vcMMAE of the invention exhibits an x50 between 15 ng/mL and 40 ng/mL, or between 20 ng/mL and 35 ng/mL in an L540CY cell line. In an embodiment, an anti-PD-L1 antibody conjugated to camptothectin of the invention exhibits an x50 between 12 ng/ml and 70 ng/ml, or between 15 ng/ml and 65 ng/ml in a BXPC3 cell line. In another embodiment, an anti-PD-L1 antibody conjugated to camptothectin of the invention exhibits an x50 between 3 ng/mL and 20 ng/mL, or between 5 ng/mL and 17 ng/mL in an MDA-MB-231 cell line. In another embodiment, an anti-PD-L1 antibody conjugated to camptothectin of the invention exhibits an x50 between 1 ng/mL and 18 ng/mL, or between 3 ng/mL and 15 ng/mL in a KARPAS 299 cell line. In another embodiment, an anti-PD-L1 antibody conjugated to camptothectin of the invention exhibits an x50 between 1 ng/mL and 20 ng/mL, or between 1 ng/mL and 15 ng/mL in an L540CY cell line.

Generally, anti-PD-L1 antibodies and/or anti-PD-L1 antibody-drug conjugates of the disclosure are internalized into cells, such as cancer cells. One way of measuring internalization is to utilize a pH-sensitive antibody conjugate which emits fluorescent signal upon internalization in a cell-based assay. This total internalization of antibody can be quantified by the area under the curve (or AUC) of fluorescent signal over time. A FabFluor (IncuCyte®) internalization assay can be used for this quantification. Preferred antibodies and/or ADCs of the invention show increased total internalization compared to that of Ab1 and/or ADCs. In an embodiment, an anti-PD-L1 antibody or ADC of the invention exhibits between 9% and 155% increase of AUC over the AUC of Ab1. In another embodiment, an anti-PD-L1 antibody or ADC of the invention exhibits between 40% and 130%, or between 40% and 50% increase of AUC over the AUC of Ab1, as tested in a 786-0 cell line. In another embodiment, an anti-PD-L1 antibody or ADC of the invention exhibits between 90% and 100%, or between 90% and 95% increase of AUC over the AUC of Ab1, as tested in a A375 cell line. In another embodiment, an anti-PD-L1 antibody or ADC of the invention exhibits between 85% and 155%, or between 85% and 90% increase of AUC over the AUC of Ab1, as tested in a BXPC3 cell line. In another embodiment, an anti-PD-L1 antibody or ADC of the invention exhibits between 9% and 40%, or between 9% and 13% increase of AUC over the AUC of Ab1, as tested in an ES-2 cell line. In another embodiment, an anti-PD-L1 antibody or ADC of the invention exhibits between 75% and 145%, or between 75% and 80% increase of AUC over the AUC of Ab1, as tested in an MDA-MB-231 cell line.

Anti-PD-L1 antibodies of the disclosure are preferably monoclonal, and may be multispecific, human, humanized or chimeric antibodies, single chain antibodies, Fab fragments, F(ab') fragments, fragments produced by a Fab expression library, and PD-L1 binding fragments of any of the above. In some embodiments, the anti-PD-L1 antibodies of the disclosure specifically bind PD-L1. The immunoglobulin molecules of the disclosure can be of any type (e.g., IgG, IgE, IgM, IgD, IgA and IgY), class (e.g., IgG1, IgG2, IgG3, IgG4, IgA1 and IgA2) or subclass of immunoglobulin molecule. In an embodiment, the anti-PD-L1 antibodies of the disclosure are of IgG1 type.

In certain embodiments of the disclosure, the anti-PD-L1 antibodies are antigen-binding fragments (e.g., human antigen-binding fragments) as described herein and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding fragments, including single-chain antibodies, may comprise the variable region(s) alone or in combination with the entirety or a portion of the following: hinge region, CH1, CH2, CH3 and CL domains. Also included in the present disclosure are antigen-binding fragments comprising any combination of variable region(s) with a hinge region, CH1, CH2, CH3 and CL domains. In some embodiments, the anti-PD-L1 antibodies or antigen-binding fragments thereof are human, murine (e.g., mouse and rat), donkey, sheep, rabbit, goat, guinea pig, camelid, horse, or chicken.

The anti-PD-L1 antibodies of the present disclosure may be monospecific, bispecific, trispecific or of greater multi specificity. Multispecific antibodies may be specific for different epitopes of PD-L1 or may be specific for both PD-L1 as well as for a heterologous protein. See, e.g., PCT publications WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; Kostelny et al., 1992, J. Immunol. 148:1547 1553.

Anti-PD-L1 antibodies of the present disclosure may be described or specified in terms of the particular CDRs they comprise. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme). The boundaries of a given CDR may vary depending on the scheme used for identification. In some embodiments, a "CDR" or "complementarity determining region," or individual specified CDRs (e.g., CDR-H1, CDR-H2, CDR-H3), of a given antibody or region thereof (e.g., variable region thereof) should be understood to encompass a (or the specific) CDR as defined by any of the aforementioned schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes. The scheme for identification of a particular CDR or CDRs may be specified, such as the CDR as defined by the Kabat, Chothia, AbM or IMGT method.

CDR sequences of the anti-PD-L1 antibodies and of the anti-PD-L1 antibody-drug conjugates described herein are according to the Kabat numbering scheme as described in Kabat et al. (1991), "Sequences of Proteins of Immunological Interest," 5th Ed. Public Health Service, National Institutes of Health, Bethesda, MD.

In one aspect, provided herein is an anti-PD-L1 antibody and/or anti-PD-L1 antibody-drug conjugate comprising a heavy chain variable region and a light chain variable region, wherein the heavy chain variable region comprises (i) CDR-H1 comprising the amino acid sequence of SEQ ID NO:13, (ii) CDR-H2 comprising the amino acid sequence of SEQ ID NO:14, and (iii) CDR-H3 comprising the amino acid sequence of SEQ ID NO:15; and/or wherein the light chain variable region comprises (i) CDR-L1 comprising the amino acid sequence of SEQ ID NO:16, (ii) CDR-L2 comprising the amino acid sequence of SEQ ID NO:17, and (iii) CDR-L3 comprising the amino acid sequence of SEQ ID NO:18, wherein the CDRs of the anti-PD-L1 antibody are defined by the Kabat numbering scheme.

In one aspect, provided herein is an anti-PD-L1 antibody and/or anti-PD-L1 antibody-drug conjugate comprising a heavy chain variable domain comprising the amino acid sequence of SEQ ID NO:11 and comprising a light chain variable domain comprising the amino acid sequence of SEQ ID NO:12. In one aspect, provided herein is an anti-PD-L1 antibody and/or anti-PD-L1 antibody-drug conjugate comprising a heavy chain comprising the amino acid sequence of SEQ ID NO:9 and comprising a light chain comprising the amino acid sequence of SEQ ID NO:10.

In some embodiments, provided herein is an anti-PD-L1 antibody and/or anti-PD-L1 antibody-drug conjugate comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:11. In certain embodiments, a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:11 contains substitutions (e.g., conservative substitutions), insertions, or deletions relative to the reference sequence and retains the ability to bind to a PD-L1 (e.g., human PD-L1). In certain embodiments, a total of 1 to 10 amino acids have been substituted, inserted and/or deleted in SEQ ID NO:11. In certain embodiments, substitutions, insertions, or deletions (e.g., 1, 2, 3, 4, or 5 amino acids) occur in regions outside the CDRs (i.e., in the FRs). In some embodiments, the anti-PD-L1 antibody comprises a heavy chain variable domain sequence of SEQ ID NO:11 including post-translational modifications of that sequence.

In some embodiments, provided herein is an anti-PD-L1 antibody and/or anti-PD-L1 antibody-drug conjugate comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:12. In certain embodiments, a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:12 contains substitutions (e.g., conservative substitutions), insertions, or deletions relative to the reference sequence and retains the ability to bind to a PD-L1 (e.g., human PD-L1). In certain embodiments, a total of 1 to 10 amino acids have been substituted, inserted and/or deleted in SEQ ID NO:12. In certain embodiments, substitutions, insertions, or deletions (e.g., 1, 2, 3, 4, or 5 amino acids) occur in regions outside the CDRs (i.e., in the FRs). In some embodiments, the anti-PD-L1 antibody comprises a light chain variable domain sequence of SEQ ID NO:12 including post-translational modifications of that sequence.

In some embodiments, provided herein is an anti-PD-L1 antibody and/or anti-PD-L1 antibody-drug conjugate comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:1. In certain embodiments, a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:1 contains substitutions (e.g., conservative substitutions), insertions, or deletions relative to the reference sequence and retains the ability to bind to a PD-L1 (e.g., human PD-L1). In certain embodiments, a total of 1 to 10 amino acids have been substituted, inserted and/or deleted in SEQ ID NO:1. In certain embodiments, a heavy chain contains one point mutation relative to SEQ ID NO:1. In further embodiments, the one point mutation is located in a CDR region.

In some embodiments, provided herein is an anti-PD-L1 antibody and/or anti-PD-L1 antibody-drug conjugate comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:2. In certain embodiments, a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:2 contains substitutions (e.g., conservative substitutions), insertions, or deletions relative to the reference sequence and retains the ability to bind to a PD-L1 (e.g., human PD-L1). In certain embodiments, a total of 1 to 10 amino acids have been substituted, inserted and/or deleted in SEQ ID NO:2. In certain embodiments, a light chain contains one point mutation relative to SEQ ID NO:2. In further embodiments, the one point mutation is located in a CDR region.

In some embodiments, the anti-PD-L1 antibody or the anti-PD-L1 antibody of the anti-PD-L1 antibody-drug conjugate is a monoclonal antibody.

There are five classes of immunoglobulins: IgA, IgD, IgE, IgG and IgM, having heavy chains designated α, δ, ε, γ and µ, respectively. The γ and α classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. *mAbs* Vol 1 Issue 4 1-7) any of which are suitable for use in some of the embodiments herein. Common allotypic variants in human populations are those designated by the letters a, f, n, z or combinations thereof. In any of the embodiments herein, the antibody may comprise a heavy chain Fc region comprising a human IgG Fc region. In further embodiments, the human IgG Fc region comprises a human IgG1.

The antibodies also include derivatives that are modified, i.e., by the covalent attachment of any type of molecule to the antibody such that covalent attachment does not prevent the antibody from binding to PD-L1 or from exerting a cytostatic or cytotoxic effect on cells. For example, but not by way of limitation, the antibody derivatives include antibodies that have been modified, e.g., by glycosylation, acetylation, PEGylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Humanized Antibodies

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. A preferred acceptor sequence for the heavy chain is the germline $V_H$ exon $V_H$1-2 (also referred to in the literature as HV1-2) (Shin et al, 1991, EMBO J. 10:3641-3645) and for the hinge region (JH), exon JH-6 (Mattila et al, 1995, Eur. J. Immunol. 25:2578-2582). For the light chain, a preferred acceptor sequence is exon VK2-30 (also referred to in the literature as KV2-30) and for the hinge region exon JK-4 (Hieter et al, 1982, J. Biol. Chem. 257:1516-1522). Thus, a humanized antibody is an antibody having some or all CDRs entirely or substantially from a donor antibody and variable region framework sequences and constant regions, if present, entirely or substantially from human antibody sequences. Similarly, a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 60%, 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical. In some embodiments, the PD-L1 antibodies of the invention are humanized antibodies.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Selection of Constant Region

The heavy and light chain variable regions of humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotopes IgG1 and IgG3 have strong complement-dependent cytotoxicity, human isotype IgG2 weak complement-dependent cytotoxicity and human. IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed as tetramers containing two light and two heavy chains, as separate heavy chains, light chains, as Fab, Fab', F(ab')$_2$, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

Exemplary substitution include the amino acid substitution of the native amino acid to a cysteine residue is introduced at amino acid position 234, 235, 237, 239, 267, 298, 299, 326, 330, or 332, preferably an S239C mutation in a human IgG1 isotype (US 20100158909). The presence of an additional cysteine residue allows interchain disulfide bond formation. Such interchain disulfide bond formation can cause steric hindrance, thereby reducing the affinity of the Fc region-FcγR binding interaction. The cysteine residue(s) introduced in or in proximity to the Fc region of an IgG constant region can also serve as sites for conjugation to therapeutic agents (i.e., coupling cytotoxic drugs using thiol specific reagents such as maleimide derivatives of drugs. The presence of a therapeutic agent causes steric hindrance, thereby further reducing the affinity of the Fc region-FcγR binding interaction. Other substitutions at any of positions 234, 235, 236 and/or 237 reduce affinity for Feγ receptors, particularly FcγRI receptor {see, e.g., U.S. Pat. Nos. 6,624,821, 5,624,821).

The in vivo half-life of an antibody can also impact on its effector functions. The half-life of an antibody can be increased or decreased to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, 2000, Annu. Rev. Immunol. 18:739-766; Ghetie and Ward, 2002, Immunol. Res. 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, Ann. Rev. Immunol. 18:739-766; Ghetie and Ward, 2002, Immunol. Res. 25:97-113). The region on human IgG1 involved in FcRn binding has been mapped (Shields et al, 2001, J. Biol. Chem. 276:6591-604). Alanine substitutions at positions Pro238, Thr256, Thr307, Gln311, Asp312, Glu380, Glu382, or Asn434 of human IgG1 enhance FcRn binding (Shields et al, 2001, J. Biol. Chem. 276:6591-604). IgG1 molecules harboring these substitutions have longer serum half-lives. Consequently, these modified IgG1 molecules may be able to carry out their effector functions, and hence exert their therapeutic efficacies, over a longer period of time compared to unmodified IgG1. Other exemplary substitutions for increasing binding to FcRn include a Gin at position 250 and/or a Leu at position 428. EU numbering is used for all position in the constant region.

Oligosaccharides covalently attached to the conserved Asn297 are involved in the ability of the Fc region of an IgG to bind FeyR (Lund et al, 1996, J. Immunol. 157:4963-69; Wright and Morrison, 199', Trends Biotechnol. 15:26-31). Engineering of this glycoform on IgG can significantly improve IgG-mediated ADCC. Addition of bisecting N-acetylglucosamine modifications (Umana et al, 1999, Nat. Biotechnol. 17:176-180; Davies et al, 2001, Biotech. Bioeng. 74:288-94) to this glycoform or removal of fucose (Shields et al, 2002, J. Biol. Chem. 277:26733-40; Shinkawa et al, 2003, J. Biol. Chem. 278:6591-604; Niwa et al., 2004, Cancer Res. 64:2127-33) from this glycoform are two examples of IgG Fc engineering that improves the binding between IgG Fc and FcyR, thereby enhancing Ig-mediated ADCC activity.

A systemic substitution of solvent-exposed amino acids of human IgG1 Fc region has generated IgG variants with altered FcyR binding affinities (Shields et al, 2001, J. Biol. Chem. 276:6591-604). When compared to parental IgG1, a subset of these variants involving substitutions at Thr256/Ser298, Ser298/Glu333, Ser298/Lys334, or Ser298/Glu333 Lys334 to Ala demonstrate increased in both binding affinity toward FcTR and ADCC activity (Shields et al, 2001, J. Biol. Chem. 276:6591-604; Okazaki et al, 2004, J. Mol. Biol. 336:1239-49).

Complement fixation activity of antibodies (both C1q binding and CDC activity) can be improved by substitutions at Lys326 and Glu333 (Idusogie et al., 2001, J. Immunol. 166:2571-2575). The same substitutions on a human IgG2 backbone can convert an antibody isotype that binds poorly to C1q and is severely deficient in complement activation activity to one that can both bind C1q and mediate CDC (Idusogie et al, 2001, J. Immunol. 166:2571-75). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al, 1995, J. Immunol. 154:2226-36). Also, substituting Ser444 located close to the carboxy-terminal of IgG 1 heavy chain with Cys induced tail-to-tail dimerization of IgG 1 with a 200-fold increase of CDC activity over monomeric IgG1 (Shopes et al, 1992, J. Immunol. 148:2918-22). In addition, a bispecific diabody construct with specificity for C1q also confers CDC activity (Kontermann et al., 1997, Nat. Biotech. 15:629-31).

Complement activity can be reduced by mutating at least one of the amino acid residues 318, 320, and 322 of the heavy chain to a residue having a different side chain, such as Ala. Other alkyl-substituted non-ionic residues, such as Gly, Leu, or Val, or such aromatic non-polar residues as Phe, Tyr, Trp and Pro in place of any one of the three residues also reduce or abolish C1q binding. Ser, Thr, Cys, and Met can be used at residues 320 and 322, but not 318, to reduce or abolish C1q binding activity.

Replacement of the 318 (Glu) residue by a polar residue may modify but not abolish C1q binding activity. Replacing residue 297 (Asn) with Ala results in removal of lytic activity but only slightly reduces (about three fold weaker) affinity for C1q. This alteration destroys the glycosylation site and the presence of carbohydrate that is required for complement activation. Any other substitution at this site also destroys the glycosylation site. The following mutations and any combination thereof also reduce C1q binding: D270A, K322A, P329A, and P31 IS (see WO 06/036291). The L234A/L235A mutation (or LALA mutation) also reduces C1q binding, as well as FcyR binding. In an embodiment, an anti-PD-L1 antibody of the invention includes the L234A/L235A mutation.

Reference to a human constant region includes a constant region with any natural allotype or any permutation of residues occupying polymorphic positions in natural allotypes. Also, up to 1, 2, 5, or 10 mutations may be present relative to a natural human constant region, such as those indicated above to reduce Fcgamma receptor binding or increase binding to FcRN.

V. Expression of Recombinant Antibodies

Humanized antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Once expressed, antibodies can be purified according to standard procedures of the art, including HPLC purification, column chromatography, gel electrophoresis and the like (see generally, Scopes, Protein Purification (Springer-Verlag, NY, 1982)).

VI. Nucleic Acids

The invention further provides nucleic acids encoding any of the humanized heavy and light chains described above.

Typically, the nucleic acids also encode a signal peptide fused to the mature heavy and light chains. Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

In some aspects, also provided herein are nucleic acids encoding an anti-PD-L1 antibody or antigen-binding fragment thereof as described herein. Further provided herein are vectors comprising the nucleic acids encoding an anti-PD-L1 antibody or antigen-binding fragment thereof as described herein. Further provided herein are host cells expressing the nucleic acids encoding an anti-PD-L1 antibody or antigen-binding fragment thereof as described herein. Further provided herein are host cells comprising the vectors comprising the nucleic acids encoding an anti-PD-L1 antibody or antigen-binding fragment thereof as described herein.

The anti-PD-L1 antibodies described herein may be prepared by well-known recombinant techniques using well known expression vector systems and host cells. In one embodiment, the antibodies are prepared in a CHO cell using the GS expression vector system as disclosed in De la Cruz Edmunds et al., 2006, Molecular Biotechnology 34; 179-190, EP216846, U.S. Pat. No. 5,981,216, WO 87/04462, EP323997, U.S. Pat. Nos. 5,591,639, 5,658,759, EP338841, U.S. Pat. Nos. 5,879,936, and 5,891,693.

Monoclonal anti-PD-L1 antibodies described herein may e.g. be produced by the hybridoma method first described by Kohler et al., *Nature,* 256, 495 (1975), or may be produced by recombinant DNA methods. Monoclonal antibodies may also be isolated from phage antibody libraries using the techniques described in, for example, Clackson et al., *Nature,* 352, 624-628 (1991) and Marks et al., *J Mol, Biol.,* 222(3):581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

Antibody-Drug Conjugates

Anti-PD-L1 antibodies can be conjugated to cytotoxic or cytostatic moieties (including pharmaceutically compatible salts thereof) to form an antibody drug conjugate (ADC). Particularly suitable moieties for conjugation to antibodies are cytotoxic agents (e.g., chemotherapeutic agents), prodrug converting enzymes, radioactive isotopes or compounds, or toxins (these moieties being collectively referred to as a therapeutic agent). For example, an anti-PD-L1 antibody can be conjugated to a cytotoxic agent such as a chemotherapeutic agent, or a toxin (e.g., a cytostatic or cytocidal agent such as, e.g., abrin, ricin A, pseudomonas exotoxin, or diphtheria toxin).

An anti-PD-L1 antibody can be conjugated to a pro-drug converting enzyme. The pro-drug converting enzyme can be recombinantly fused to the antibody or chemically conjugated thereto using known methods. Exemplary pro-drug converting enzymes are carboxypeptidase G2, beta-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Arnon et al, "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al, "Antibodies For Drug Delivery," in Controlled Drug Delivery (Robinson et al. eds., Marcel Dekker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al, 1982, Immunol. Rev. 62:119-58. See also, e.g., PCT publication WO 89/12624.)

The therapeutic agent can be conjugated in a manner that reduces its activity unless it is cleaved off the antibody (e.g., by hydrolysis, by antibody degradation or by a cleaving agent). Such a therapeutic agent is attached to the antibody with a cleavable linker that is sensitive to cleavage in the intracellular environment of the PD-L1-expressing cancer cell but is not substantially sensitive to the extracellular environment, such that the conjugate is cleaved from the antibody when it is internalized by the PD-L1-expressing cancer cell (e.g., in the endosomal or, for example by virtue of pH sensitivity or protease sensitivity, in the lysosomal environment or in the caveolear environment).

Typically the ADC comprises a linker region between the therapeutic agent and the anti-PD-L1 antibody. As noted supra, typically, the linker is cleavable under intracellular conditions, such that cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Typically, the peptidyl linker is at least two amino acids long or at least three amino acids long. Cleaving agents can include cathepsins B and D and plasmin (see, e.g., Dubowchik and Walker, 1999, Pharm. Therapeutics 83:67-123). Most typical are peptidyl linkers that are cleavable by enzymes that are present in PD-L1-expressing cells. For example, a peptidyl linker that is cleavable by the thiol-dependent protease cathepsin-B, which is highly expressed in cancerous tissue, can be used (e.g., a linker comprising a Phe-Leu or a Gly-Phe-Leu-Gly peptide). Other such linkers are described, e.g., in U.S. Pat. No. 6,214,345. In specific embodiments, the peptidyl linker cleavable by an intracellular protease comprises a Val-Cit linker or a Phe-Lys dipeptide (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

The cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622, 929; Dubowchik and Walker, 1999, Pharm. Therapeutics 83:67-123; Neville et al, 1989, Biol. Chem. 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

Other linkers are cleavable under reducing conditions (e.g., a disulfide linker). Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. {See, e.g., Thorpe et al, 1987, Cancer Res. 47:5924-5931; Wawrzynczak et al, In Immunoconjugates: Antibody Conjugates in Radioimagery and Therapy of Cancer (C. W. Vogel ed., Oxford U. Press, 1987. See also U.S. Pat. No. 4,880,935.)

The linker can also be a malonate linker (Johnson et al, 1995, Anticancer Res. 15:1387-93), a maleimidobenzoyl linker (Lau et al, 1995, Bioorg-Med-Chem. 3(10):1299-1304), or a 3'-N-amide analog (Lau et al, 1995, Bioorg-Med-Chem. 3(10):1305-12). The linker can also be a malonate linker (Johnson et al, 1995, Anticancer Res. 15:1387-93), a maleimidobenzoyl linker (Lau et al, 1995, Bioorg-Med-Chem. 3(10):1299-1304), or a 3'-N-amide analog (Lau et al, 1995, Bioorg-Med-Chem. 3(10):1305-12).

The linker also can be a non-cleavable linker, such as an maleimido-alkylene- or maleimide-aryl linker that is directly attached to the therapeutic agent (e.g., a drug). An active drug-linker is released by degradation of the antibody.

Typically, the linker is not substantially sensitive to the extracellular environment meaning that no more than about 20%, typically no more than about 15%, more typically no more than about 10%, and even more typically no more than about 5%, no more than about 3%, or no more than about 1% of the linkers in a sample of the ADC is cleaved when the ADC present in an extracellular environment (e.g., in plasma).

Whether a linker is not substantially sensitive to the extracellular environment can be determined, for example, by incubating independently with plasma both (a) the ADC (the "ADC sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

The linker can also promote cellular internalization. The linker can promote cellular internalization when conjugated to the therapeutic agent (i.e., in the milieu of the linker-therapeutic agent moiety of the ADC or ADC derivative as described herein). Alternatively, the linker can promote cellular internalization when conjugated to both the therapeutic agent and the anti-PD-L1 antibody (i.e., in the milieu of the ADC as described herein).

The anti-PD-L1 antibody can be conjugated to the linker via a heteroatom of the antibody. These heteroatoms can be present on the antibody in its natural state or can be introduced into the antibody. In some aspects, the anti-PD-1 antibody will be conjugated to the linker via a nitrogen atom of a lysine residue. In other aspects, the anti-PD-L1 antibody will be conjugated to the linker via a sulfur atom of a cysteine residue. The cysteine residue can be naturally-occurring or one that is engineered into the antibody. Methods of conjugating linkers and drug-linkers to antibodies via lysine and cysteine residues are known in the art.

Exemplary antibody-drug conjugates include auristatin based antibody-drug conjugates (i.e., the drug component is an auristatin drug). Auristatins bind tubulin, have been shown to interfere with microtubule dynamics and nuclear and cellular division, and have anticancer activity. Typically the auristatin based antibody-drug conjugate comprises a linker between the auristatin drug and the anti-PD-L1 antibody. The linker can be, for example, a cleavable linker (e.g., a peptidyl linker, a carbohydrate linker) or a non-cleavable linker (e.g., linker released by degradation of the antibody). Auristatins include auristatin T, MMAF, and MMAE. The synthesis and structure of exemplary auristatins are described in U.S. Pat. Nos. 7,659,241, 7,498,298, 2009-0111756, 2009-0018086, and U.S. Pat. No. 7,968,687 each of which is incorporated herein by reference in its entirety and for all purposes.

Exemplary antibody-drug conjugates also include camptothecin based antibody-drug conjugates (i.e., the drug component is a camptothecin drug). Camptothecins are topoisomerase inhibitors that have been shown to have anticancer activity. Typically the camptothecin based antibody-drug conjugate comprises a linker between the camptothecin drug and the anti-PD-L1 antibody. The linker can be, for example, a cleavable linker (e.g., a peptidyl linker, a carbohydrate linker) or a non-cleavable linker (e.g., linker released by degradation of the antibody). The synthesis and structure of exemplary camptothecin drug-linkers is described in PCT/US19/025968 (filed Apr. 5, 2019), which is incorporated herein by reference in its entirety and for all purposes.

Other exemplary antibody-drug conjugates include maytansinoid antibody-drug conjugates (i.e., the drug component is a maytansinoid drug), and benzodiazepine antibody drug conjugates (i.e., the drug component is a benzodiazepine (e.g., pyrrolo[1,4]benzodiazepine dimers (PBD dimer), indolinobenzodiazepine dimers, and oxazolidinobenzodiazepine dimers)).

Exemplary antibody drug conjugates include vcMMAE and mcMMAF antibody drug conjugates as follows wherein p represents the drug load and Ab represents the anti-PD-L1 antibody:

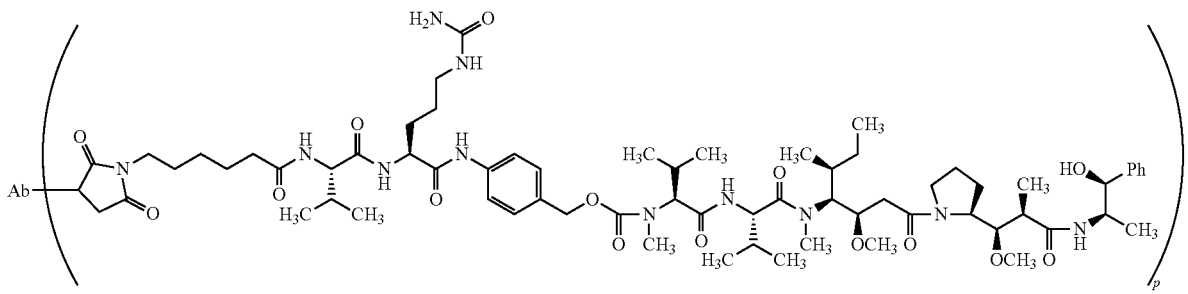

vcMMAE

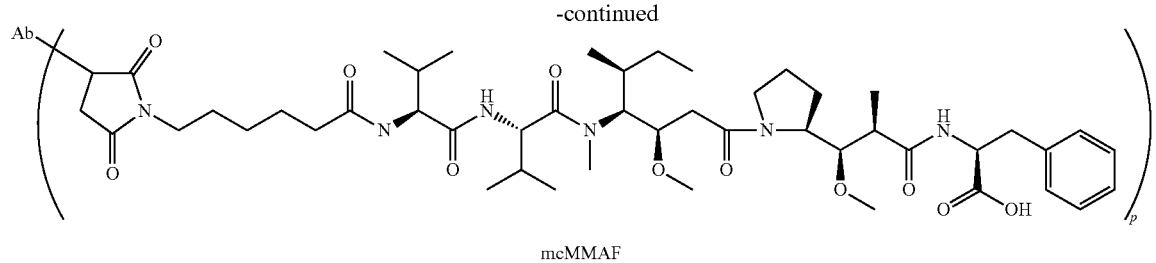

mcMMAF or a pharmaceutically acceptable salt thereof.

Exemplary anti-PD-L1 antibody drug conjugates include camptothecin antibody drug conjugates as follows wherein p represents the drug load and Ab represents the anti-PD-L1 antibody:

In some embodiments, the camptothecin ADC has the formula (IC):

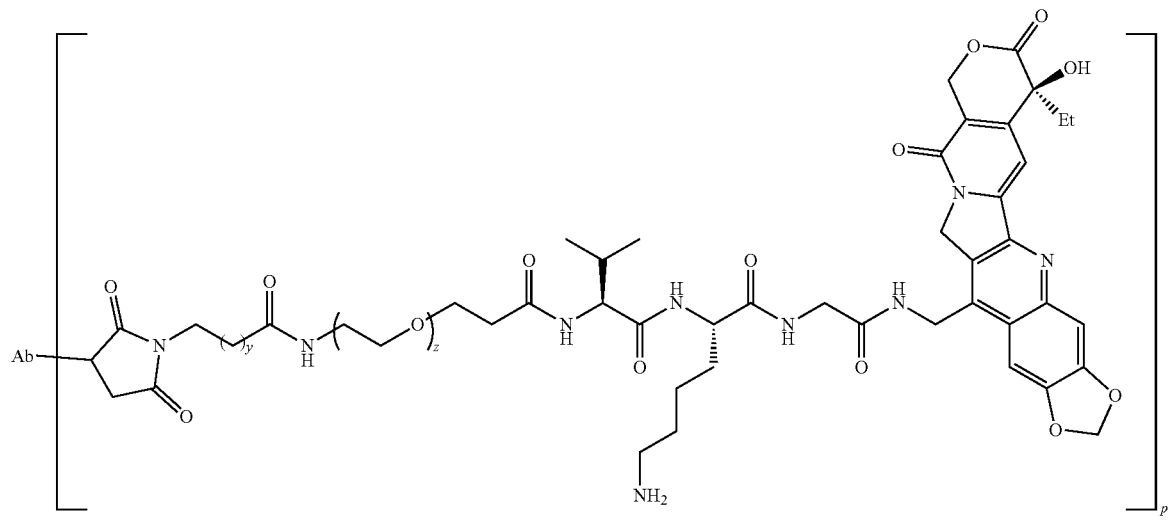

(IC)

or a pharmaceutically acceptable salt thereof;
wherein
Ab is an anti-PD-L1 antibody;
y is 1, 2, 3, or 4, or is 1 or 4; and
z is an integer from 2 to 12, or is 2, 4, 8, or 12;
and p is 1-16.

In some aspect of these embodiments, p is 2, 3, 4, 5, 6, 7, 8, 9, or 10. In some aspect, p is 2, 4 or 8.

In some embodiments, the camptothecin ADC has the formula:
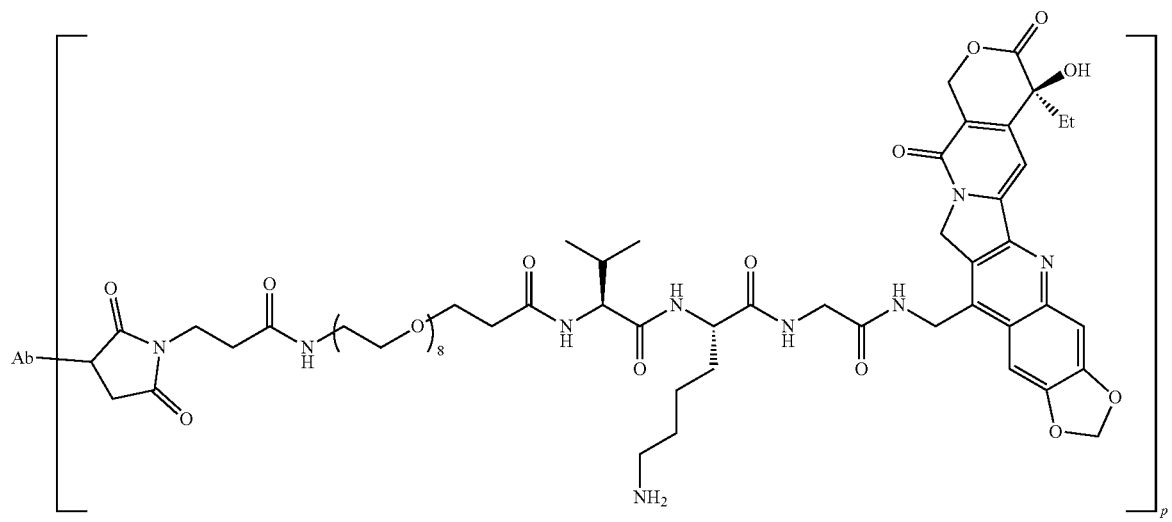
or a pharmaceutically acceptable salt thereof;
wherein p is 2, 4, or 8, preferably p is 8.
In some embodiments, the camptothecin ADC has the formula:
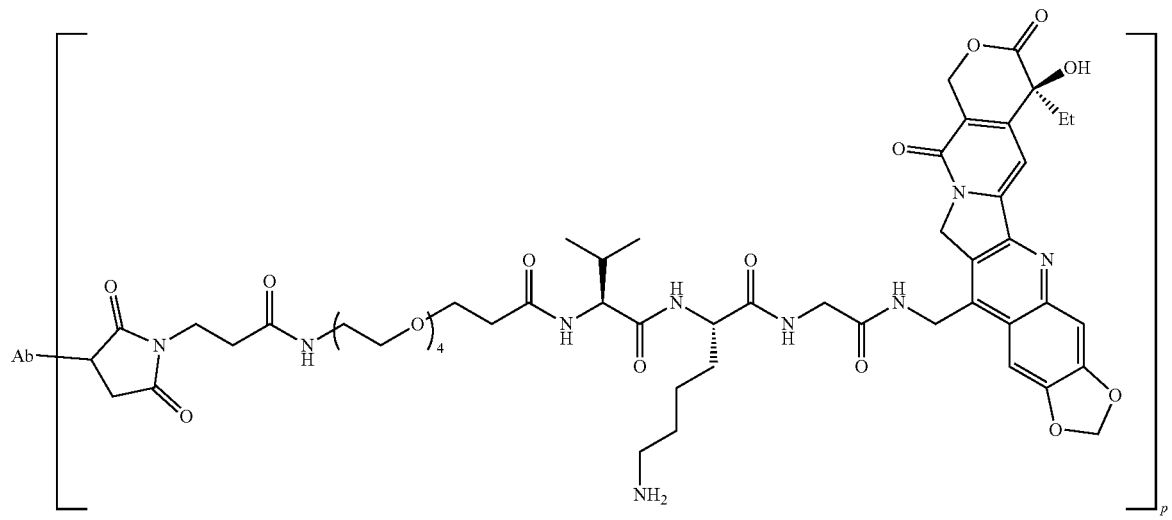
or a pharmaceutically acceptable salt thereof;
wherein p is 2, 4, or 8, preferably p is 8.

In some embodiments, the camptothecin drug-linker has the formula:
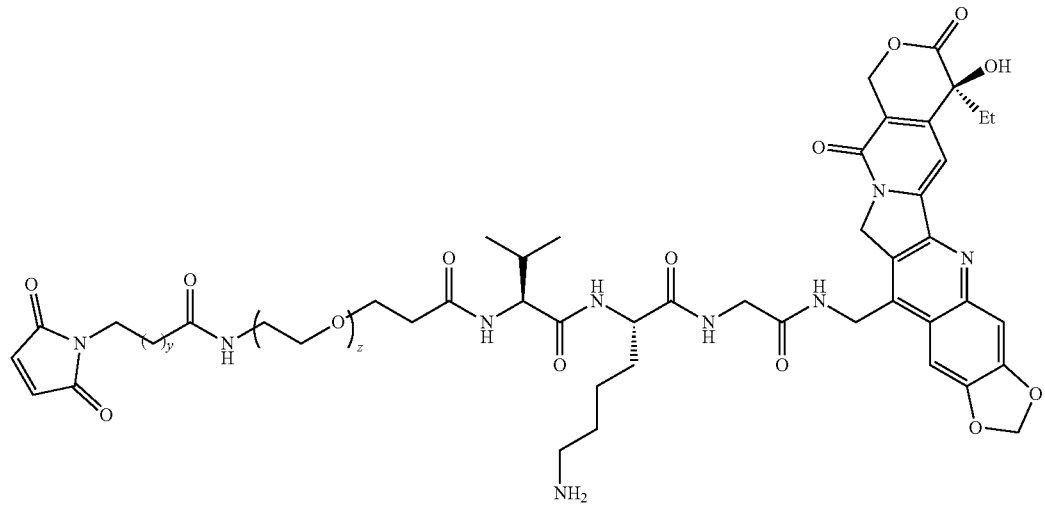
or a pharmaceutically acceptable salt thereof;
wherein
y is 1, 2, 3, or 4, or is 1 or 4; and
z is an integer from 2 to 12, or is 2, 4, 8, or 12.
In some embodiments, the camptothecin drug-linker has the formula:
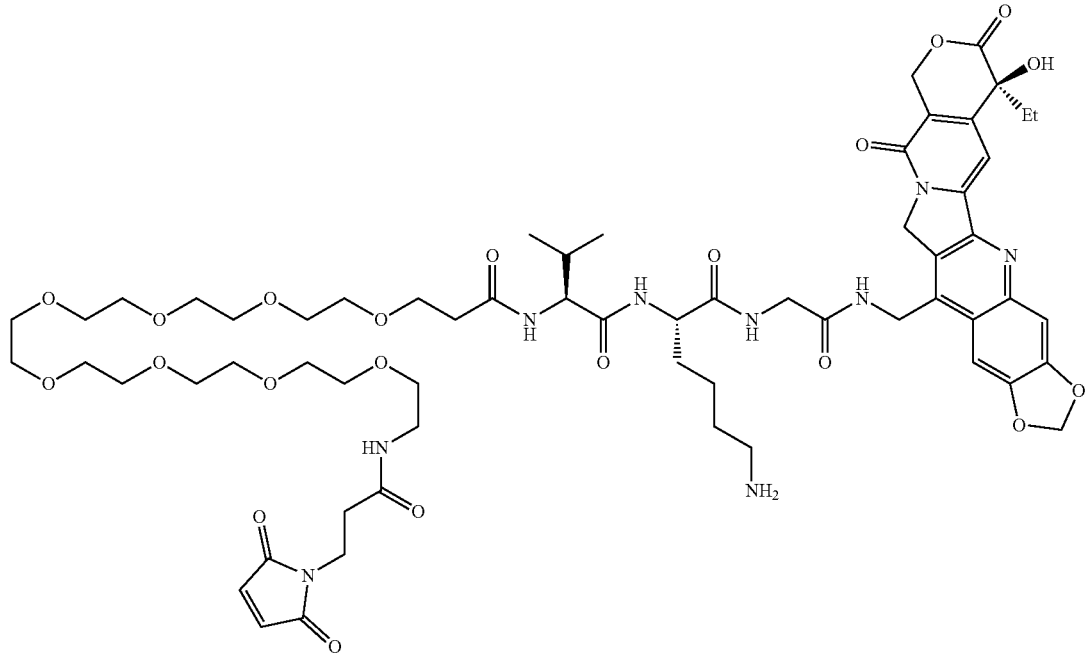
MP-PEG8-VKG-CAMPTOTHECIN In some embodiments, the camptothecin drug-linker has the formula:

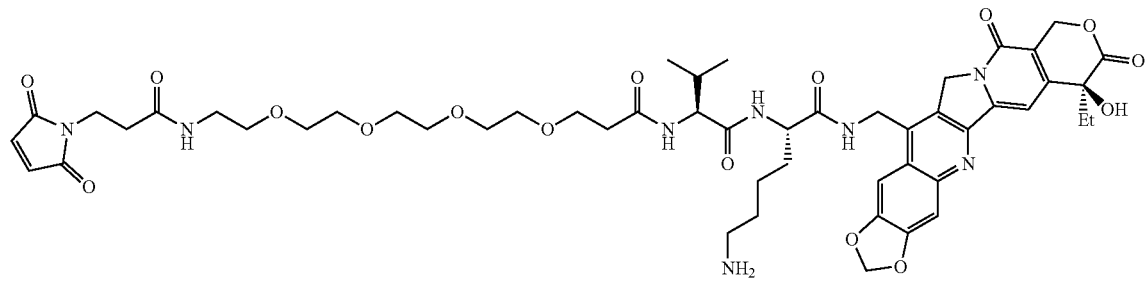

MP-PEG4-VKG-CAMPTOTHECIN

In some embodiments, the camptothecin drug-linker has the formula:

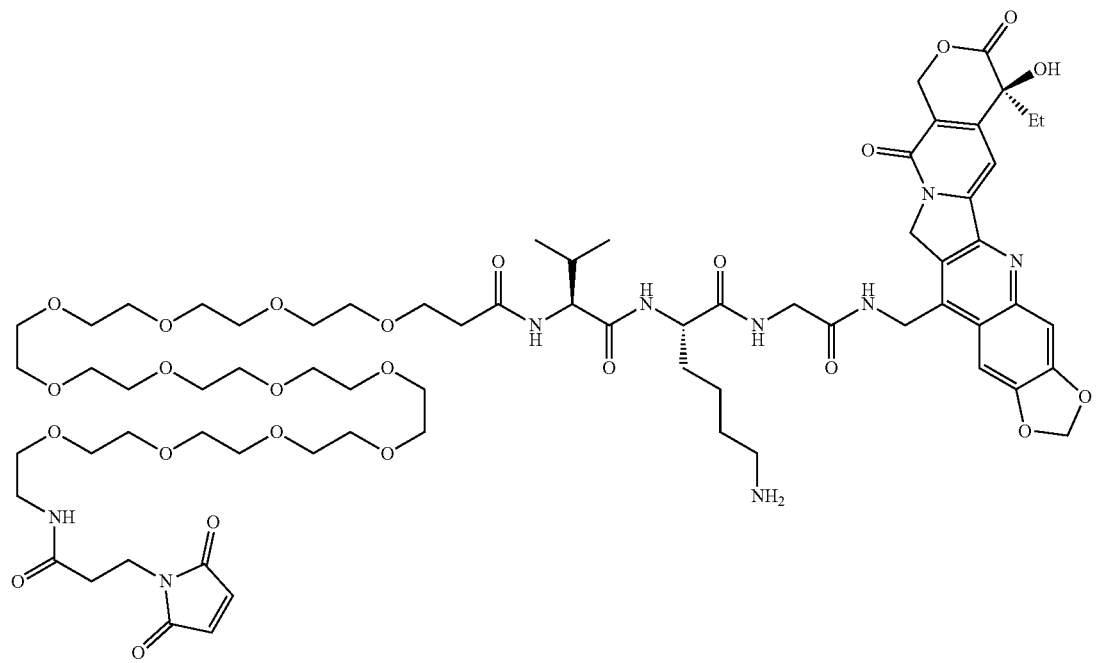

MP-PEG12-VKG-CAMPTOTHECIN

Referring to the PD-L1 targeted antibody-drug conjugates, the subscript p represents the drug load and, depending on the context, can represent the number of molecules of drug-linker molecules attached to an individual antibody molecule and as such, is an integer value, or can represent an average drug load and, as such, can be an integer or non-integer value but is typically a non-integer value. An average drug load represents the average number of drug-linker molecules per antibody in a population. Often, but not always, when we refer to an antibody, e.g., a monoclonal antibody, we are referring to a population of antibody molecules. In a composition comprising a population of antibody-drug conjugate molecules, the average drug load is an important quality attribute as it determines the amount of drug that can be delivered to a target cell. The percentage of unconjugated antibody molecules in the composition is included in the average drug load value.

In preferred aspects of the present invention, the average drug load when referring to a composition comprising a population of antibody-drug conjugate compounds is from 1 to about 16, preferably about 2 to about 14, more preferably about 2 to about 10.

For the MMAE and camptothecin ADCs, such as those exemplified herein, preferred average drug load is about 2, 4, or 8, and a particularly preferred average drug load is about 8. In an embodiment, the preferred average drug load for MMAE ADCs is 2 or 4. In an embodiment, the preferred average drug load for camptothecin ADCs is 4 or 8. In exemplary embodiments, the drug-linkers are conjugated to the cysteine residues of the reduced inter-chain disulfides. In some aspects, the actual drug load for individual antibody molecules in the population of antibody-drug conjugate compounds is from 1 to 10 (or from 6 to 10 or from 6 to 8) with a predominant drug loading of 8. A higher drug load can be achieved, for example, if, in addition to the interchain disulfides, drug-linker is conjugated to introduced cysteine residues (such as a cysteine residue introduced at position 239, according to the EU index).

The PEG (polyethylene glycol) portion of the drug linker can range from 2 to 36. The subscript z in all of the embodiments above is preferably 2 to 12, 4 to 12, 8 to 14, 8 to 12, 10 to 12 or 10 to 14, is more preferably 2, 4, 8, or 12, and is most preferably 8.

Polydisperse PEGS, monodisperse PEGS and discrete PEGs can be used to make the PEGylated antibody drug conjugates of the present invention. Polydisperse PEGs are a heterogeneous mixture of sizes and molecular weights whereas monodisperse PEGs are typically purified from heterogeneous mixtures and are therefore provide a single chain length and molecular weight. Preferred PEG Units are discrete PEGs, compounds that are synthesized in step-wise fashion and not via a polymerization process. Discrete PEGs provide a single molecule with defined and specified chain length. As with the subscript "p", when referring to populations of antibody-drug conjugates, the value for the subscript "n" can be an average number and can be an integer or non-integer number.

Useful classes of cytotoxic agents to conjugate to anti-PD-L1 antibodies include, for example, antitubulin agents, DNA minor groove binding agents, DNA replication inhibitors, chemotherapy sensitizers, or the like. Other exemplary classes of cytotoxic agents include anthracyclines, auristatins, camptothecins, duocarmycins, etoposides, maytansinoids and vinca alkaloids. Some exemplary cytotoxic agents include auristatins (e.g., auristatin T, auristatin E, AFP, monomethyl auristatin F (MMAF), lipophilic monomethyl aurstatin F, monomethyl auristatin E (MMAE)), DNA minor groove binders (e.g., enediynes and lexitropsins), duocarmycins, taxanes (e.g., paclitaxel and docetaxel), vinca alkaloids, nicotinamide phosphoribosyltranferase inhibitor (NAMPTi), tubulysin M, doxorubicin, morpholino-doxorubicin, and cyanomorpholino-doxorubicin.

The cytotoxic agent can be a chemotherapeutic such as, for example, doxorubicin, paclitaxel, melphalan, vinca alkaloids, methotrexate, mitomycin C or etoposide. The agent can also be a CC-1065 analogue, calicheamicin, maytansine, an analog of dolastatin 10, rhizoxin, or palytoxin.

The cytotoxic agent can also be an auristatin. The auristatin can be an auristatin E derivative is, e.g., an ester formed between auristatin E and a keto acid. For example, auristatin E can be reacted with paraacetyl benzoic acid or benzoyl-valeric acid to produce AEB and AEVB, respectively. Other typical auristatins include auristatin T, AFP, MMAF, and MMAE. The synthesis and structure of various auristatins are described in, for example, US 2005-0238649 and US2006-0074008.

The cytotoxic agent can be a DNA minor groove binding agent. (See, e.g., U.S. Pat. No. 6,130,237.) For example, the minor groove binding agent can be a CBI compound or an enediyne (e.g., calicheamicin).

The cytotoxic or cytostatic agent can be an anti-tubulin agent. Examples of anti-tubulin agents include taxanes (e.g., Taxol® (paclitaxel), Taxotere® (docetaxel)), T67 (Tularik), vinca alkyloids (e.g., vincristine, vinblastine, vindesine, and vinorelbine), and auristatins (e.g., auristatin E, AFP, MMAF, MMAE, AEB, AEVB). Exemplary auristatins are shown below in formulae III-XIII. Other suitable antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermoide and eleuthrobin.

The cytotoxic agent can be a maytansinoid, another group of anti-tubulin agents (e.g., DM1, DM2, DM3, DM4). For example, the maytansinoid can be maytansine or a maytansine containing drug linker such as DM-1 or DM-4 (ImmunoGen, Inc.; see also Chari et al., 1992, Cancer Res.)

VIII. Therapeutic Applications

The antibodies of the invention, alone or as anti-PD-L1 antibody-drug conjugates thereof, can be used to treat cancer. Some such cancers show detectable levels of PD-L1 measured at either the protein (e.g., by immunoassay using one of the exemplified antibodies) or mRNA level. Some such cancers show elevated levels of PD-L1 relative to noncancerous tissue of the same type, preferably from the same patient. An exemplary level of PD-L1 on cancer cells amenable to treatment is 5000-500,000 PD-L1 molecules per cell, although higher or lower levels can be treated. Optionally, a level of PD-L1 in a cancer is measured before performing treatment.

Examples of cancers associated with PD-L1 expression and amenable to treatment include melanoma, non-small cell lung cancer (NSCLC), small cell lung cancer (SCLC), head and neck cancer, triple negative breast cancer (TNBC), ovarian cancer, urothelial cancer, hepatocellular carcinoma (HCC), gastric cancer, and cervical cancer. In some embodiments, the antibodies or antibody-drug conjugates of the invention are used in methods of treating melanoma. In some embodiments, the antibodies or antibody-drug conjugates of the invention are used in methods of treating NSCLC. In some embodiments, the antibodies or antibody-drug conjugates of the invention are used in methods of treating SCLC. In some embodiments, the antibodies or antibody-drug conjugates of the invention are used in methods of treating head and neck cancer. In some embodiments, the antibodies or antibody-drug conjugates of the invention are used in methods of treating TNBC. A triple negative breast cancer is a term of art for a cancer lacking detectable estrogen and progesterone receptors and lacking overexpression of HER2/neu. In some embodiments, the antibodies or antibody-drug conjugates of the invention are used in methods of treating ovarian cancer. In some embodiments, the antibodies or antibody-drug conjugates of the invention are used in methods of treating urothelial cancer. In some embodiments, the antibodies or antibody-drug conjugates of the invention are used in methods of treating HCC. In some embodiments, the antibodies or antibody-drug conjugates of the invention are used in methods of treating gastric cancer. In some embodiments, the antibodies or antibody-drug conjugates of the invention are used in methods of treating cervical cancer. The treatment can be applied to patients having primary or metastatic tumors of these kinds. The treatment can also be applied to patients who are refractory to conventional treatments, or who have relapsed following a response to such treatments.

Antibodies of the present invention, such as humanized antibodies, alone or as conjugates thereof, are administered in an effective regime meaning a dosage, route of administration and frequency of administration that delays the onset, reduces the severity, inhibits further deterioration, and/or ameliorates at least one sign or symptom of cancer. If a patient is already suffering from cancer, the regime can be referred to as a therapeutically effective regime. If the patient is at elevated risk of the caner relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for a monoclonal antibody are 0.1 mg/kg to 50 mg/kg of the patient's body weight, more typically 1 mg/kg to 30 mg/kg, 1 mg/kg to 20 mg/kg, 1 mg/kg to 15 mg/kg, 1 mg/kg to 12 mg/kg, or 1 mg/kg to 10 mg/kg 1, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg. Exemplary dosages for a monoclonal antibody or antibody drug conjugates thereof are 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-1500 or 200-1500 mg as a fixed dosage. In some methods, the patient is administered a dose of at least 1.5 mg/kg, at least 2 mg/kg or at least 3 mg/kg, administered once every three weeks or greater. The dosage depends on the frequency of administration, condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration can also be localized directly into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the antibody or conjugate in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between weekly or three out of every four weeks over a continuous course of treatment, although more or less frequent dosing is also possible. For subcutaneous administration, an exemplary dosing frequency is daily to monthly, although more or less frequent dosing is also possible.

The number of dosages administered depends on the nature of the cancer (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be e.g., 1-100 mg/ml, such as 10 mg/ml.

Treatment with antibodies of the invention can be combined with chemotherapy, radiation, stem cell treatment, surgery other treatments effective against the disorder being treated. Useful classes of other agents that can be administered with antibodies and antibody-drug conjugates to PD-L1 as described herein include, for example, antibodies to other receptors expressed on cancerous cells, antitubulin agents (e.g., auristatins), DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Treatment with the anti-PD-L1 antibody or antibody-drug conjugate, optionally in combination with any of the other agents or regimes described above alone or as an antibody drug conjugate, can increase the median progression-free survival or overall survival time of patients with tumors (e.g., melanoma, non-small cell lung cancer (NSCLC), small cell lung cancer (SCLC), head and neck cancer, triple negative breast cancer (TNBC), ovarian cancer, urothelial cancer, hepatocellular carcinoma (HCC), gastric cancer, and cervical cancer), especially when relapsed or refractory, by at least 30% or 40% but preferably 50%, 60% to 70% or even 100% or longer, compared to the same treatment (e.g., chemotherapy) but without an anti-PD-L1 antibody alone or as a conjugate. In addition or alternatively, treatment (e.g., standard chemotherapy) including the anti-PD-L1 antibody alone or as a conjugate can increase the complete response rate, partial response rate, or objective response rate (complete+partial) of patients with tumors by at least 30% or 40% but preferably 50%, 60% to 70% or even 100% compared to the same treatment (e.g., chemotherapy) but without the anti-PD-L1 antibody alone or as a conjugate.

Typically, in a clinical trial (e.g., a phase II, phase II/III or phase III trial), the aforementioned increases in median progression-free survival and/or response rate of the patients treated with standard therapy plus the anti-PD-L1 antibody alone or as conjugate, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

IX. Articles of Manufacture and Kits

In another aspect, an article of manufacture or kit is provided which comprises an anti-PD-L1 antibody or anti- PD-L1 antibody-drug conjugate described herein. The article of manufacture or kit may further comprise instructions for use of the anti-PD-L1 antibody or anti-PD-L1 antibody-drug conjugate described herein in the methods of the invention. Thus, in certain embodiments, the article of manufacture or kit comprises instructions for the use of an anti-PD-L1 antibody or anti-PD-L1 antibody-drug conjugate described herein in methods for treating cancer (e.g., melanoma, non-small cell lung cancer (NSCLC), small cell lung cancer (SCLC), head and neck cancer, triple negative breast cancer (TNBC), ovarian cancer, urothelial cancer, hepatocellular carcinoma (HCC), gastric cancer, and cervical cancer) in a subject comprising administering to the subject an effective amount of an anti-PD-L1 antibody or anti-PD-L1 antibody-drug conjugate described herein. In some embodiments, the subject is a human.

The article of manufacture or kit may further comprise a container. Suitable containers include, for example, bottles, vials (e.g., dual chamber vials), syringes (such as single or dual chamber syringes) and test tubes. In some embodiments, the container is a vial. The container may be formed from a variety of materials such as glass or plastic. The container holds the formulation.

The article of manufacture or kit may further comprise a label or a package insert, which is on or associated with the container, may indicate directions for reconstitution and/or use of the formulation. The label or package insert may further indicate that the formulation is useful or intended for subcutaneous, intravenous (e.g., intravenous infusion), or other modes of administration for treating cancer in a subject (e.g., melanoma, non-small cell lung cancer (NSCLC), small cell lung cancer (SCLC), head and neck cancer, triple negative breast cancer (TNBC), ovarian cancer, urothelial cancer, hepatocellular carcinoma (HCC), gastric cancer, and cervical cancer). The container holding the formulation may be a single-use vial or a multi-use vial, which allows for repeat administrations of the reconstituted formulation. The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

The article of manufacture or kit herein optionally further comprises a container comprising a second medicament, wherein the anti-PD-L1 antibody or anti-PD-L1 antibody-drug conjugate is a first medicament, and which article or kit further comprises instructions on the label or package insert for treating the subject with the second medicament, in an effective amount. In some embodiments, the second medicament is for eliminating or reducing the severity of one or more adverse events.

In some embodiments, the anti-PD-L1 antibody or anti-PD-L1 antibody-drug conjugate is present in the container as a lyophilized powder. In some embodiments, the lyophilized powder is in a hermetically sealed container, such as a vial, an ampoule or sachette, indicating the quantity of the active agent. Where the pharmaceutical is administered by injection, an ampoule of sterile water for injection or saline can be, for example, provided, optionally as part of the kit, so that the ingredients can be mixed prior to administration. Such kits can further include, if desired, one or more of various conventional pharmaceutical components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components can also be included in the kit.

X. Other Applications

The anti-PD-L1 antibodies described herein, such as humanized anti-PD-Lt, antibodies can be used for detecting PD-L1 in the context of clinical diagnosis or treatment or in research. Expression of PD-L1 on a cancer provides an indication that the cancer is amenable to treatment with the antibodies of the present invention. The antibodies can also be sold as research reagents for laboratory research in detecting cells bearing PD-L1 and their response to various stimuli. In such uses, monoclonal antibodies can be labeled with fluorescent molecules, spin-labeled molecules, enzymes or radioisotopes, and can be provided in the form of kit with all the necessary reagents to perform the assay for PD-L1. The antibodies described herein, can be used to detect PD-L1 protein expression and determine whether a cancer is amenable to treatment with PD-L1 ADCs.

All patent filings, website, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Cell lines described in the following examples were maintained in culture according to the conditions specified by the American Type Culture Collection (ATCC) or Deutsche Sammlung von Mikroorganismen und Zellkulturen GmbH, Braunschweig, Germany (DMSZ), or as otherwise known.

Methods

Antibody Generation

SG-559-xx antibodies directed against PD-L1 were generated by introducing point mutations into the CDRs of the fully human Ab1 in order to reduce affinity. Briefly, residues in the CDRs in close proximity to the PD-L1 binding epitope were mutated to dissimilar amino acids. Four selected example residues are pictured in FIG. 1. For initial screening purposes, SG-559-xx antibodies were produced at ATUM bio using transient transfection in HEK293 cells.

For follow-up studies, antibodies were produced in-house according to the following protocol. Antibody variable and constant domains sequences were synthesized using non-template PCR. In short, the virtual gene sequence was converted into oligonucleotide sequences using Genewiz's bioinformatics tool. Oligonucleotides were synthesized, pooled and amplified using PCR. Full length amplicon from the PCR reaction was cloned into the vector and the product was then transformed into E. coli and unique colonies were isolated. Colonies were grown up overnight in liquid media and plasmid DNA isolated, purified, and sequence verified using Sanger sequencing. Light chains and heavy chains were cloned into pcDNA3.4 vectors.

A 1:1 ratio of antibody heavy chain and light chain vectors were diluted into ThermoFisher OptiPRO SFM medium with ExpiFectamine CHO transfection reagent. The DNA/transfection reagent was then added to an ExpiCHO culture in ThermoFisher ExpiCHO Expression medium and cultured for nine days with ExpiCHO enhancer added on day one and ExpiCHO feeds added on days one and two. Culture was harvested by centrifugation and 0.2 um filtration or by depth filtration using Millipore X0HC and D0HC pods followed by 0.2 um filtration.

GE HiTrap mAb Select SuRe columns were used for the purification of each IgG. Prior to elution, the resin was washed with 5CV PBS+0.1% Triton, 5CV PBS+0.5M NaCl, and 7.5CV of PBS. The IgG was eluted using 100 mM Acetic Acid pH3 Buffer. The sample was buffer exchanged using a 26/60 HiPrep Desalt columns into PBS. The sample underwent a final polishing step of HiPrep Superdex 200 26/600 column, run in PBS. The sample was then filter sterilized before a sample was taken for the characterization. Characterization included A280 concentration, aSEC HPLC, aHIC HPLC, and reduced PLRP-MS (QToF).

Biolayer Interferometry

Biolayer interferometry was performed using an Octet Red 384 system (ForteBio) to determine the binding affinity of the SG-559-xx antibodies. Anti-Human Fab-CH1 (FAB2G) biosensors (ForteBio) were loaded for 100 s with 4 µg/mL SG-559-xx antibodies. After subsequent baselining steps, human PD-L1 (Acro Biosciences) at concentrations ranging from 500 nM to 0.69 nM (1×PBS pH 7.4 with 1% casein, 0.2% Tween-20) was incubated with the loaded probes for 150 s for the association step. This was followed by a dissociation step in the same buffer lacking human PD-L1 for 1000 s. $k_{association}$ and $k_{dissociation}$ were fit to the resulting binding curves according to established methods.

Production of Antibody-Drug Conjugates (ADCs)

SG-559-xx antibodies were conjugated to MDpr-PEG (12)-gluc-MMAE with an average drug to antibody ratio (DAR) of 8 as described in US20180092984. SG-559-xx antibodies were conjugated to vc-MMAE with an average DAR of 4 as described in US20050238649. SG-559-xx antibodies were conjugated to MP-PEG8-VKG-Camptothecin with an average DAR of 8 as described in PCT/US2019/025968 (filed Apr. 5, 2019).

In Vitro Cytotoxicity Assay

Cell lines were plated 24 h prior to antibody-drug conjugate (ADC) treatment to allow for cells to acclimate. Where indicated, 500 IU/mL of interferon-γ was also added at this time to induce PD-L1 expression. Cells were then treated with the indicated doses of ADC and incubated for 96 hours at 37° C. Other PD-L1 directed antibodies as well as isotype controls were included as ADCs for comparison. Cell viability for the cell lines was measured using CellTiter-Glo (Promega Corporation, Madison, WI) according to the manufacturer's instructions. Briefly, cells were incubated for 30 minutes at room temperature with the CellTiter-Glo reagent and luminescence was measured using an Envision plate reader (Perkin Elmer, Waltham, MA). Results are reported as ×50, the concentration of compound needed to yield a 50% reduction in viability compared to untreated cells.

Internalization Assay

Internalization of PD-L1 directed antibodies was performed using FabFluor pH sensitive conjugates on an Incucyte (Sartorius). Antibodies were conjugated to a pH sensitive dye which has increasing fluorescent signal as pH decreases from the cell surface and into the endosomal/lysosomal compartments. Adherent cells were plated 24 h (with 500 IU/mL of interferon-γ to induce PD-L1 expression) prior to incubation with these conjugates. Suspension cells were plated 3 h prior to incubation with these conjugates. Cells were then given 0.5 µg/mL of the indicated dye-antibody conjugate and allowed to incubate for 48 h. Using Incucyte S3 software (Sartorius), the total integrated intensity of fluorescent signal was normalized to the confluence % per well per time point. Results are reported as the area under the curve of the normalized integrated intensity vs. time.

In Vivo Activity Study

Nude mice were inoculated subcutaneously with $5.0 \times 10^6$ BxPC3 pancreatic adenocarcinoma cells or $1.0 \times 10^6$ EBC-1 NSCLC cells. NSG mice were inoculated subcutaneously with $5.0 \times 10^5$ MDA-MB-231 triple-negative breast cancer cells. SCID mice were inoculated subcutaneously with $1.0 \times 10^6$ Karpas 299 ALCL cells or $1.0 \times 10^6$ Calu-1 NSCLC cells. Tumor growth was monitored with calipers and the mean tumor volume was calculated using the formula ($0.5 \times$ [length$\times$width$^2$]). When the mean tumor volume reached approximately 100 mm$^3$, mice were untreated or dosed intraperitoneally as indicated with ADC. Unconjugated antibodies and vc-MMAE ADCs were dosed weekly for a total of three doses. MP-PEG8-VKG-Camptothecin ADCs were dosed once only. Mice were euthanized when tumor volumes reached approximately 750 mm$^3$. For immune characterization study in Karpas 299 bearing animals, mean tumor volume was allowed to reach 200 mm$^3$. These mice were then treated with a single dose of unconjugated antibody or ADC and euthanized six days later. Tumors were characterized ex vivo by immunohistochemistry and cytokine analysis (Luminex). All animal procedures were performed under a protocol approved by the Institutional Animal Care and Use Committee in a facility accredited by the Association for Assessment and Accreditation of Laboratory Animal Care.

PD-L1 Blockade

In vitro assessment of PD-L1 blockade was conducted using the PD-1/PD-L1 Blockade Bioassay (Promega Corporation) according to the manufacturer's instructions. Briefly, PD-L1+ aAPC/CHO-K1 cells were plated and allowed to acclimate for 16 hours. Indicated concentrations of antibody or ADC are then added to the plated cells, followed by PD-1+ Effector cells. In the absence of PD-1/PD-L1 signaling, interaction between the aAPC/CHO-K1 cells and effector cells results in a bioluminescent signal. Therefore, more effective inhibition of PD-1/PD-L1 interaction results in a higher luminescent signal, quantified as fold induction over untreated cells. PD-1 binding antibody (Promega Corporation) was included as a positive control, and a non-binding isotype antibody was included as a negative control.

Immunotoxicity in a Human APC Model Stimulated with IFNγ to Upregulate PD-L1

Antibody or ADC immunotoxicity towards human antigen presenting cells in vitro was measured using human antigen presenting cells (APC) stimulated with interferon-γ

(IFNγ) followed by treatment with any of the antibodies or ADCs described herein. Human APCs were stimulated in vitro with IFNγ (R&D Systems) at 500 IU/mL for 24 hours to upregulate PD-L1 prior to treatment with SG-559-xx ADCs. Immunotoxicity was calculated as the percentage of viability of untreated APCs at different antibody or ADC concentrations.

Immune Response Inhibition in a Human APC Model

Immune response inhibition was measured using human antigen presenting cells (APC) stimulated with lipopolysaccharide (LPS) followed by treatment with any of the antibodies or ADCs descried herein. Human APCs were stimulated in vitro with IFNγ (R&D Systems) at 500 IU/mL for 24 hours to upregulate PD-L1. Human APCs were then treated with SG-559-xx ADCs as indicated for 24 hours. Human APCs were then stimulated in vitro with LPS (Sigma Aldrich) at 100 ng/mL for 48 hours. Response to LPS was measured by flow cytometry staining of MHC Class II and CD86 (Biolegend). Strength of immune function was calculated as the fold change in MHC Class II or CD86 in response to LPS stimulation in APCs at different antibody or ADC concentrations.

Deglycosylation of Human PD-L1 Using PNGase F

In order to generate a deglycosylated hPD-L1, human PD-L1 was treated with a PNGase F enzyme (New England Biolabs) combined with a denaturation protocol. PNGase F catalyzes the cleavage of N-linked oligosaccharides between the innermost GlcNAc and asparagine residues of high mannose, hybrid and complex oligosaccharides from N-linked glycoproteins. Human PD-L1 was subjected to the denaturing protocol in the absence of PNGase F to provide a reaction control. The deglycosylation protocol included combining human PD-L1 (Acro Biosciences) with Rapid PNGase F buffer, heating the human PD-L1 at 75° C. for 5 minutes, chilling the denatured human PD-L1 on ice, adding PNGase F, and incubating at 37° C. overnight. Glycosylation status was confirmed with mass spectrometry.

Biolayer interferometry was performed using an Octet Red 384 system (ForteBio) to determine the binding affinity of the SG-559-xx antibodies or ADCs to the glycosylated or deglycosylated PD-L1. After subsequent baselining steps, glycosylated human PD-L1 and deglycosylated human PD-L1 at concentrations ranging from 500 nM to 0.69 nM (1×PBS pH 7.4 with 1% BSA, 0.2% Tween-20) were incubated with the loaded probes for 150 s for the association step. This was followed by a dissociation step in the same buffer lacking human PD-L1 for 1000 s. $k_{association}$ and $k_{dissociation}$ were fit to the resulting binding curves according to established methods.

Results

Example 1: Design and Characterization of SG-559-xx Antibodies

Seventeen SG-559-xx antibodies were generated from the parental Ab1 antibody as described in the methods. The CDRs containing the mutations of these antibodies are denoted in Table 1. Sixteen of these antibodies were evaluated for their monovalent binding affinity to hPD-L1 by biolayer interferometry in comparison to Ab1 (Table 2). The measured affinities of the SG-559-xx antibodies span a range of almost two orders of magnitude, with $K_D$ values from 4 nM to 297 nM.

TABLE 1

SG-559-XX Variant Sequences

| SG-559-XX VARIANT | MUTATED CDR | SEQ ID NO. |
|---|---|---|
| SG-559-01 | HC CDR1 | 13 |
| SG-559-02 | LC CDR1 | 26 |
| SG-559-03 | LC CDR3 | 38 |
| SG-559-04 | HC CDR3 | 45 |
| SG-559-05 | HC CDR2 | 49 |
| SG-559-06 | HC CDR2 | 50 |
| SG-559-07 | HC CDR2 | 51 |
| SG-559-08 | HC CDR2 | 52 |
| SG-559-09 | HC CDR2 | 53 |
| SG-559-10 | HC CDR3 | 54 |
| SG-559-11 | HC CDR3 | 55 |
| SG-559-12 | LC CDR3 | 56 |
| SG-559-13 | LC CDR3 | 57 |
| SG-559-14 | LC CDR3 | 58 |
| SG-559-15 | LC CDR3 | 59 |
| SG-559-16 | LC CDR3 | 60 |
| SG-559-17 | LC CDR3 | 61 |

TABLE 2

SG-559-XX Binding Affinities

| Antibody | $K_D$ (nM) | $K_{ASSOC}$ (×10$^5$ M$^{-1}$S$^{-1}$) | $K_{DISSOC}$ (×10$^3$ S$^{-1}$) |
|---|---|---|---|
| AB1 | 2.7 | 5.50 | 1.50 |
| SG-559-01 | 10.0 | 4.50 | 4.50 |
| SG-559-02 | 33.3 | 4.20 | 14.0 |
| SG-559-03 | 24.5 | 4.90 | 12.0 |
| SG-559-04 | 25.6 | 3.90 | 10.0 |
| SG-559-05 | 118.8 | 3.57 | 42.4 |
| SG-559-06 | 79.9 | 3.13 | 25.0 |
| SG-559-07 | 10.0 | 2.85 | 2.84 |
| SG-559-08 | 66.6 | 3.29 | 21.9 |
| SG-559-09 | 25.5 | 2.60 | 6.64 |
| SG-559-10 | 287.8 | 4.10 | 118 |
| SG-559-11 | ND | ND | ND |
| SG-559-13 | 4.3 | 3.81 | 1.62 |
| SG-559-14 | 8.9 | 3.99 | 3.55 |
| SG-559-15 | 7.5 | 4.62 | 3.47 |
| SG-559-16 | 24.7 | 3.86 | 9.53 |
| SG-559-17 | 12.5 | 4.56 | 5.70 |

Example 2: In Vitro Cytotoxicity

The cytotoxicity of the SG-559-xx antibodies as ADCs was evaluated as described in the methods against cancer cell lines expressing PD-L1, including 786-0, BxPC3, ES-2, MDA-MB-231, Karpas 299, and L540cy. In some experiments, SU-DHL-4 (PD-L1 negative cancer cell line) was included as a control. An initial screen of fifteen SG-559-xx ADCs (not including the two with the lowest affinity) with MDpr-PEG(12)-gluc-MMAE payloads (DAR 8) demonstrated that several SG-559-xx antibodies exhibited significantly improved cytotoxicity over the parental Ab1 (FIGS. 2A-2F).

Four SG-559-xx antibodies which consistently displayed the highest potency in the initial screen were additionally characterized as vc-MMAE and MP-PEG8-VKG-Camptothecin ADCs (Table 3) for their potency. In most cell lines tested, these ADCs were significantly more potent than Ab1. They also did not have activity in an antigen-negative cell line (SU-DHL-4), suggesting that this was not due to non-specific binding.

TABLE 3

SG-559-XX x50 Values (ng/mL)

| CELL LINE: | 786-O | BXPC3 | MDA-MB-231 | KARPAS 299 | L540CY | SU-DHL-4 |
|---|---|---|---|---|---|---|
| AB1 - VC-MMAE | >3000 | 642 | 308 | 43.2 | >3000 | >3000 |
| SG-559-01 - VC-MMAE | >3000 | 23 | 45.6 | 2.56 | 24 | >3000 |
| SG-559-02 - VC-MMAE | >3000 | 19.1 | 26 | 4.44 | 26 | >3000 |
| SG-559-03 - VC-MMAE | >3000 | 16.4 | 22.9 | 4.14 | 20.9 | >3000 |
| SG-559-04 - VC-MMAE | >3000 | 17.3 | 24.3 | 3.42 | 33.1 | >3000 |
| ATEZOLIZUMAB - VC-MMAE | >3000 | >3000 | >3000 | >3000 | >3000 | >3000 |
| AB1 - MP-PEG8-VKG-CAMPTOTHECIN | 210 | 1680 | 102 | 2249 | 147 | >3000 |
| SG-559-01 - MP-PEG8-VKG-CAMPTOTHECIN | 468 | 54.7 | 13.8 | 3.05 | 3.51 | >3000 |
| SG-559-02 - MP-PEG8-VKG-CAMPTOTHECIN | 283 | 20.1 | 10.2 | 6.72 | 9.97 | >3000 |
| SG-559-03 - MP-PEG8-VKG-CAMPTOTHECIN | 1378 | 62.5 | 15.1 | 12.2 | 13.8 | >3000 |
| SG-559-04 - MP-PEG8-VKG-CAMPTOTHECIN | 190 | 23.3 | 7.89 | 5.95 | 10.7 | >3000 |
| ATEZOLIZUMAB - MP-PEG8-VKG-CAMPTOTHECIN | >3000 | >3000 | >3000 | >3000 | >3000 | >3000 |

Example 3: Internalization

Figure 3A:
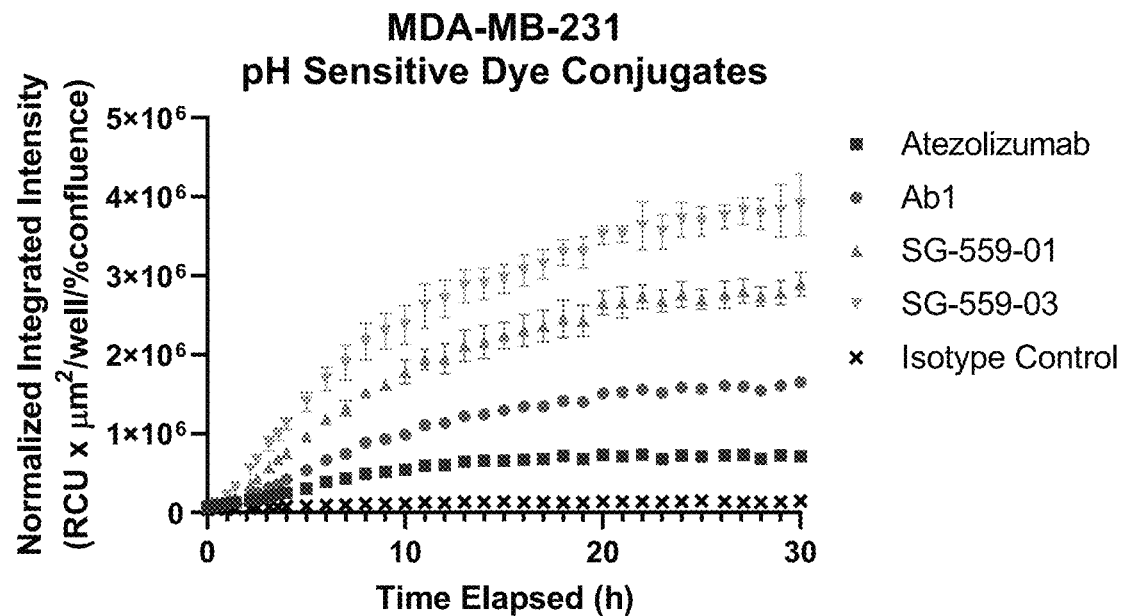
FIGS. 3A-3B show internalization of SG-559-01 and SG-559-03 compared to control antibodies.
Figure 3B:
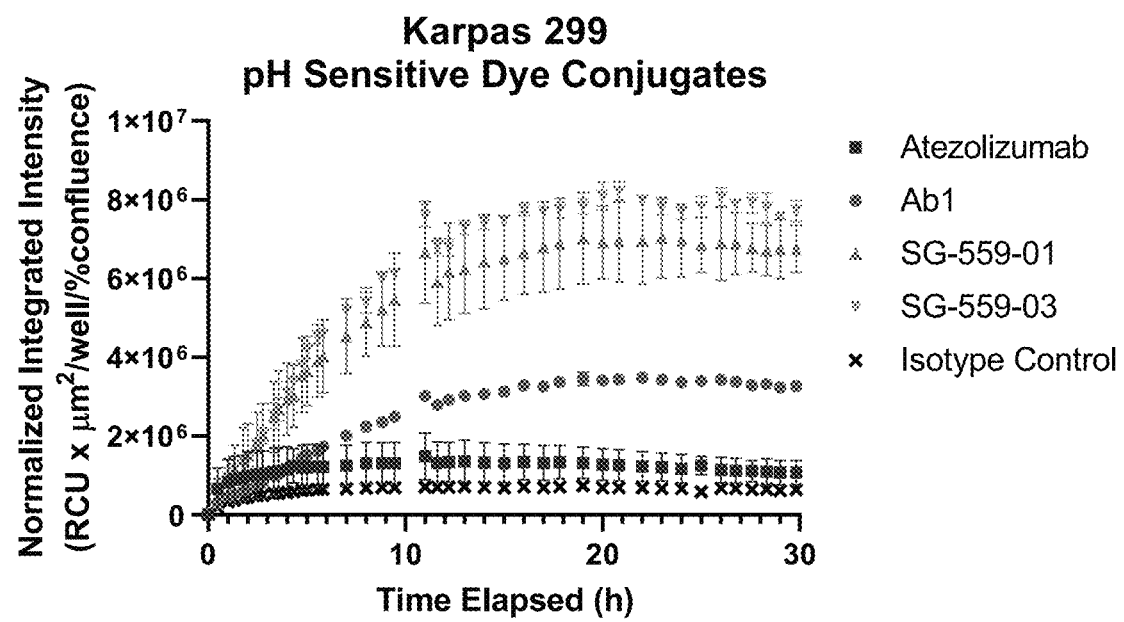

To corroborate the cytotoxicity results, the internalization of SG-559-01 and SG-559-03 was further examined using the Incucyte imaging system and pH sensitive dye conjugates as described in the methods. The internalization of SG-559-01 and SG-559-03 was consistently higher across most cell lines tested. This was measured by the percent increase in the area under the curve (AUC) of normalized integrated intensity over time (Table 4). Example curves are shown for MDA-MB-231 (FIG. 3A) and Karpas 299 (FIG. 3B).

TABLE 4

SG-559-XX Internalization

| | PERCENT INCREASE OF AUC OVER AB1 | |
|---|---|---|
| | SG-559-01 | SG-559-03 |
| 786-O | 44% | 122% |
| A375 | 92% | 97% |
| BXPC3 | 87% | 149% |
| ES-2 | 11% | 38% |
| MDA-MB-231 | 77% | 140% |
| DEL | 89% | 152% |
| KARPAS 299 | 109% | 135% |
| L540CY | 76% | 81% |

Example 4: In Vivo Anti-Tumor Activity

Figure 4A:
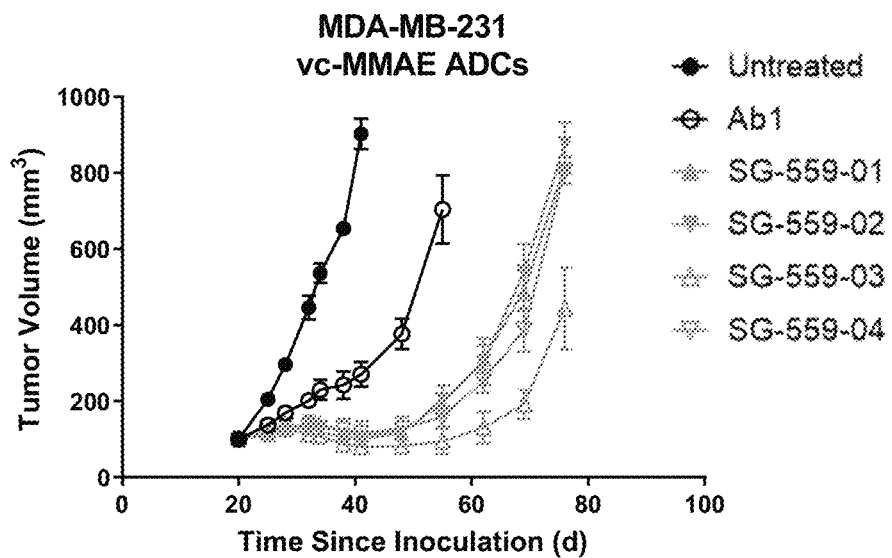
FIGS. 4A-4B shows anti-tumor activity of SG-559-xx ADCs in the MDA-MB-231 mouse model.
Figure 4B:
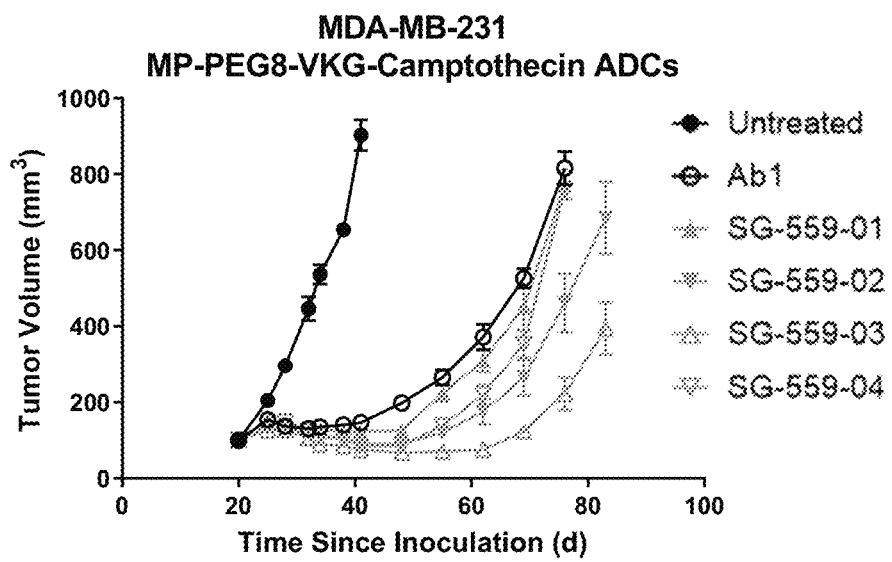
Figure 5A:
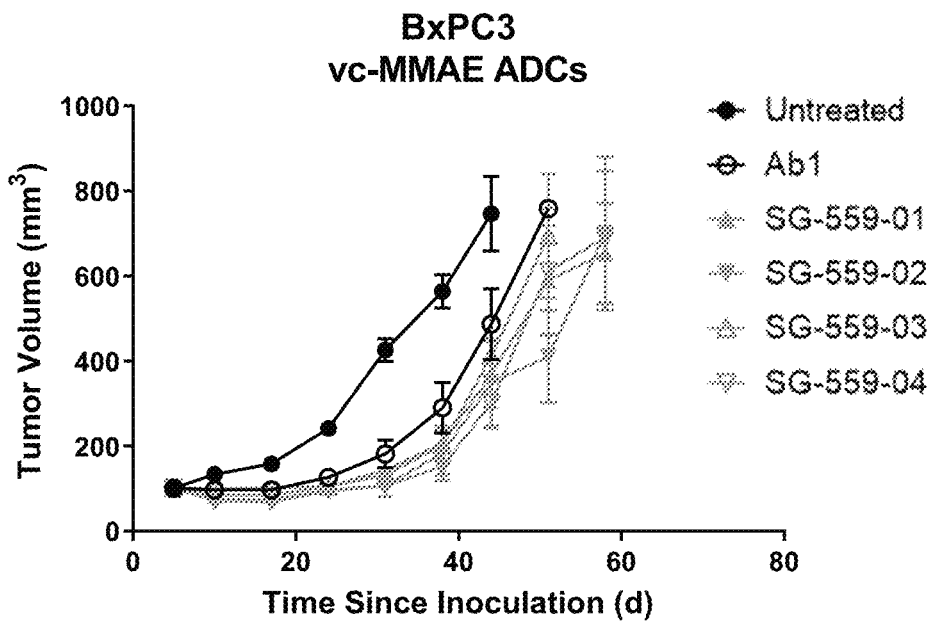
FIGS. 5A-5B shows anti-tumor activity of SG-559-xx ADCs in the BxPC3 mouse model.
Figure 5B:
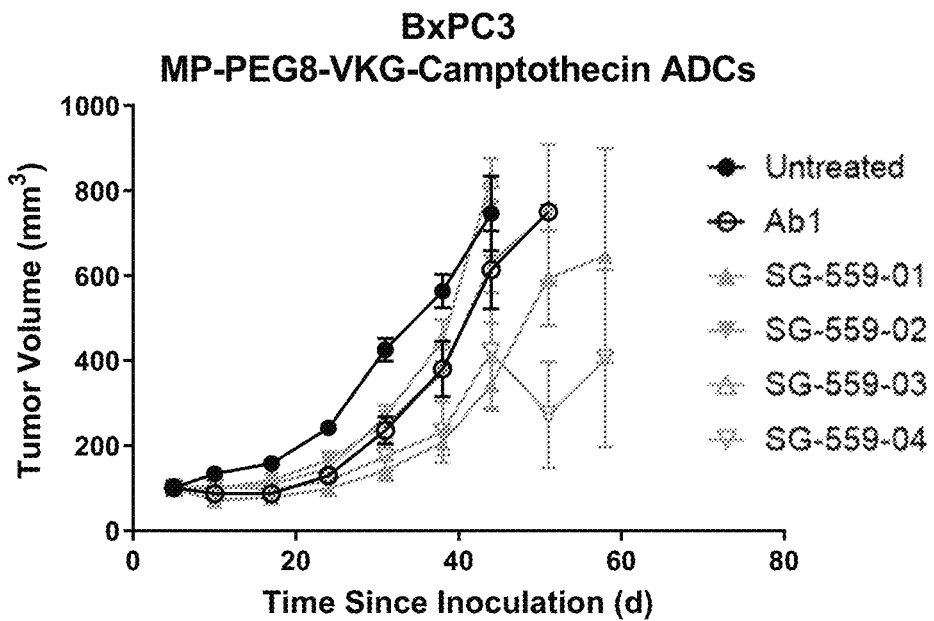

The four SG-559-xx antibodies which were characterized for in vitro screening were also tested for anti-tumor efficacy in two mouse xenograft models. In the MDA-MB-231 model, the SG-559-xx antibodies as ADCs exhibited significant anti-tumor activity with two drug-linkers (FIGS. 4A-4B). In the BxPC3 model, the SG-559-xx antibodies as ADCs exhibited modest anti-tumor activity (FIGS. 5A-5B). In almost all cases, the SG-559-xx ADCs were more efficacious than the Ab1 ADCs, suggesting that the in vitro phenotype observed translates to an in vivo setting.

Figure 6A:
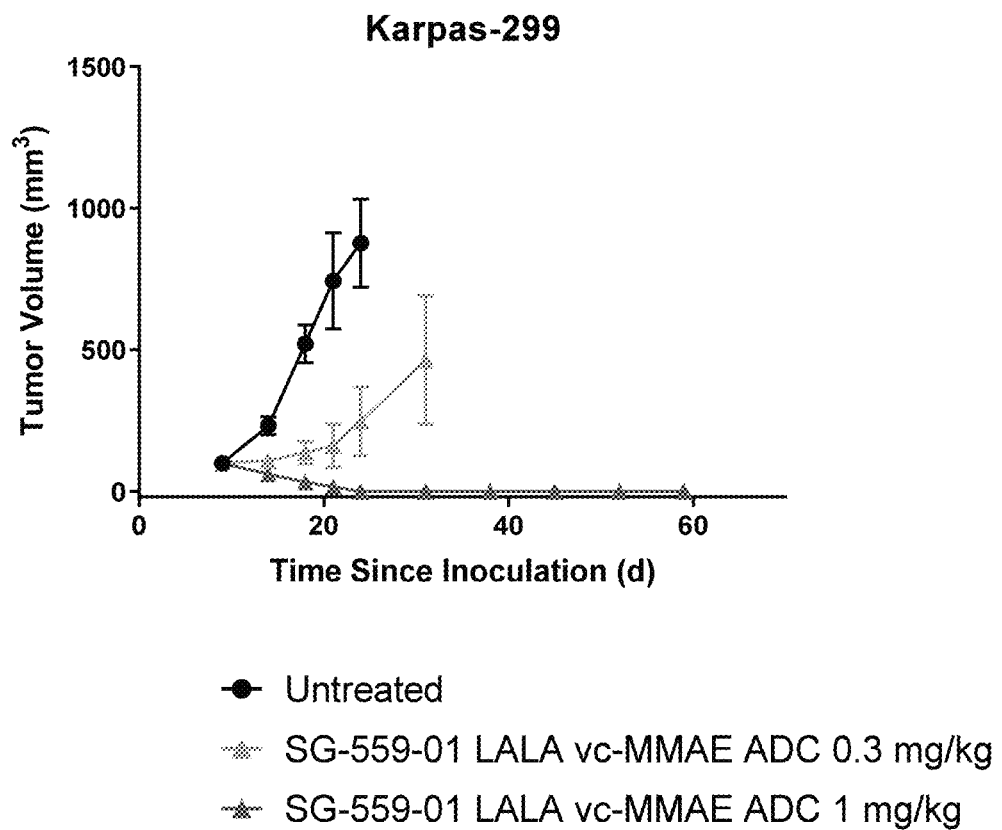
FIGS. 6A-6B shows anti-tumor activity of SG-559-01 LALA ADCs in the Karpas 299 mouse model.
Figure 6B:
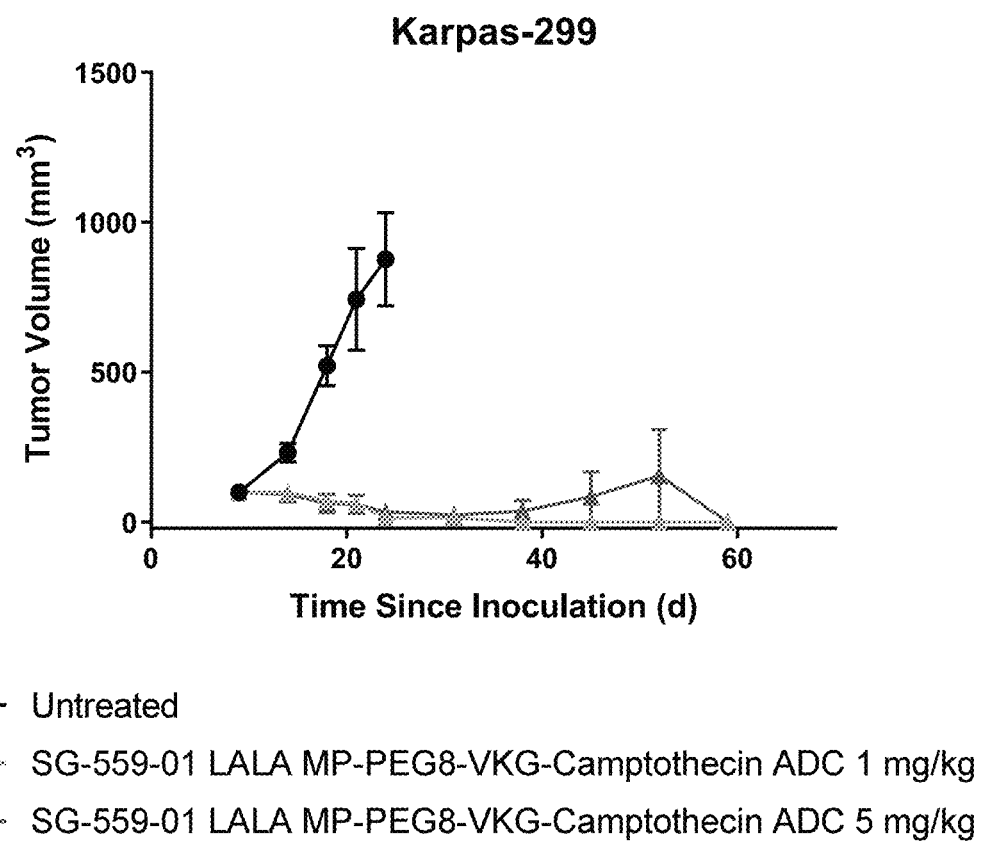
Figure 7:
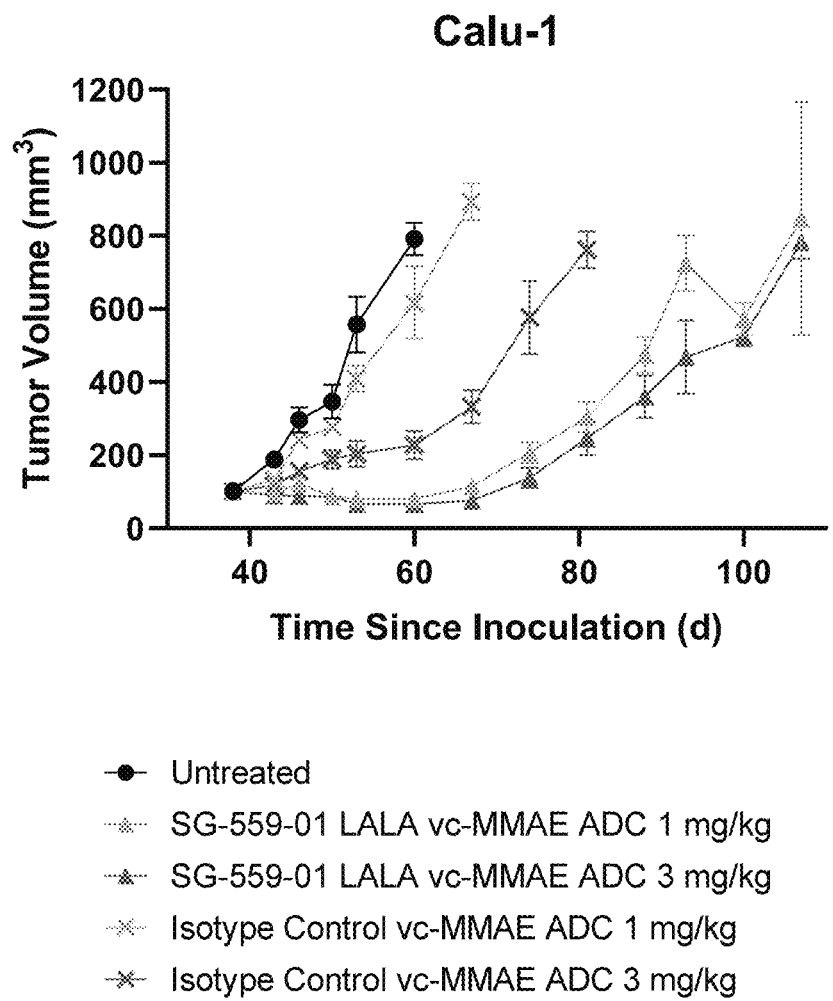
FIG. 7 shows anti-tumor activity of SG-559-01 LALA ADCs in the Calu-1 mouse model.
Figure 8A:
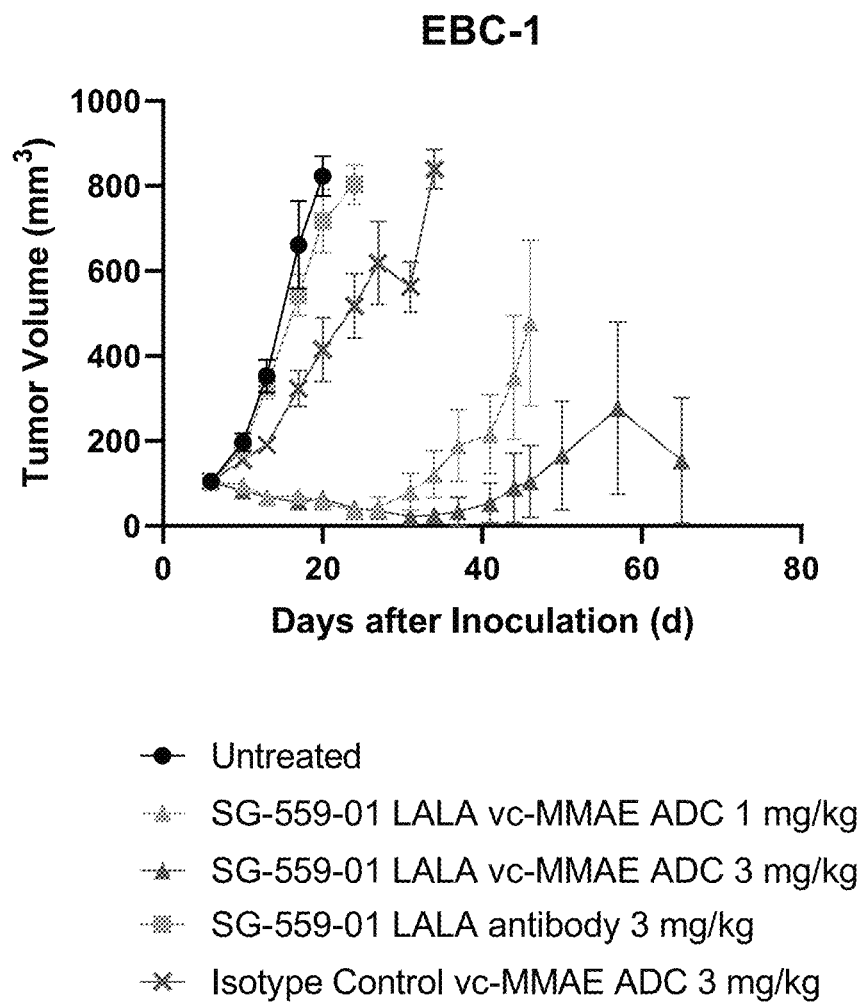
FIGS. 8A-8B shows anti-tumor activity of SG-559-01 LALA ADCs in the EBC-1 mouse model.
Figure 8B:
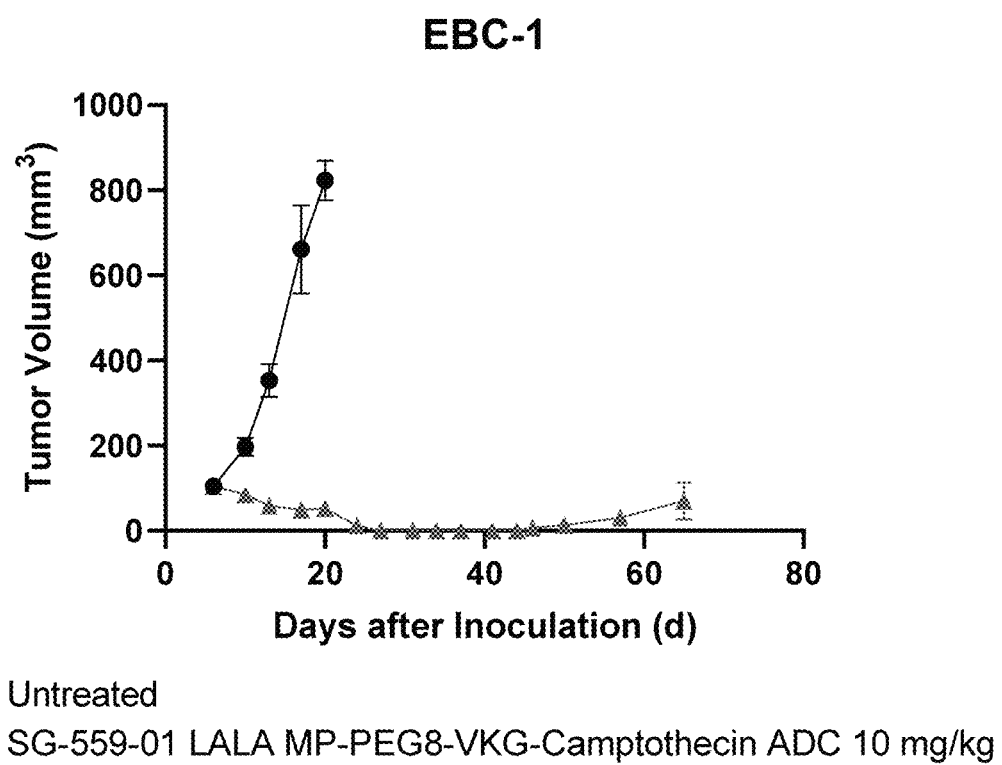

Anti-tumor efficacy was further observed in additional models using one of our most promising antibodies as an Fc effector function reduced variant (SG-559-01 LALA). The SG-559-01 LALA antibody as an ADC exhibited significant anti-tumor activity with one or two drug linkers in the Karpas 299 (FIGS. 6A-6B), Calu-1 (FIG. 7), and EBC-1 (FIGS. 8A-8B) models. Note that this activity is distinct from that of the unconjugated SG-559-01 LALA antibody.

Example 5: PD-L1 Blockade

Figure 9:
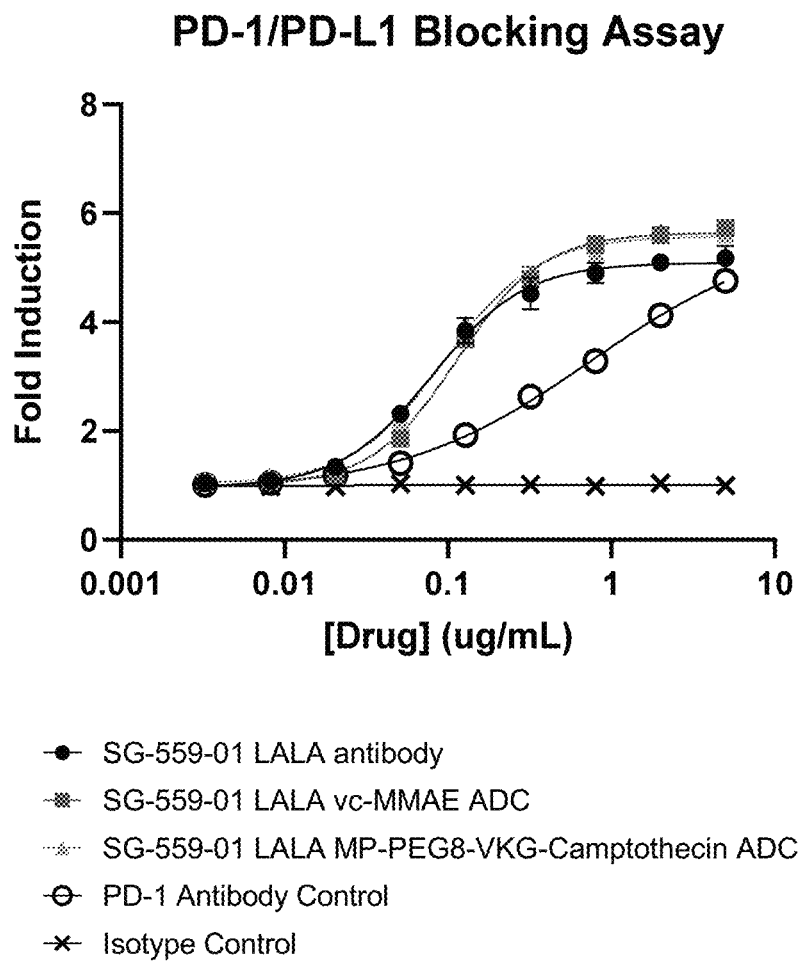
FIG. 9 shows in vitro PD-1/PD-L1 blocking activity of SG-559-01 LALA Antibody and ADCs.
Figure 10A:
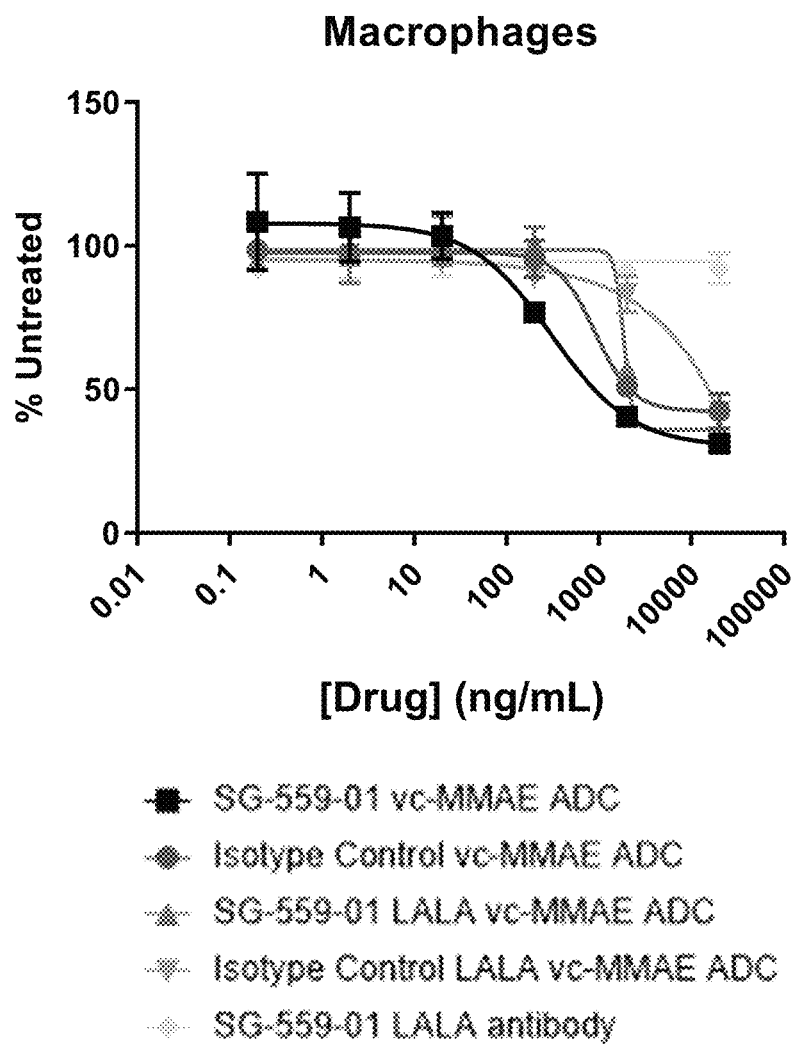
FIGS. 10A-10D show immunotoxicity of SG-559-01 and SG-559-01 LALA ADCs in a human APC model.
Figure 10B:
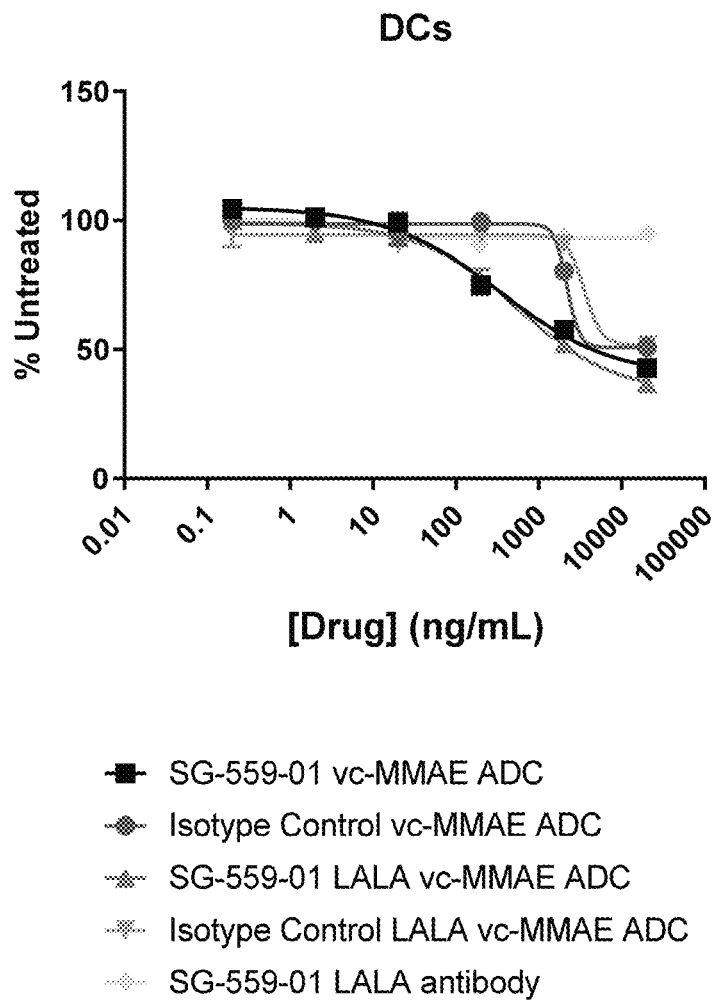
Figure 10C:
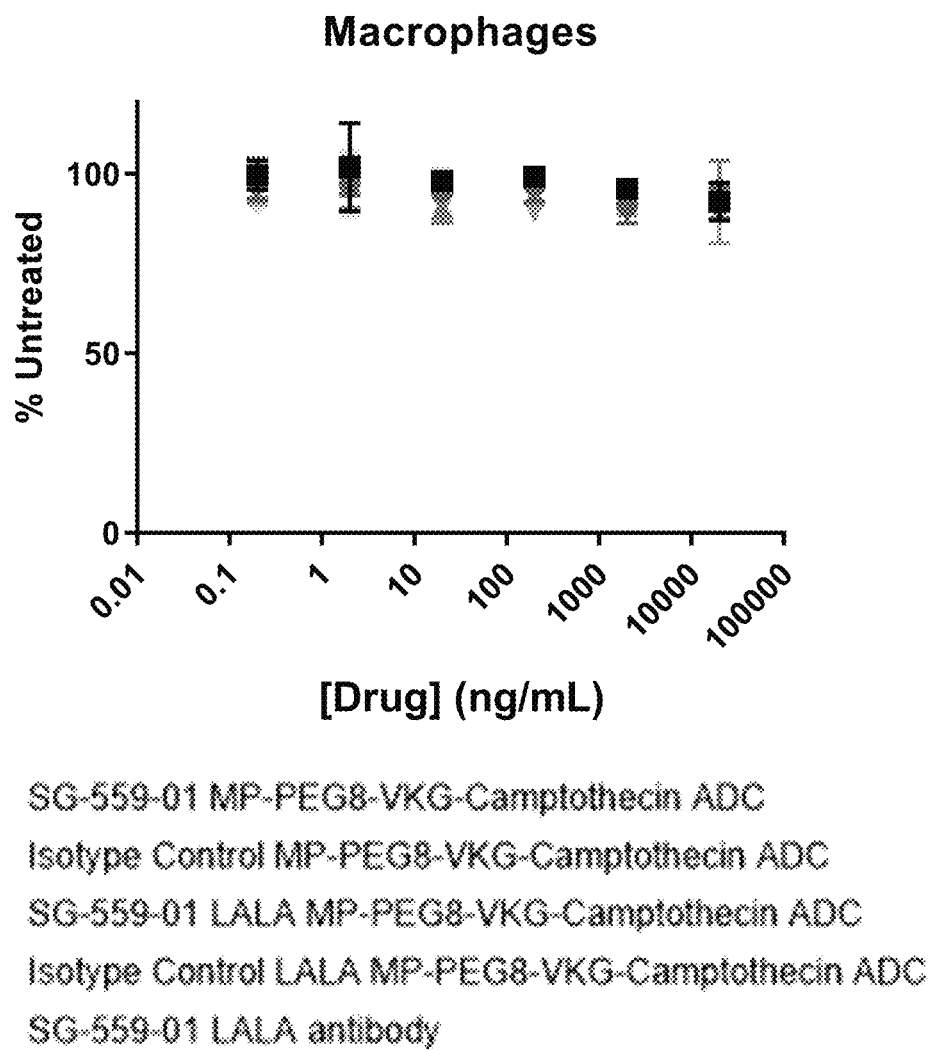
Figure 10D:
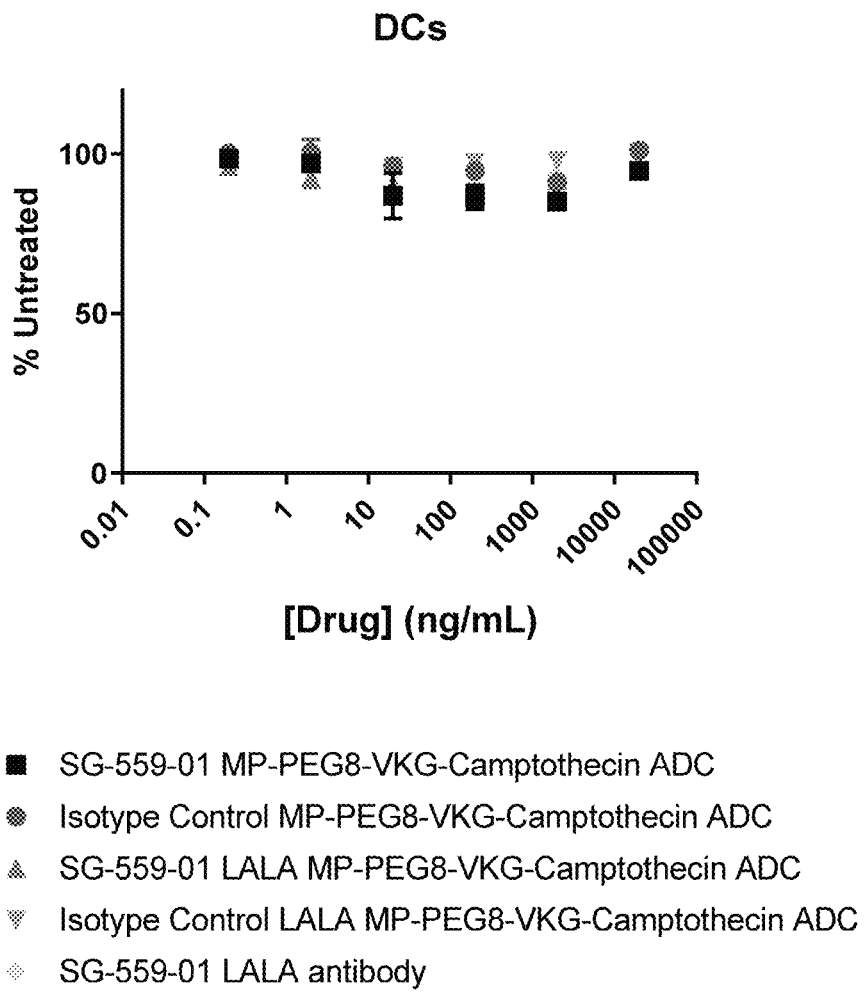
Figure 11A:
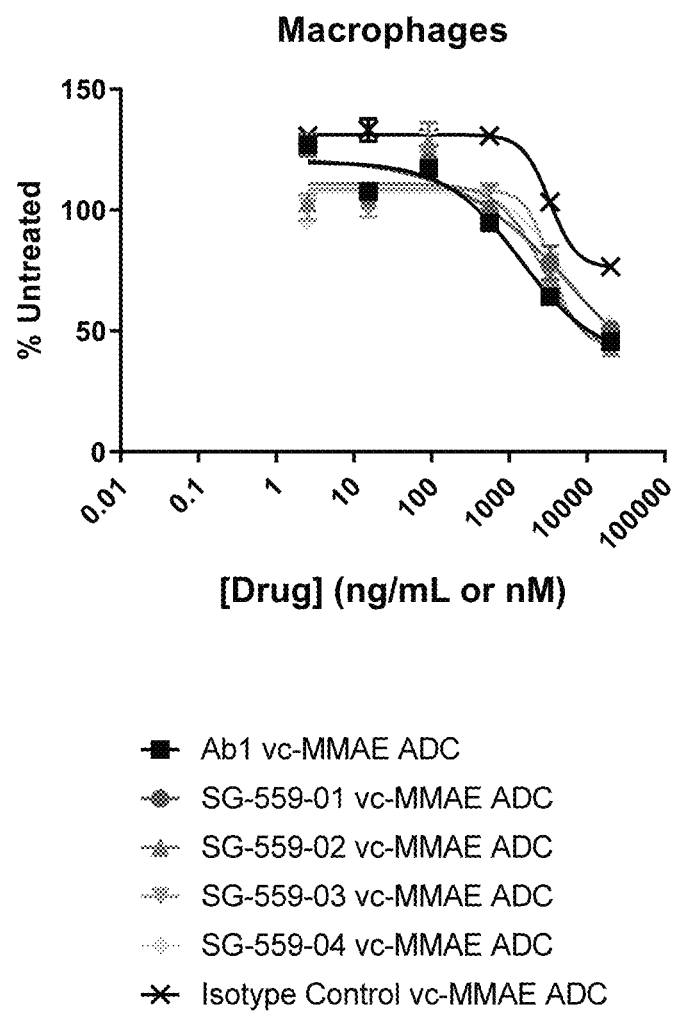
FIGS. 11A-11D show immunotoxicity of SG-559-xx ADCs in a human APC model.
Figure 11B:
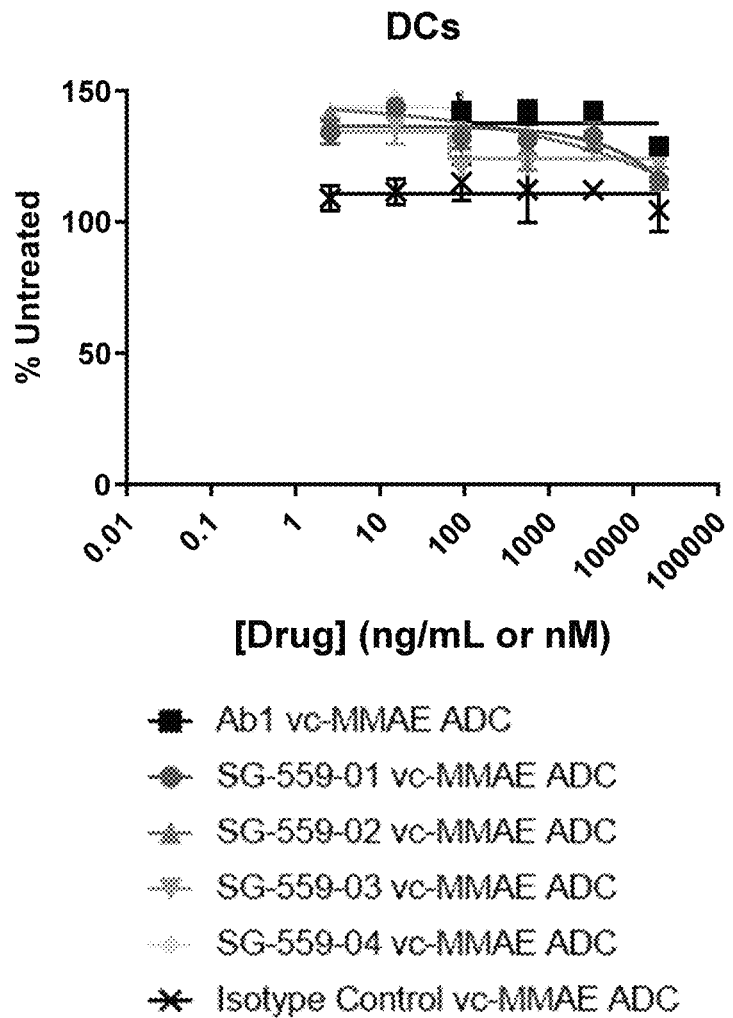
Figure 11C:
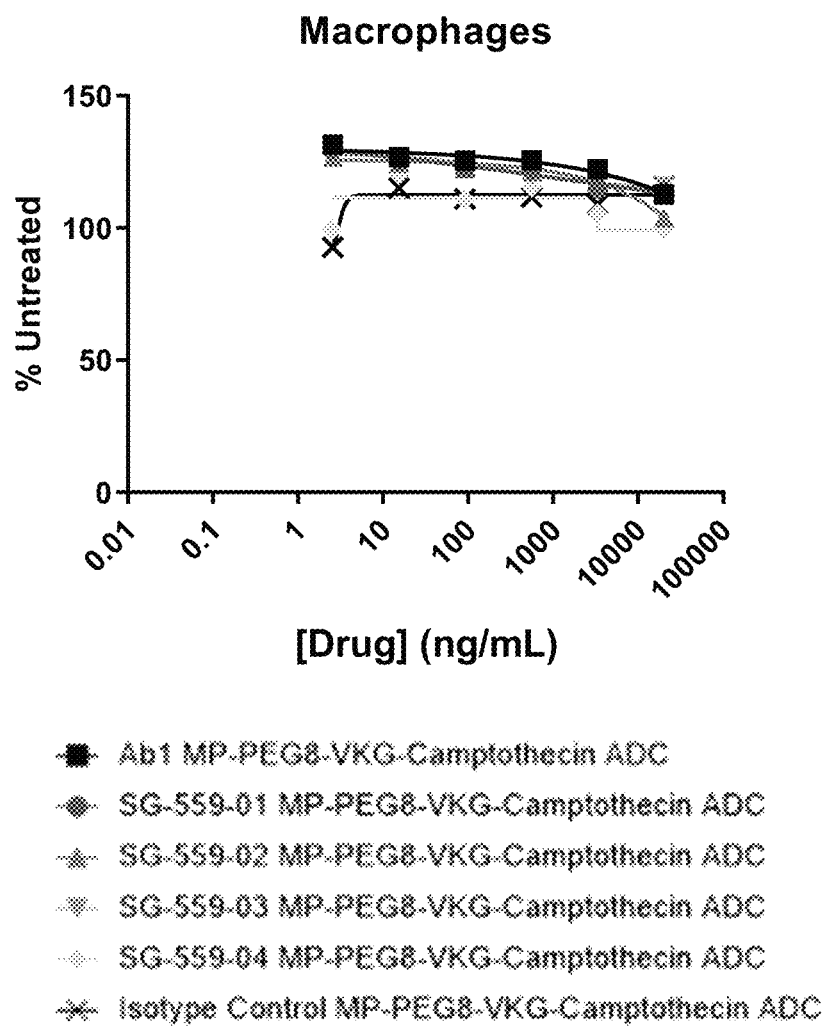
Figure 11D:
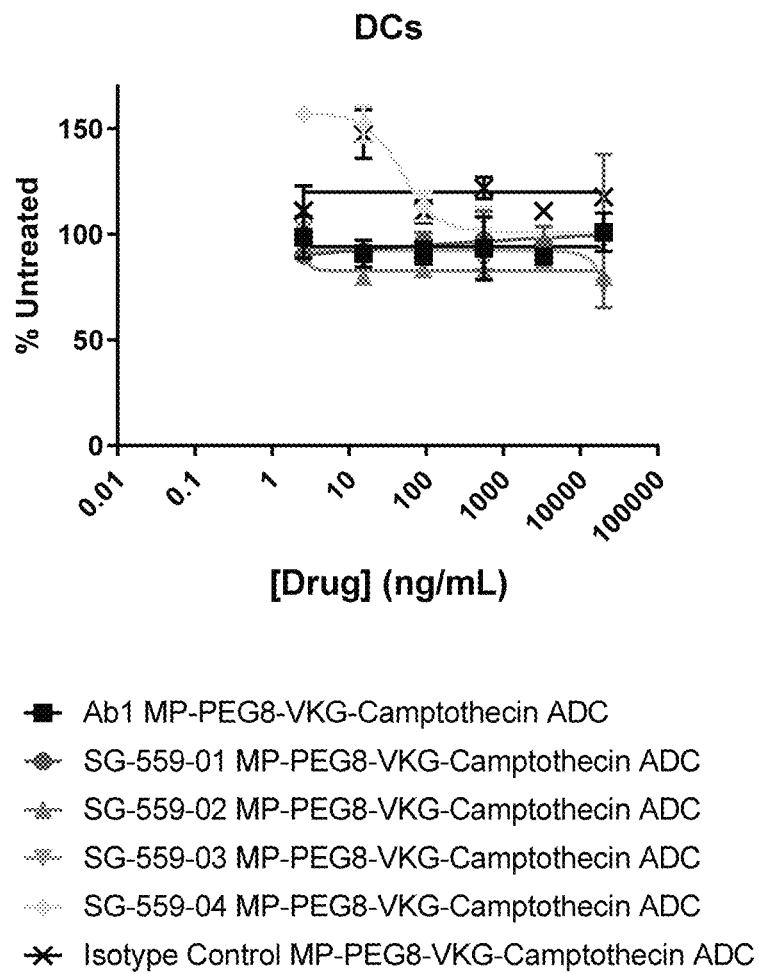

SG-559-01 LALA was further characterized for its ability to block the PD-1/PD-L1 checkpoint in vitro. Relative to a PD-1 antibody control, SG-559-01 is able to more effectively inhibit PD-1/PD-L1 signaling. Furthermore, unconjugated SG-559-01 LALA was on par with SG-559-01 LALA conjugated to two drug linkers, demonstrating that conjugation does not affect PD-1/PD-L1 blocking (FIG. 9).

Example 6: Immunotoxicity Towards Human APCs In Vitro

SG-559-01 and SG-559-01 LALA were assessed for immunotoxicity towards APCs (e.g., macrophages and dendritic cells (DC)). APCs were stimulated with IFNγ to upregulate PD-L1 prior to treatment as described in the methods. SG-559-01 LALA ADC exhibited immunotoxicity towards human APCs that were similar to or within one order of magnitude of isotype controls in both macrophages and DCs (FIGS. 10A-10D).

The four SG-559-xx antibodies which were characterized for in vitro screening were also tested for immunotoxicity against APCs (i.e., dendritic cells and macrophages). Immunotoxicity towards human APCs were similar to or within one order of magnitude for each of the SG-559-xx ADCs (FIGS. 11A-11D).

Example 7: Immune Response Inhibition

Figure 12A:
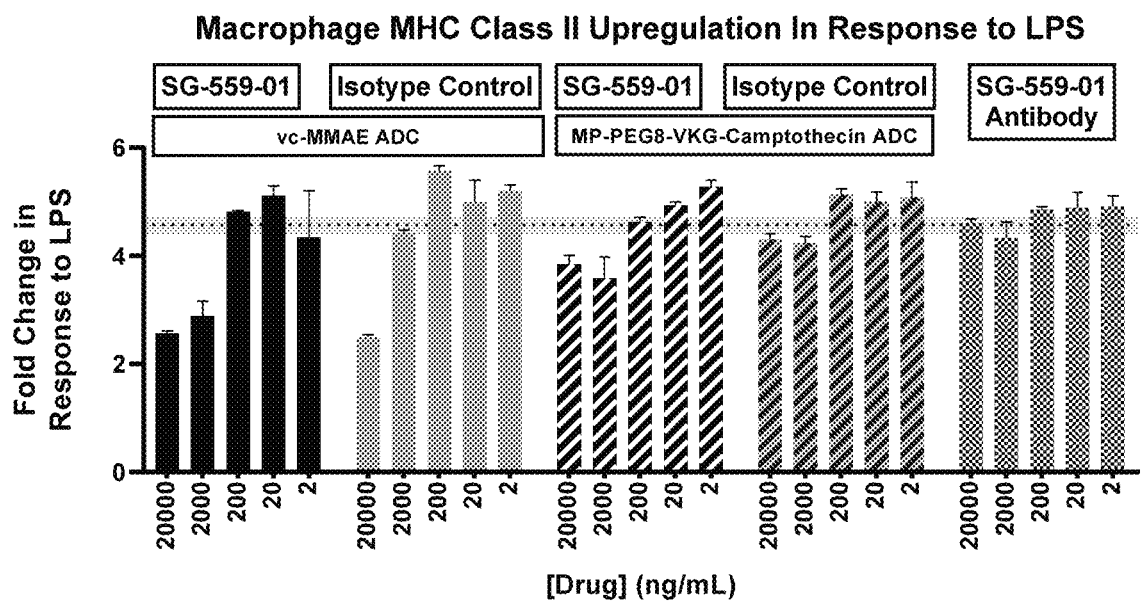
FIGS. 12A-12D show immune response to LPS stimulation of SG-559-01 ADC treated human APCs in vitro.
Figure 12B:
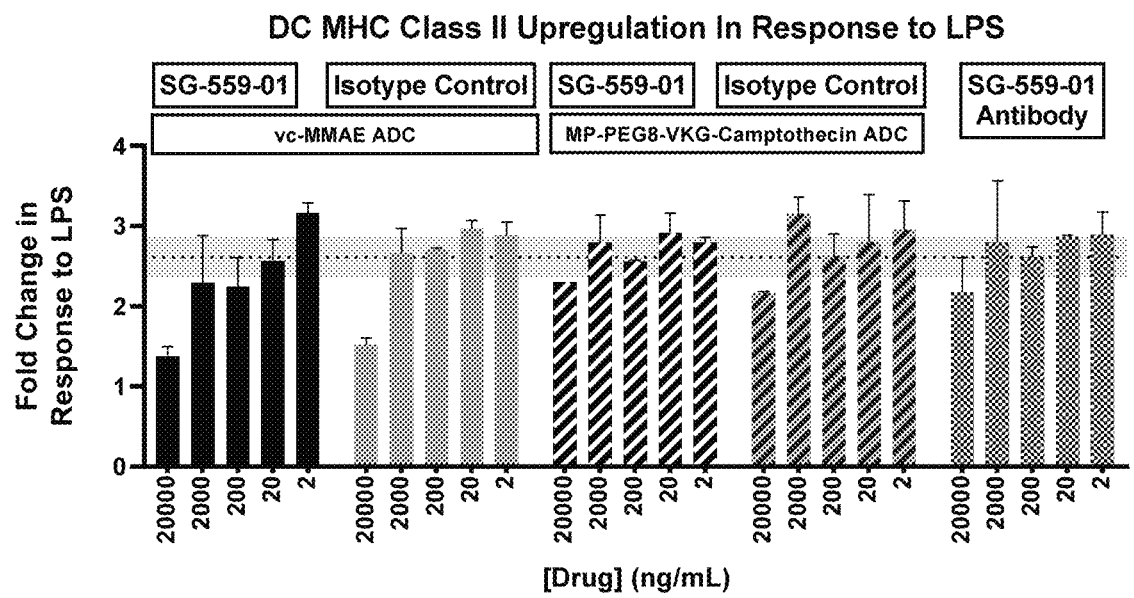
Figure 12C:
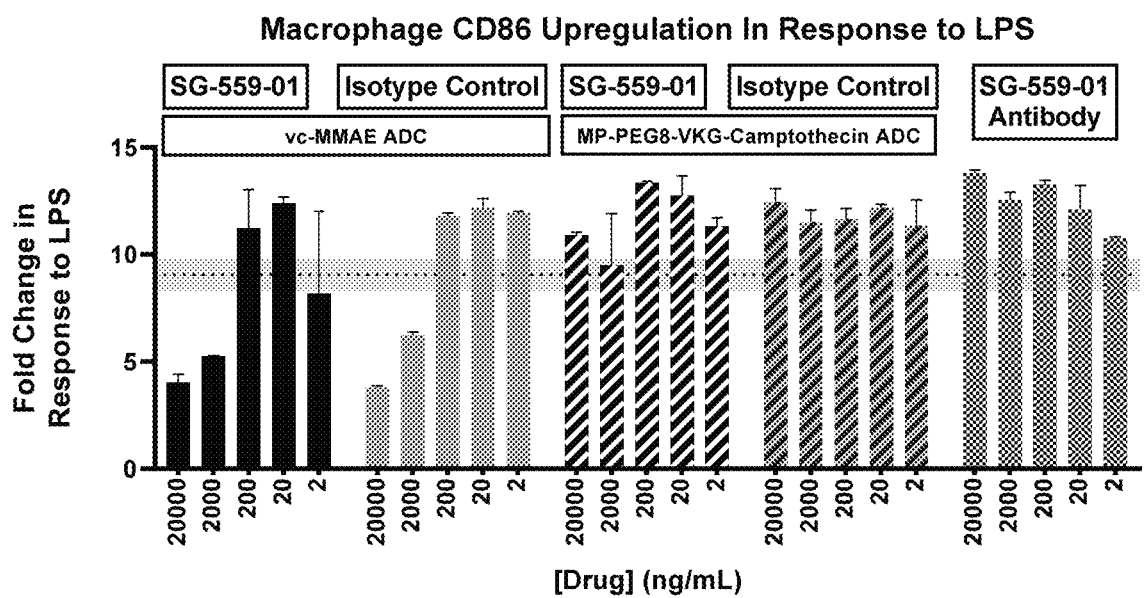
Figure 12D:
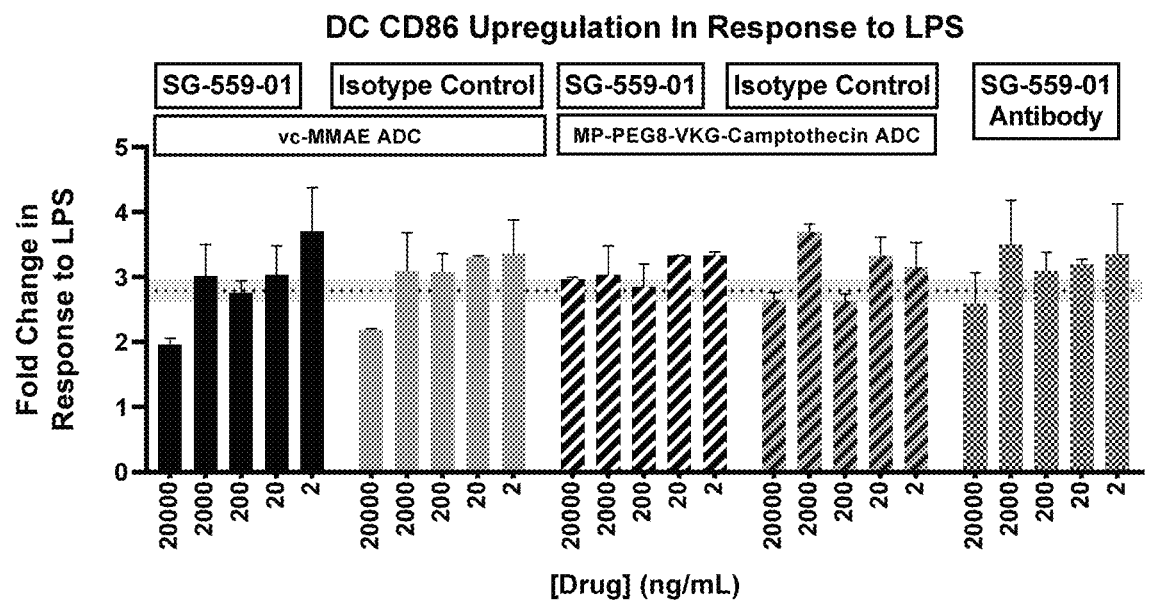

SG-559-01 ADC was further characterized by measuring immune response inhibition in human APCs treated with LPS. As described in the methods, in vitro human APCs were stimulated with LPS after ADC treatment and subsequent upregulation of MHC Class II and CD86 was quantified as a measure of immune response. Treatment with SG-559-01 ADCs resulted in immune response inhibition in a similar fashion, or within one order of magnitude of isotype controls, in both DCs and macrophages as measured by MHC Class II (FIGS. 12A-12B) and CD86 (FIGS. 12C-D).

Example 8: Increase Immune Infiltration

Figures 13A, 13B:
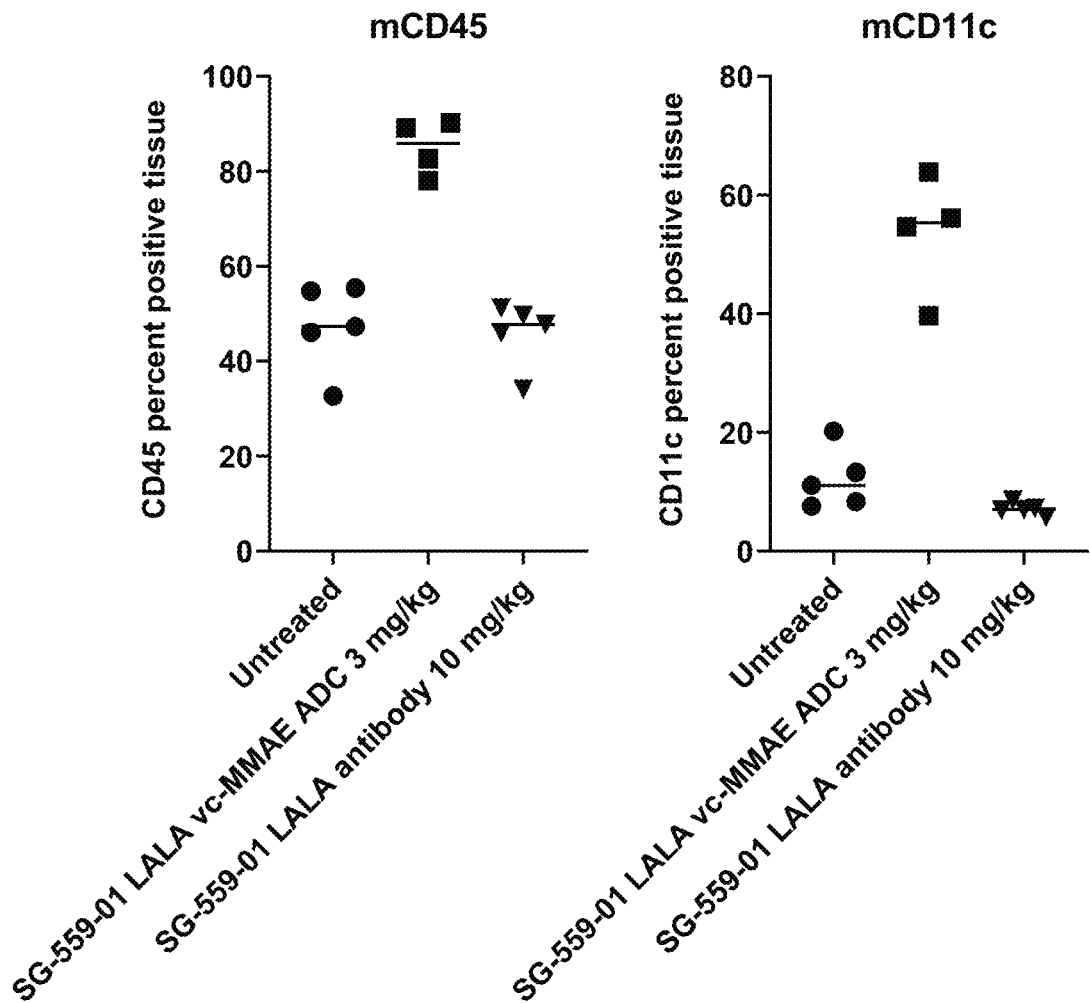
FIGS. 13A-13C show intratumoral immune cell infiltration in mice with Karpas 299 tumors treated with SG-559-01 LALA vc-MMAE ADC.
Figure 13C:
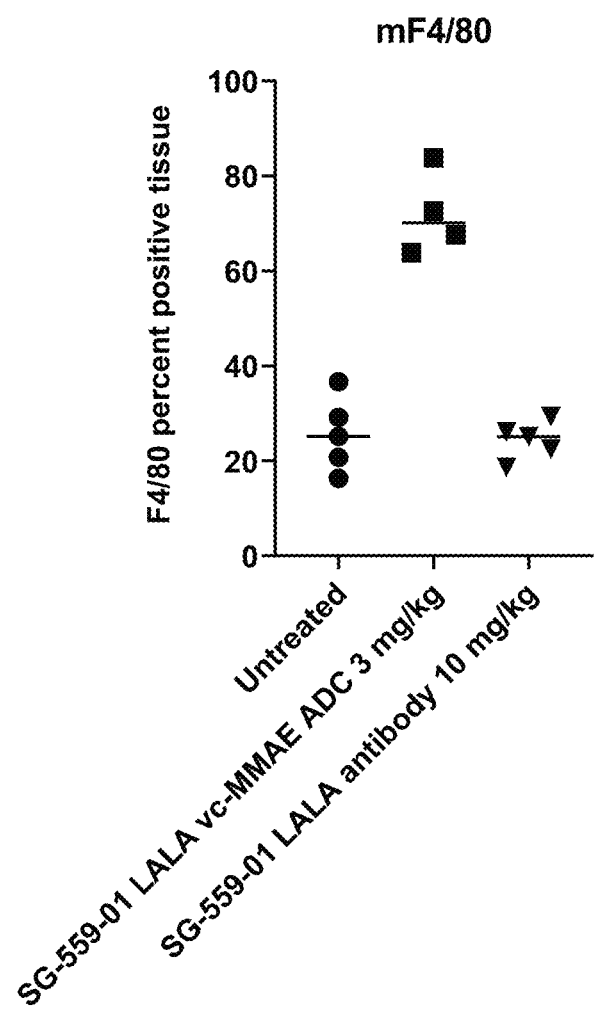

SG-559-01 LALA vc-MMAE ADC was further characterized by assessing immune infiltration in mice with Karpas 299 tumors. Mice bearing tumors were treated as indicated and tumors were characterized six days later. Relative to both the untreated control and SG-559-01 antibody, SG-559-01 vc-MMAE ADC induced immune infiltration in mice with Karpas 299 tumors (FIGS. 13A-C). FIG. 13A shows increase in mCD45+ cells (pan-leukocyte marker). FIG. 13B shows increase in mCD11c+ cells (marker for dendritic cells and a subset of macrophages). FIG. 13C shows increase in mF4/80+ cells (macrophage marker).

Example 9: Inflammatory Cytokine Response

Figure 14A:
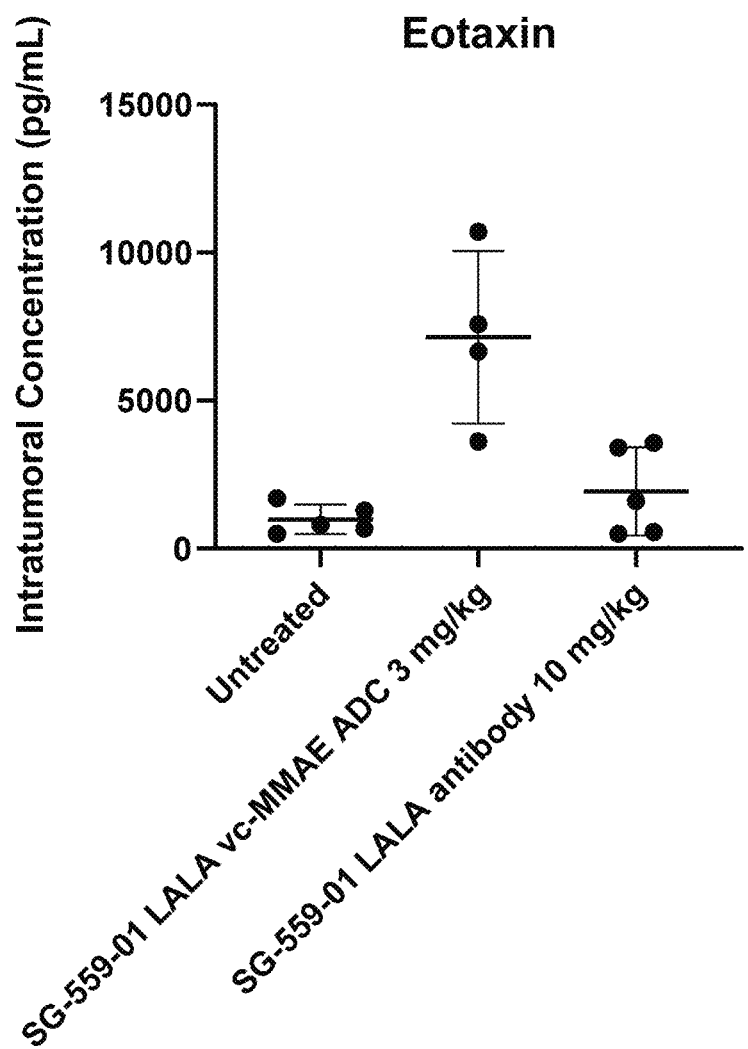
FIGS. 14A-14F show intratumoral inflammatory cytokine response in mice with Karpas 299 tumors treated by SG-559-01 LALA vc-MMAE ADC.
Figure 14B:
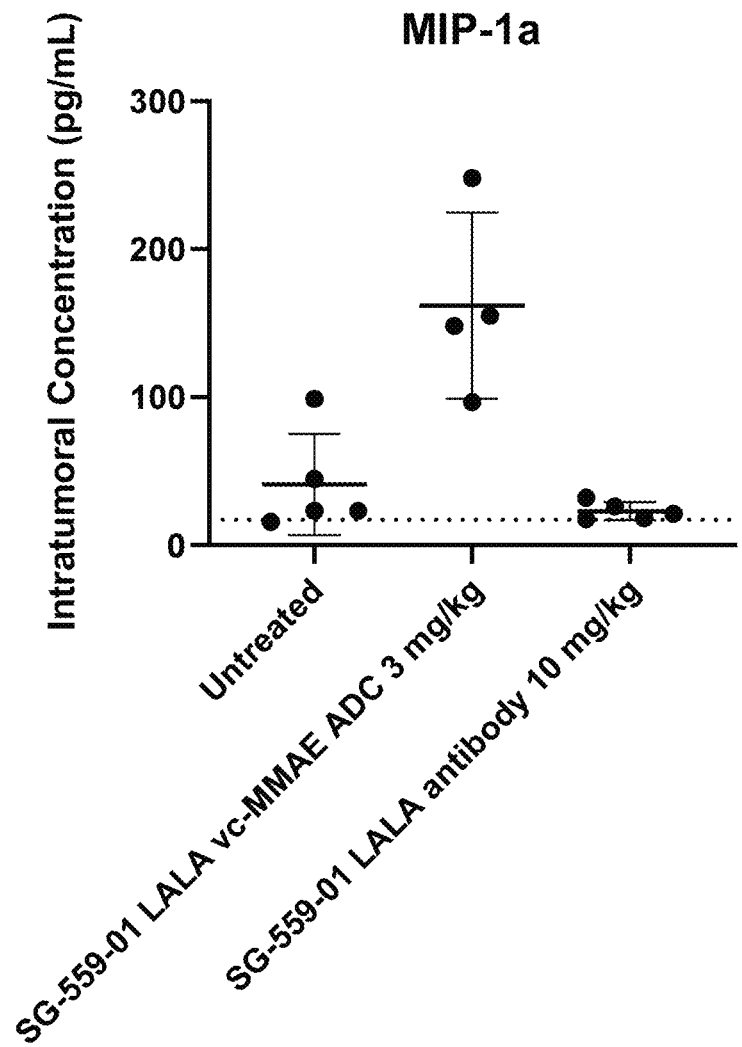
Figure 14C:
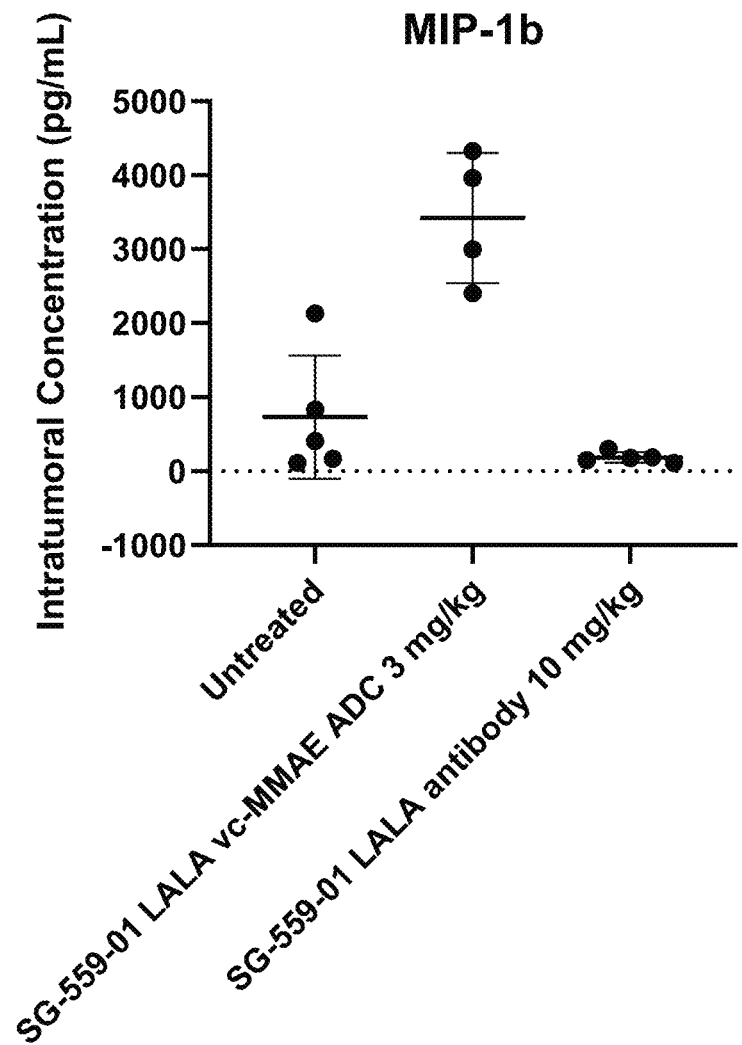
Figure 14D:
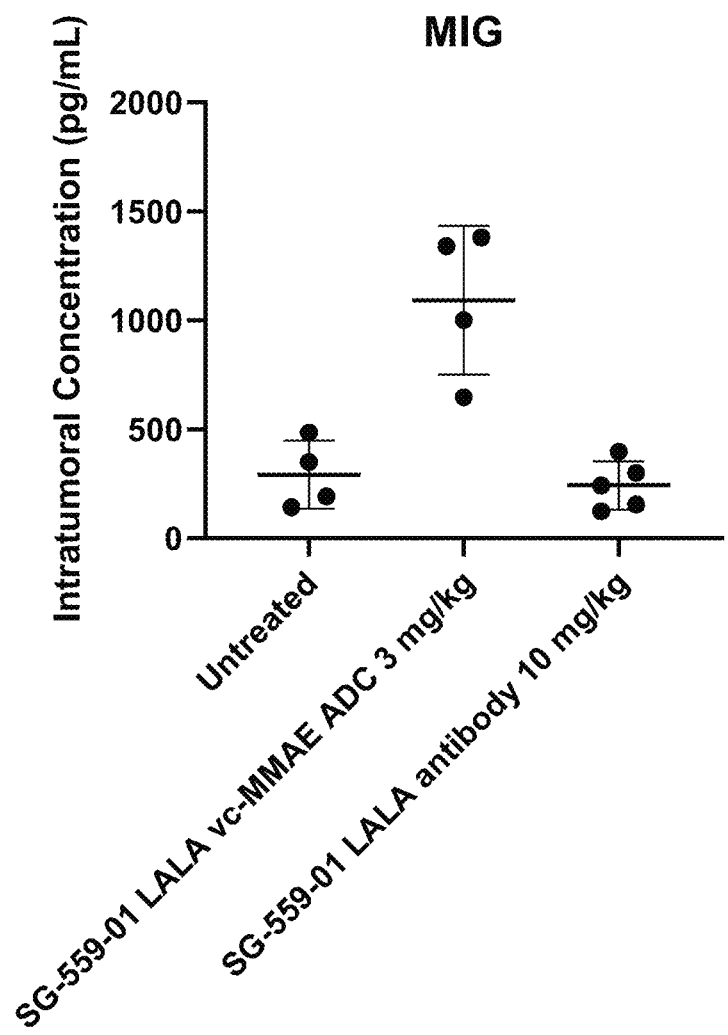
Figure 14E:
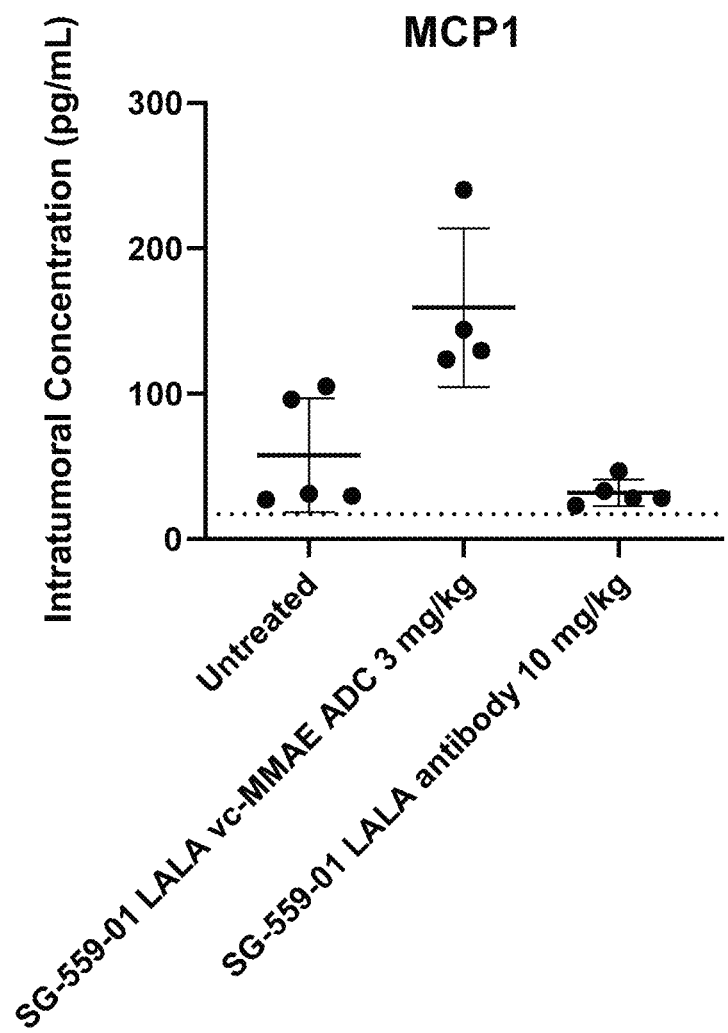
Figure 14F:
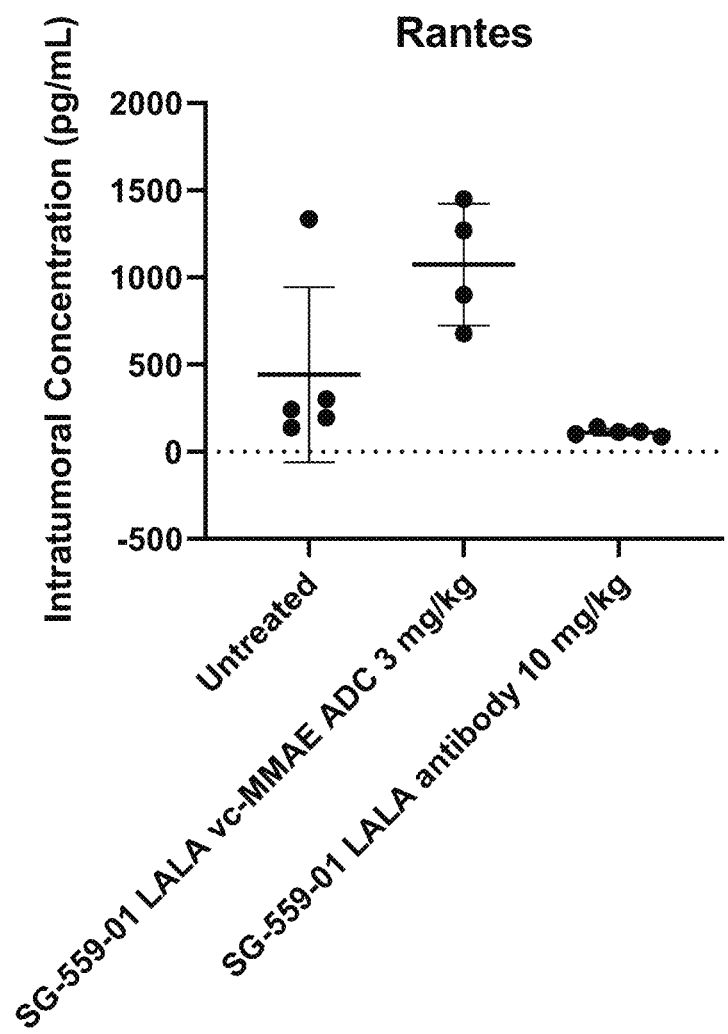

SG-559-01 LALA vc-MMAE ADC was further characterized for its ability to induce production of inflammatory cytokines in the tumor microenvironment (TME). Relative to both the untreated control and a SG-559-01 LALA antibody, SG-559-01 LALA vc-MMAE ADC induces inflammatory cytokines in the TME as measured by intratumoral concentrations of Eotaxin (chemokine for eosinophils; FIG. 14A), MIP1a (proinflammatory macrophage cytokine; FIG. 14B), MIP1b (proinflammatory macrophage cytokine; FIG. 14C), MIG/CXCL9 (induced by IFNγ, influences migration, and differentiation of immune cells; FIG. 14D), MCP1 (chemokine for monocytes/macrophages; FIG. 14E), and Rantes (chemokine for monocytes, T cells, and eosinophils; FIG. 14F).

Example 10: Binding Affinity to Glycosylated PD-L1 and Deglycosylated PD-L1

SG-559-01 was assessed for binding affinity to glycosylated and deglycosylated forms of PD-L1. Binding affinity was assessed using biolayer interferometry on the Octet Red 384 system (ForteBio) as described in the methods. PNGase F enzyme and a denaturation protocol were used to deglycosylate PD-L1 as described in the methods. SG-559-01 was assessed for binding affinity to deglycosylated PD-L1 and a control glycosylated PD-L1 (same treatment conditions but no PNGase F treatment, as described in the methods). A ~2-fold difference was seen in SG-559-01 binding affinity to deglycosylated PD-L1 compared to glycosylated PD-L1 (Table 5). Mass spectrometry was used to verify the glycosylation status of PD-L1.

TABLE 5

SG-559-01 Binding to Glycosylated versus Deglycosylated hPD-L1

| | Monovalent binding | | |
|---|---|---|---|
| Species | $K_D$ (nM) | $k_{on}$ ($M^{-1}s^{-1}$) | $k_{dis}$ ($s^{-1}$) |
| Control hPD-L1 | 7 | $1.1 \times 10^5$ | $1.7 \times 10^{-3}$ |
| Degly hPD-L1 | 15 | $3.9 \times 10^5$ | $2.7 \times 10^{-3}$ |

```
INFORMAL SEQUENCE LISTING
Ab1 heavy chain variable region - protein
                                                             SEQ ID NO: 1
QVQLVQSGAEVKKPGSSVKVSCKTSGDTFSTYAISWVRQAPGQGLEWMGGIIPIFGKAHYAQKFQGRVTITADESTS

TAYMELSSLRSEDTAVYFCARKFHFVSGSPFGMDVWGQGTTVTVSS

Ab1 light chain variable region - protein
                                                             SEQ ID NO: 2
EIVLTQSPATLSLSPGERATLSCRASQSVSSYLAWYQQKPGQAPRLLIYDASNRATGIPARFSGSGSGTDFTLTISS

LEPEDFAVYYCQQRSNWPTFGQGTKVEIK

Ab1 heavy chain CDR1 - protein
                                                             SEQ ID NO: 3
TYAIS Ab1 heavy chain CDR2 - protein
                                                             SEQ ID NO: 4
GIIPIFGKAHYAQKFQG Ab1 heavy chain CDR3 - protein
                                                             SEQ ID NO: 5
KFHFVSGSPFGMDV Ab1 light chain CDR1 - protein
                                                             SEQ ID NO: 6
RASQSVSSYLA Ab1 light chain CDR2 - protein
```

-continued

SEQ ID NO: 7
DASNRAT

Ab1 light chain CDR3 - protein
SEQ ID NO: 8
QQRSNWPT

SG-559-01 LALA hIgG1 heavy chain - protein
SEQ ID NO: 9
QVQLVQSGAEVKKPGSSVKVSCKTSGDTFSTAAISWVRQAPGQGLEWMGGIIPIFGKAHYAQKFQGRVTITADESTS

TAYMELSSLRSEDTAVYFCARKFHFVSGSPFGMDVWGQGTTVTVSSASTKGPSVFPLAPSSKSTSGGTAALGCLVKD

YFPEPVTVSWNSGALTSGVHTFPAVLQSSGLYSLSSVVTVPSSSLGTQTYICNVNHKPSNTKVDKKVEPKSCDKTHT

CPPCPAPEAAGGPSVFLFPPKPKDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMHEALHNHYTQKSLSLSPGK

SG-559-01 kappa light chain - protein
SEQ ID NO: 10
EIVLTQSPATLSLSPGERATLSCRASQSVSSYLAWYQQKPGQAPRLLIYDASNRATGIPARFSGSGSGTDFTLTISS

LEPEDFAVYYCQQRSNWPTFGQGTKVEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

SG-559-01 heavy chain variable region - protein
SEQ ID NO: 11
QVQLVQSGAEVKKPGSSVKVSCKTSGDTFSTAAISWVRQAPGQGLEWMGGIIPIFGKAHYAQKFQGRVTITADESTS

TAYMELSSLRSEDTAVYFCARKFHFVSGSPFGMDVWGQGTTVTVSS

SG-559-01 light chain variable region - protein
SEQ ID NO: 12
EIVLTQSPATLSLSPGERATLSCRASQSVSSYLAWYQQKPGQAPRLLIYDASNRATGIPARFSGSGSGTDFTLTISS

LEPEDFAVYYCQQRSNWPTFGQGTKVEIK

SG-559-01 heavy chain CDR1 - protein
SEQ ID NO: 13
TAAIS

SG-559-01 heavy chain CDR2 - protein
SEQ ID NO: 14
GIIPIFGKAHYAQKFQG

SG-559-01 heavy chain CDR3 - protein
SEQ ID NO: 15
KFHFVSGSPFGMDV

SG-559-01 light chain CDR1 - protein
SEQ ID NO: 16
RASQSVSSYLA

SG-559-01 light chain CDR2 - protein
SEQ ID NO: 17
DASNRAT

SG-559-01 light chain CDR3 - protein
SEQ ID NO: 18
QQRSNWPT

SG-559-02 LALA hIgG1 heavy chain - protein
SEQ ID NO: 19
QVQLVQSGAEVKKPGSSVKVSCKTSGDTFSTYAISWVRQAPGQGLEWMGGIIPIFGKAHYAQKFQGRVTITADESTS

TAYMELSSLRSEDTAVYFCARKFHFVSGSPFGMDVWGQGTTVTVSSASTKGPSVFPLAPSSKSTSGGTAALGCLVKD

YFPEPVTVSWNSGALTSGVHTFPAVLQSSGLYSLSSVVTVPSSSLGTQTYICNVNHKPSNTKVDKKVEPKSCDKTHT

CPPCPAPEAAGGPSVFLFPPKPKDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMHEALHNHYTQKSLSLSPGK

SG-559-02 kappa light chain - protein

-continued

EIVLTQSPATLSLSPGERATLSCRASQSVSSALAWYQQKPGQAPRLLIYDASNRATGIPARFSGSGSGTDFTLTISS
LEPEDFAVYYCQQRSNWPTFGQGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC
SEQ ID NO: 20

SG-559-02 heavy chain variable region - protein
SEQ ID NO: 21
QVQLVQSGAEVKKPGSSVKVSCKTSGDTFSTYAISWVRQAPGQGLEWMGGIIPIFGKAHYAQKFQGRVTITADESTS
TAYMELSSLRSEDTAVYFCARKFHFVSGSPFGMDVWGQGTTVTVSS SG-559-02 light chain variable region - protein
SEQ ID NO: 22
EIVLTQSPATLSLSPGERATLSCRASQSVSSALAWYQQKPGQAPRLLIYDASNRATGIPARFSGSGSGTDFTLTISS
LEPEDFAVYYCQQRSNWPTFGQGTKVEIK SG-559-02 heavy chain CDR1 - protein
SEQ ID NO: 23
TYAIS SG-559-02 heavy chain CDR2 - protein
SEQ ID NO: 24
GIIPIFGKAHYAQKFQG SG-559-02 heavy chain CDR3 - protein
SEQ ID NO: 25
KFHFVSGSPFGMDV SG-559-02 light chain CDR1 - protein
SEQ ID NO: 26
RASQSVSSALA SG-559-02 light chain CDR2 - protein
SEQ ID NO: 27
DASNRAT SG-559-02 light chain CDR3 - protein
SEQ ID NO: 28
QQRSNWPT SG-559-03 LALA hIgG1 heavy chain - protein
SEQ ID NO: 29
QVQLVQSGAEVKKPGSSVKVSCKTSGDTFSTYAISWVRQAPGQGLEWMGGIIPIFGKAHYAQKFQGRVTITADESTS
TAYMELSSLRSEDTAVYFCARKFHFVSGSPFGMDVWGQGTTVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHT
CPPCPAPEAAGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHEALHNHYTQKSLSLSPGK SG-559-03 kappa light chain - protein
SEQ ID NO: 30
EIVLTQSPATLSLSPGERATLSCRASQSVSSYLAWYQQKPGQAPRLLIYDASNRATGIPARFSGSGSGTDFTLTISS
LEPEDFAVYYCQQRSNLPTFGQGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC SG-559-03 heavy chain variable region - protein
SEQ ID NO: 31
QVQLVQSGAEVKKPGSSVKVSCKTSGDTFSTYAISWVRQAPGQGLEWMGGIIPIFGKAHYAQKFQGRVTITADESTS
TAYMELSSLRSEDTAVYFCARKFHFVSGSPFGMDVWGQGTTVTVSS SG-559-03 light chain variable region - protein
SEQ ID NO: 32
EIVLTQSPATLSLSPGERATLSCRASQSVSSYLAWYQQKPGQAPRLLIYDASNRATGIPARFSGSGSGTDFTLTISS
LEPEDFAVYYCQQRSNLPTFGQGTKVEIK SG-559-03 heavy chain CDR1 - protein
SEQ ID NO: 33
TYAIS SG-559-03 heavy chain CDR2 - protein
SEQ ID NO: 34
GIIPIFGKAHYAQKFQG SG-559-03 heavy chain CDR3 - protein
SEQ ID NO: 35
KFHFVSGSPFGMDV SG-559-03 light chain CDR1 - protein
SEQ ID NO: 36
RASQSVSSYLA SG-559-03 light chain CDR2 - protein
SEQ ID NO: 37
DASNRAT SG-559-03 light chain CDR3 - protein
SEQ ID NO: 38
QQRSNLPT SG-559-04 LALA hIgG1 heavy chain - protein
SEQ ID NO: 39
QVQLVQSGAEVKKPGSSVKVSCKTSGDTFSTYAISWVRQAPGQGLEWMGGIIPIFGKAHYAQKFQGRVTITADESTS
TAYMELSSLRSEDTAVYFCARKFHFVSGSGFGMDVWGQGTTVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHT
CPPCPAPEAAGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHEALHNHYTQKSLSLSPGK SG-559-04 kappa light chain - protein
SEQ ID NO: 40
EIVLTQSPATLSLSPGERATLSCRASQSVSSYLAWYQQKPGQAPRLLIYDASNRATGIPARFSGSGSGTDFTLTISS
LEPEDFAVYYCQQRSNWPTFGQGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC SG-559-04 heavy chain variable region - protein
SEQ ID NO: 41
QVQLVQSGAEVKKPGSSVKVSCKTSGDTFSTYAISWVRQAPGQGLEWMGGIIPIFGKAHYAQKFQGRVTITADESTS
TAYMELSSLRSEDTAVYFCARKFHFVSGSGFGMDVWGQGTTVTVSS SG-559-04 light chain variable region - protein
SEQ ID NO: 42
EIVLTQSPATLSLSPGERATLSCRASQSVSSYLAWYQQKPGQAPRLLIYDASNRATGIPARFSGSGSGTDFTLTISS
LEPEDFAVYYCQQRSNWPTFGQGTKVEIK SG-559-04 heavy chain CDR1 - protein
SEQ ID NO: 43
TYAIS SG-559-04 heavy chain CDR2 - protein
SEQ ID NO: 44
GIIPIFGKAHYAQKFQG SG-559-04 heavy chain CDR3 - protein
SEQ ID NO: 45
KFHFVSGSGFGMDV SG-559-04 light chain CDR1 - protein
SEQ ID NO: 46
RASQSVSSYLA SG-559-04 light chain CDR2 - protein
SEQ ID NO: 47
DASNRAT SG-559-04 light chain CDR3 - protein
SEQ ID NO: 48
QQRSNWPT SG-559-05 heavy chain CDR2 - protein -continued

```
GIIPIAGKAHYAQKFQG                                          SEQ ID NO: 49

SG-559-06 heavy chain CDR2 - protein
                                                           SEQ ID NO: 50
GIIPIFGAAHYAQKFQG SG-559-07 heavy chain CDR2 - protein
                                                           SEQ ID NO: 51
GIIPIFGRAHYAQKFQG SG-559-08 heavy chain CDR2 - protein
                                                           SEQ ID NO: 52
GIIPIFGKAAYAQKFQG SG-559-09 heavy chain CDR2 - protein
                                                           SEQ ID NO: 53
GIIPIFGKAFYAQKFQG SG-559-10 heavy chain CDR3 - protein
                                                           SEQ ID NO: 54
KFHFVSGAPFGMDV SG-559-11 heavy chain CDR3 - protein
                                                           SEQ ID NO: 55
KFHFVSGSPAGMDV SG-559-12 light chain CDR3 - protein
                                                           SEQ ID NO: 56
QQASNWPT SG-559-13 light chain CDR3 - protein
                                                           SEQ ID NO: 57
QQKSNWPT SG-559-14 light chain CDR3 - protein
                                                           SEQ ID NO: 58
QQRSAWPT SG-559-15 light chain CDR3 - protein
                                                           SEQ ID NO: 59
QQRSQWPT SG-559-16 light chain CDR3 - protein
                                                           SEQ ID NO: 60
QQRSNAPT SG-559-17 light chain CDR3 - protein
                                                           SEQ ID NO: 61
QQRSNFPT SG-559-01 hIgG1 heavy chain - protein
                                                           SEQ ID NO: 62
QVQLVQSGAEVKKPGSSVKVSCKTSGDTFSTAAISWVRQAPGQGLEWMGGIIPIFGKAHYAQKFQGRVTITADESTS
TAYMELSSLRSEDTAVYFCARKFHFVSGSPFGMDVWGQGTTVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHEALHNHYTQKSLSLSPGK SG-559-02 hIgG1 heavy chain - protein
                                                           SEQ ID NO: 63
QVQLVQSGAEVKKPGSSVKVSCKTSGDTFSTYAISWVRQAPGQGLEWMGGIIPIFGKAHYAQKFQGRVTITADESTS
TAYMELSSLRSEDTAVYFCARKFHFVSGSPFGMDVWGQGTTVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHEALHNHYTQKSLSLSPGK
```

SG-559-03 hIgG1 heavy chain - protein

SEQ ID NO: 64

QVQLVQSGAEVKKPGSSVKVSCKTSGDTFSTYAISWVRQAPGQGLEWMGGIIPIFGKAHYAQKFQGRVTITADESTS
TAYMELSSLRSEDTAVYFCARKFHFVSGSPFGMDVWGQGTTVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHEALHNHYTQKSLSLSPGK

SG-559-04 hIgG1 heavy chain - protein

SEQ ID NO: 65

QVQLVQSGAEVKKPGSSVKVSCKTSGDTFSTYAISWVRQAPGQGLEWMGGIIPIFGKAHYAQKFQGRVTITADESTS
TAYMELSSLRSEDTAVYFCARKFHFVSGSGEGMDVWGQGTTVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHEALHNHYTQKSLSLSPGK

SG-559-01 variable heavy region - nucleic acid

SEQ ID NO: 66 caggtccagctggtgcagtctggggctgaggtgaagaagcctgggtcctcggtgaaggtctcctgcaagacttctgg
agacaccttcagcaccgccgctatcagctgggtgcgacaggcccctggacaagggcttgagtggatgggagggatca
tccctatatttggtaaagcacactacgcacagaagttccagggcagagtcacgattaccgcggacgaatccacgagc
acagcctacatggagctgagcagcctgagatctgaggacacggccgtgtattttgtgcgagaaagtttcactttgt
ttcggggagccccttcggtatggacgtctggggccaagggaccacggtcaccgtctcctca SG-559-01 variable light region - nucleic acid

SEQ ID NO: 67 gaaattgtgttgacacagtctccagccacccctgtctttgtctccaggggaaagagccaccctctcctgcagggccag
tcagagtgttagcagctacttagcctggtaccaacagaaacctggccaggctcccaggctcctcatctatgatgcat
ccaacagggccactggcatcccagccaggttcagtggcagtgggtctgggacagacttcactctcaccatcagcagc
ctagagcctgaagattttgcagtttattactgtcagcagcgtagcaactggccgacgttcggccaagggaccaaggt
ggaaatcaaa SG-559-02 variable heavy region - nucleic acid

SEQ ID NO: 68 caggtccagctggtgcagtctggggctgaggtgaagaagcctgggtcctcggtgaaggtctcctgcaagacttctgg
agacaccttcagcacctatgctatcagctgggtgcgacaggcccctggacaagggcttgagtggatgggagggatca
tccctatatttggtaaagcacactacgcacagaagttccagggcagagtcacgattaccgcggacgaatccacgagc
acagcctacatggagctgagcagcctgagatctgaggacacggccgtgtattttgtgcgagaaagtttcactttgt
ttcggggagccccttcggtatggacgtctggggccaagggaccacggtcaccgtctcctca SG-559-02 variable light region - nucleic acid

SEQ ID NO: 69 gaaattgtgttgacacagtctccagccacccctgtctttgtctccaggggaaagagccaccctctcctgcagggccag
tcagagtgttagcagcgccttagcctggtaccaacagaaacctggccaggctcccaggctcctcatctatgatgcat
ccaacagggccactggcatcccagccaggttcagtggcagtgggtctgggacagacttcactctcaccatcagcagc
ctagagcctgaagattttgcagtttattactgtcagcagcgtagcaactggccgacgttcggccaagggaccaaggt
ggaaatcaaa SG-559-03 variable heavy region - nucleic acid

SEQ ID NO: 70 caggtccagctggtgcagtctggggctgaggtgaagaagcctgggtcctcggtgaaggtctcctgcaagacttctgg

-continued agacaccttcagcacctatgctatcagctgggtgcgacaggcccctggacaagggcttgagtggatgggagggatca tccctatatttggtaaagcacactacgcacagaagttccagggcagagtcacgattaccgcggacgaatccacgagc acagcctacatggagctgagcagcctgagatctgaggacacggccgtgtattttgtgcgagaaagtttcactttgt ttcggggagccccttcggtatggacgtctggggccaagggaccacggtcaccgtctcctca SG-559-03 variable light region - nucleic acid

SEQ ID NO: 71 gaaattgtgttgacacagtctccagccaccctgtctttgtctccaggggaaagagccaccctctcctgcagggccag tcagagtgttagcagctacttagcctggtaccaacagaaacctggccaggctcccaggctcctcatctatgatgcat ccaacagggccactggcatcccagccaggttcagtggcagtgggtctgggacagacttcactctcaccatcagcagc ctagagcctgaagattttgcagtttattactgtcagcagcgtagcaacctgccgacgttcggccaagggaccaaggt ggaaatcaaa SG-559-04 variable heavy region - nucleic acid

SEQ ID NO: 72 caggtccagctggtgcagtctggggctgaggtgaagaagcctgggtcctcggtgaaggtctcctgcaagacttctgg agacaccttcagcacctatgctatcagctgggtgcgacaggcccctggacaagggcttgagtggatgggagggatca tccctatatttggtaaagcacactacgcacagaagttccagggcagagtcacgattaccgcggacgaatccacgagc acagcctacatggagctgagcagcctgagatctgaggacacggccgtgtattttgtgcgagaaagtttcactttgt ttcggggagcggcttcggtatggacgtctggggccaagggaccacggtcaccgtctcctca SG-559-04 variable light region - nucleic acid

SEQ ID NO: 73 gaaattgtgttgacacagtctccagccaccctgtctttgtctccaggggaaagagccaccctctcctgcagggccag tcagagtgttagcagctacttagcctggtaccaacagaaacctggccaggctcccaggctcctcatctatgatgcat ccaacagggccactggcatcccagccaggttcagtggcagtgggtctgggacagacttcactctcaccatcagcagc ctagagcctgaagattttgcagtttattactgtcagcagcgtagcaactggccgacgttcggccaagggaccaaggt ggaaatcaaa SG-559-01 LALA hIgG1 heavy chain - nucleic acid

SEQ ID NO: 74 caggtccagctggtgcagtctggggctgaggtgaagaagcctgggtcctcggtgaaggtctcctgcaagacttctgg agacaccttcagcaccgccgctatcagctgggtgcgacaggcccctggacaagggcttgagtggatgggagggatca tccctatatttggtaaagcacactacgcacagaagttccagggcagagtcacgattaccgcggacgaatccacgagc acagcctacatggagctgagcagcctgagatctgaggacacggccgtgtattttgtgcgagaaagtttcactttgt ttcggggagccccttcggtatggacgtctggggccaagggaccacggtcaccgtctcctcagctagcaccaagggcc catctgtcttccccctggcaccctcctccaagagcacctctgggggcacagctgccctgggctgcctggtcaaggac tacttccctgaacctgtgacagtgtcctggaactcaggagccctgaccagcggcgtgcacaccttcccggctgtcct acagtcctcaggactctactccctcagcagcgtggtgaccgtgccctccagcagcttgggcacccagacctacatct gcaacgtgaatcacaagcccagcaacaccaaggtggacaagaaagttgagcccaaatcttgtgacaaaactcacaca tgcccaccgtgcccagcacctgaagctgctggggaccgtcagtcttcctcttccccccaaaacccaaggacaccct catgatctcccggacccctgaggtcacatgcgtggtggtggacgtgagccacgaagaccctgaggtcaagttcaact ggtacgtggacggcgtggaggtgcataatgccaagacaaagccgcgggaggagcagtacaacagcacgtaccgtgtg gtcagcgtcctcaccgtcctgcaccaggactggctgaatggcaaggagtacaagtgcaaggtctccaacaaagccct cccagcccccatcgagaaaaccatctccaaagccaaagggcagccccgagaaccacaggtttacaccctgcccccat cccgggatgagctgaccaagaaccaggtcagcctgacctgcctggtcaaaggcttctatcccagcgacatcgccgtg gagtgggagagcaatgggcagccggagaacaactacaagaccacgcctcccgtgctggactccgacggctccttctt cctctacagcaagctcaccgtggacaagagcaggtggcagcaggggaacgtcttctcatgctccgtgatgcatgagg ctctgcacaaccactacacacagaagagcctctccctgtctccgggcaaa SG-559-01 kappa light chain - nucleic acid

SEQ ID NO: 75 gaaattgtgttgacacagtctccagccaccctgtctttgtctccaggggaaagagccaccctctcctgcagggccag tcagagtgttagcagctacttagcctggtaccaacagaaacctggccaggctcccaggctcctcatctatgatgcat ccaacagggccactggcatcccagccaggttcagtggcagtgggtctgggacagacttcactctcaccatcagcagc ctagagcctgaagattttgcagtttattactgtcagcagcgtagcaactggccgacgttcggccaagggaccaaggt ggaaatcaaacgtacggtggctgcaccatctgtcttcatcttcccgccatctgatgagcagttgaaatctggaactg cctctgttgtgtgcctgctgaataacttctatcccagagaggccaaagtacagtggaaggtggataacgccctccaa tcgggtaactcccaggagagtgtcacagagcaggacagcaaggacagcacctacagcctcagcagcaccctgacgct gagcaaagcagactacgagaaacacaaagtctacgcctgcgaagtcacccatcagggcctgagctcgcccgtcacaa agagcttcaacaggggagagtgt SG-559-01 hIgG1 heavy chain - nucleic acid

SEQ ID NO: 76 caggtccagctggtgcagtctggggctgaggtgaagaagcctggggtcctcggtgaaggtctcctgcaagacttctgg agacaccttcagcaccgccgctatcagctgggtgcgacaggcccctggacaagggcttgagtggatgggagggatca tccctatatttggtaaagcacactacgcacagaagttccagggcagagtcacgattaccgcggacgaatccacgagc acagcctacatggagctgagcagcctgagatctgaggacacggccgtgtattttgtgcgagaaagtttcactttgt ttcggggagccccttcggtatggacgtctgggcaagggaccacggtcaccgtctcctcagctagcaccaagggcc catctgtcttccccctggcaccctcctccaagagcacctctgggggcacagctgccctgggctgcctggtcaaggac tacttccctgaacctgtgacagtgtcctggaactcaggagccctgaccagcggcgtgcacaccttcccggctgtcct acagtcctcaggactctactccctcagcagcgtggtgaccgtgccctccagcagcttgggcacccagacctacatct gcaacgtgaatcacaagcccagcaacaccaaggtggacaagaaagttgagcccaaatcttgtgacaaaactcacaca tgcccaccgtgcccagcacctgaactcctggggggaccgtcagtcttcctcttccccccaaaacccaaggacaccct catgatctcccggacccctgaggtcacatgcgtggtggtggacgtgagccacgaagaccctgaggtcaagttcaact ggtacgtggacggcgtggaggtgcataatgccaagacaaagccgcgggaggagcagtacaacagcacgtaccgtgtg gtcagcgtcctcaccgtcctgcaccaggactggctgaatggcaaggagtacaagtgcaaggtctccaacaaagccct cccagcccccatcgagaaaaccatctccaaagccaaagggcagccccgagaaccacaggtgtacaccctgcccccat cccgggatgagctgaccaagaaccaggtcagcctgacctgcctggtcaaaggcttctatcccagcgacatcgccgtg gagtgggagagcaatgggcagccggagaacaactacaagaccacgcctcccgtgctggactccgacggctccttctt cctctacagcaagctcaccgtggacaagagcaggtggcagcaggggaacgtcttctcatgctccgtgatgcatgagg ctctgcacaaccactacacacagaagagcctctccctgtctccgggcaaa SG-559-02 LALA hIgG1 heavy chain - nucleic acid

SEQ ID NO: 77 caggtccagctggtgcagtctggggctgaggtgaagaagcctggggtcctcggtgaaggtctcctgcaagacttctgg agacaccttcagcacctatgctatcagctgggtgcgacaggcccctggacaagggcttgagtggatgggagggatca tccctatatttggtaaagcacactacgcacagaagttccagggcagagtcacgattaccgcggacgaatccacgagc acagcctacatggagctgagcagcctgagatctgaggacacggccgtgtattttgtgcgagaaagtttcactttgt ttcggggagccccttcggtatggacgtctgggcaagggaccacggtcaccgtctcctcagctagcaccaagggcc catctgtcttccccctggcaccctcctccaagagcacctctgggggcacagctgccctgggctgcctggtcaaggac tacttccctgaacctgtgacagtgtcctggaactcaggagccctgaccagcggcgtgcacaccttcccggctgtcct acagtcctcaggactctactccctcagcagcgtggtgaccgtgccctccagcagcttgggcacccagacctacatct gcaacgtgaatcacaagcccagcaacaccaaggtggacaagaaagttgagcccaaatcttgtgacaaaactcacaca tgcccaccgtgcccagcacctgaagctgctggggggaccgtcagtcttcctcttccccccaaaacccaaggacaccct -continued

```
catgatctcccggacccctgaggtcacatgcgtggtggtggacgtgagccacgaagaccctgaggtcaagttcaact ggtacgtggacggcgtggaggtgcataatgccaagacaaagccgcgggaggagcagtacaacagcacgtaccgtgtg gtcagcgtcctcaccgtcctgcaccaggactggctgaatggcaaggagtacaagtgcaaggtctccaacaaagccct cccagcccccatcgagaaaaccatctccaaagccaaagggcagccccgagaaccacaggtttacaccctgcccccat cccgggatgagctgaccaagaaccaggtcagcctgacctgcctggtcaaaggcttctatcccagcgacatcgccgtg gagtgggagagcaatgggcagccggagaacaactacaagaccacgcctcccgtgctggactccgacggctccttctt cctctacagcaagctcaccgtggacaagagcaggtggcagcaggggaacgtcttctcatgctccgtgatgcatgagg ctctgcacaaccactacacacagaagagcctctccctgtctccgggcaaa
```

SG-559-02 kappa light chain - nucleic acid
SEQ ID NO: 78
```
gaaattgtgttgacacagtctccagccacccctgtctttgtctccaggggaaagagccaccctctcctgcagggccag tcagagtgttagcagcgccttagcctggtaccaacagaaacctggccaggctcccaggctcctcatctatgatgcat ccaacagggccactggcatcccagccaggttcagtggcagtgggtctgggacagacttcactctcaccatcagcagc ctagagcctgaagattttgcagtttattactgtcagcagcgtagcaactggccgacgttcggccaagggaccaaggt ggaaatcaaacgtacggtggctgcaccatctgtcttcatcttcccgccatctgatgagcagttgaaatctggaactg cctctgttgtgtgcctgctgaataacttctatcccagagaggccaaagtacagtggaaggtggataacgccctccaa tcgggtaactcccaggagagtgtcacagagcaggacagcaaggacagcacctacagcctcagcagcaccctgacgct gagcaaagcagactacgagaaacacaaagtctacgcctgcgaagtcacccatcagggcctgagctcgcccgtcacaa agagcttcaacaggggagagtgt
```

SG-559-02 hIgG1 heavy chain - nucleic acid
SEQ ID NO: 79
```
caggtccagctggtgcagtctggggctgaggtgaagaagcctgggtcctcggtgaaggtctcctgcaagacttctgg agacaccttcagcacctatgctatcagctgggtgcgacaggcccctggacaagggcttgagtggatgggagggatca tccctatatttggtaaagcacactacgcacagaagttccagggcagagtcacgattaccgcggacgaatccacgagc acagcctacatggagctgagcagcctgagatctgaggacacggccgtgtattttgtgcgagaaagtttcactttgt ttcggggagccccttcggtatggacgtctggggccaagggaccacggtcaccgtctcctcagctagcaccaagggcc catctgtcttccccctggcaccctcctccaagagcacctctgggggcacagctgccctgggctgcctggtcaaggac tacttccctgaacctgtgacagtgtcctggaactcaggagccctgaccagcggcgtgcacaccttcccggctgtcct acagtcctcaggactctactccctcagcagcgtggtgaccgtgccctccagcagcttgggcacccagacctacatct gcaacgtgaatcacaagcccagcaacaccaaggtggacaagaaagttgagcccaaatcttgtgacaaaactcacaca tgcccaccgtgcccagcacctgaactcctggggggaccgtcagtcttcctcttccccccaaaacccaaggacaccct catgatctcccggacccctgaggtcacatgcgtggtggtggacgtgagccacgaagaccctgaggtcaagttcaact ggtacgtggacggcgtggaggtgcataatgccaagacaaagccgcgggaggagcagtacaacagcacgtaccgtgtg gtcagcgtcctcaccgtcctgcaccaggactggctgaatggcaaggagtacaagtgcaaggtctccaacaaagccct cccagcccccatcgagaaaaccatctccaaagccaaagggcagccccgagaaccacaggtgtacaccctgcccccat cccgggatgagctgaccaagaaccaggtcagcctgacctgcctggtcaaaggcttctatcccagcgacatcgccgtg gagtgggagagcaatgggcagccggagaacaactacaagaccacgcctcccgtgctggactccgacggctccttctt cctctacagcaagctcaccgtggacaagagcaggtggcagcaggggaacgtcttctcatgctccgtgatgcatgagg ctctgcacaaccactacacacagaagagcctctccctgtctccgggcaaa
```

SG-559-03 LALA hIgG1 heavy chain - nucleic acid
SEQ ID NO: 80
```
caggtccagctggtgcagtctggggctgaggtgaagaagcctgggtcctcggtgaaggtctcctgcaagacttctgg agacaccttcagcacctatgctatcagctgggtgcgacaggcccctggacaagggcttgagtggatgggagggatca tccctatatttggtaaagcacactacgcacagaagttccagggcagagtcacgattaccgcggacgaatccacgagc
```

-continued acagcctacatggagctgagcagcctgagatctgaggacacggccgtgtattttgtgcgagaaagtttcactttgt ttcggggagccccttcggtatggacgtctggggccaagggaccacggtcaccgtctcctcagctagcaccaagggcc catctgtcttccccctggcaccctcctccaagagcacctctgggggcacagctgccctgggctgcctggtcaaggac tacttccctgaacctgtgacagtgtcctggaactcaggagccctgaccagcggcgtgcacaccttcccggctgtcct acagtcctcaggactctactccctcagcagcgtggtgaccgtgccctccagcagcttgggcacccagacctacatct gcaacgtgaatcacaagcccagcaacaccaaggtggacaagaaagttgagcccaaatcttgtgacaaaactcacaca tgcccaccgtgcccagcacctgaagctgctggggaccgtcagtcttcctcttccccccaaaacccaaggacaccct catgatctcccggacccctgaggtcacatgcgtggtggtggacgtgagccacgaagaccctgaggtcaagttcaact ggtacgtggacggcgtggaggtgcataatgccaagacaaagccgcgggaggagcagtacaacagcacgtaccgtgtg gtcagcgtcctcaccgtcctgcaccaggactggctgaatggcaaggagtacaagtgcaaggtctccaacaaagccct cccagcccccatcgagaaaaccatctccaaagccaaagggcagccccgagaaccacaggtttacaccctgcccccat cccgggatgagctgaccaagaaccaggtcagcctgacctgcctggtcaaaggcttctatcccagcgacatcgccgtg gagtgggagagcaatgggcagccggagaacaactacaagaccacgcctcccgtgctggactccgacggctccttctt cctctacagcaagctcaccgtggacaagagcaggtggcagcaggggaacgtcttctcatgctccgtgatgcatgagg ctctgcacaaccactacacacagaagagcctctccctgtctccgggcaaa SG-559-03 kappa light chain - nucleic acid

SEQ ID NO: 81 gaaattgtgttgacacagtctccagccaccctgtctttgtctccaggggaaagagccaccctctcctgcagggccag tcagagtgttagcagctacttagcctggtaccaacagaaacctggccaggctcccaggctcctcatctatgatgcat ccaacagggccactggcatcccagccaggttcagtggcagtgggtctgggacagacttcactctcaccatcagcagc ctagagcctgaagattttgcagtttattactgtcagcagcgtagcaacctgccgacgttcggccaagggaccaaggt ggaaatcaaacgtacggtggctgcaccatctgtcttcatcttcccgccatctgatgagcagttgaaatctggaactg cctctgttgtgtgcctgctgaataacttctatcccagagaggccaaagtacagtggaaggtggataacgccctccaa tcgggtaactcccaggagagtgtcacagagcaggacagcaaggacagcacctacagcctcagcagcaccctgacgct gagcaaagcagactacgagaaacacaaagtctacgcctgcgaagtcacccatcagggcctgagctcgcccgtcacaa agagcttcaacaggggagagtgt SG-559-03 hIgG1 heavy chain - nucleic acid

SEQ ID NO: 82 caggtccagctggtgcagtctggggctgaggtgaagaagcctgggtcctcggtgaaggtctcctgcaagacttctgg agacaccttcagcacctatgctatcagctgggtgcgacaggcccctggacaagggcttgagtggatgggagggatca tccctatatttggtaaagcacactacgcacagaagttccagggcagagtcacgattaccgcggacgaatccacgagc acagcctacatggagctgagcagcctgagatctgaggacacggccgtgtattttgtgcgagaaagtttcactttgt ttcggggagccccttcggtatggacgtctggggccaagggaccacggtcaccgtctcctcagctagcaccaagggcc catctgtcttccccctggcaccctcctccaagagcacctctgggggcacagctgccctgggctgcctggtcaaggac tacttccctgaacctgtgacagtgtcctggaactcaggagccctgaccagcggcgtgcacaccttcccggctgtcct acagtcctcaggactctactccctcagcagcgtggtgaccgtgccctccagcagcttgggcacccagacctacatct gcaacgtgaatcacaagcccagcaacaccaaggtggacaagaaagttgagcccaaatcttgtgacaaaactcacaca tgcccaccgtgcccagcacctgaactcctggggggaccgtcagtcttcctcttccccccaaaacccaaggacaccct catgatctcccggacccctgaggtcacatgcgtggtggtggacgtgagccacgaagaccctgaggtcaagttcaact ggtacgtggacggcgtggaggtgcataatgccaagacaaagccgcgggaggagcagtacaacagcacgtaccgtgtg gtcagcgtcctcaccgtcctgcaccaggactggctgaatggcaaggagtacaagtgcaaggtctccaacaaagccct cccagcccccatcgagaaaaccatctccaaagccaaagggcagccccgagaaccacaggtgtacaccctgcccccat -continued cccgggatgagctgaccaagaaccaggtcagcctgacctgcctggtcaaaggcttctatcccagcgacatcgccgtg gagtgggagagcaatgggcagccggagaacaactacaagaccacgcctcccgtgctggactccgacggctccttctt cctctacagcaagctcaccgtggacaagagcaggtggcagcaggggaacgtcttctcatgctccgtgatgcatgagg ctctgcacaaccactacacacagaagagcctctccctgtctccgggcaaa SG-559-04 LALA hIgG1 heavy chain - nucleic acid

SEQ ID NO: 83 caggtccagctggtgcagtctggggctgaggtgaagaagcctgggtcctcggtgaaggtctcctgcaagacttctgg agacaccttcagcacctatgctatcagctgggtgcgacaggcccctggacaagggcttgagtggatgggagggatca tccctatatttggtaaagcacactacgcacagaagttccagggcagagtcacgattaccgcggacgaatccacgagc acagcctacatggagctgagcagcctgagatctgaggacacggccgtgtattttgtgcgagaaagtttcactttgt ttcggggagcggcttcggtatggacgtctggggccaagggaccacggtcaccgtctcctcagctagcaccaagggcc catctgtcttccccctggcaccctcctccaagagcacctctgggggcacagctgccctgggctgcctggtcaaggac tacttccctgaacctgtgacagtgtcctggaactcaggagccctgaccagcggcgtgcacaccttcccggctgtcct acagtcctcaggactctactccctcagcagcgtggtgaccgtgccctccagcagcttgggcacccagacctacatct gcaacgtgaatcacaagcccagcaacaccaaggtggacaagaaagttgagcccaaatcttgtgacaaaactcacaca tgcccaccgtgcccagcacctgaagctgctggggaccgtcagtcttcctcttccccccaaaacccaaggacaccct catgatctcccggacccctgaggtcacatgcgtggtggtggacgtgagccacgaagaccctgaggtcaagttcaact ggtacgtggacggcgtggaggtgcataatgccaagacaaagccgcgggaggagcagtacaacagcacgtaccgtgtg gtcagcgtcctcaccgtcctgcaccaggactggctgaatggcaaggagtacaagtgcaaggtctccaacaaagccct cccagcccccatcgagaaaaccatctccaaagccaaagggcagccccgagaaccacaggtttacaccctgccccat cccgggatgagctgaccaagaaccaggtcagcctgacctgcctggtcaaaggcttctatcccagcgacatcgccgtg gagtgggagagcaatgggcagccggagaacaactacaagaccacgcctcccgtgctggactccgacggctccttctt cctctacagcaagctcaccgtggacaagagcaggtggcagcaggggaacgtcttctcatgctccgtgatgcatgagg ctctgcacaaccactacacacagaagagcctctccctgtctccgggcaaa SG-559-04 kappa light chain - nucleic acid

SEQ ID NO: 84 gaaattgtgttgacacagtctccagccaccctgtctttgtctccaggggaaagagccaccctctcctgcagggccag tcagagtgttagcagctacttagcctggtaccaacagaaacctggccaggctcccaggctcctcatctatgatgcat ccaacagggccactggcatcccagccaggttcagtggcagtgggtctgggacagacttcactctcaccatcagcagc ctagagcctgaagattttgcagtttattactgtcagcagcgtagcaactggccgacgttcggccaagggaccaaggt ggaaatcaaacgtacggtggctgcaccatctgtcttcatcttcccgccatctgatgagcagttgaaatctggaactg cctctgttgtgtgcctgctgaataacttctatcccagagaggccaaagtacagtggaaggtggataacgccctccaa tcgggtaactcccaggagagtgtcacagagcaggacagcaaggacagcacctacagcctcagcagcaccctgacgct gagcaaagcagactacgagaaacacaaagtctacgcctgcgaagtcacccatcagggcctgagctcgcccgtcacaa agagcttcaacaggggagagtgt SG-559-04 hIgG1 heavy chain - nucleic acid

SEQ ID NO: 85 caggtccagctggtgcagtctggggctgaggtgaagaagcctgggtcctcggtgaaggtctcctgcaagacttctgg agacaccttcagcacctatgctatcagctgggtgcgacaggcccctggacaagggcttgagtggatgggagggatca tccctatatttggtaaagcacactacgcacagaagttccagggcagagtcacgattaccgcggacgaatccacgagc acagcctacatggagctgagcagcctgagatctgaggacacggccgtgtattttgtgcgagaaagtttcactttgt ttcggggagcggcttcggtatggacgtctggggccaagggaccacggtcaccgtctcctcagctagcaccaagggcc catctgtcttccccctggcaccctcctccaagagcacctctgggggcacagctgccctgggctgcctggtcaaggac tacttccctgaacctgtgacagtgtcctggaactcaggagccctgaccagcggcgtgcacaccttcccggctgtcct -continued

```
acagtcctcaggactctactccctcagcagcgtggtgaccgtgcccccagcagcttgggcacccagacctacatct
gcaacgtgaatcacaagcccagcaacaccaaggtggacaagaaagttgagcccaaatcttgtgacaaaactcacaca
tgcccaccgtgcccagcacctgaactcctggggggaccgtcagtcttcctcttccccccaaaacccaaggacaccct
catgatctcccggacccctgaggtcacatgcgtggtggtggacgtgagccacgaagaccctgaggtcaagttcaact
ggtacgtggacggcgtggaggtgcataatgccaagacaaagccgcgggaggagcagtacaacagcacgtaccgtgtg
gtcagcgtcctcaccgtcctgcaccaggactggctgaatggcaaggagtacaagtgcaaggtctccaacaaagccct
cccagcccccatcgagaaaaccatctccaaagccaaagggcagccccgagaaccacaggtgtacaccctgcccccat
cccgggatgagctgaccaagaaccaggtcagcctgacctgcctggtcaaaggcttctatcccagcgacatcgccgtg
gagtgggagagcaatgggcagccggagaacaactacaagaccacgcctcccgtgctggactccgacggctccttctt
cctctacagcaagctcaccgtggacaagagcaggtggcagcaggggaacgtcttctcatgctccgtgatgcatgagg
ctctgcacaaccactacacacagaagagcctctccctgtctccgggcaaa
```

Ab1 hIgG1 heavy chain - protein
SEQ ID NO: 86

QVQLVQSGAEVKKPGSSVKVSCKTSGDTFSTYAISWVRQAPGQGLEWMGGIIPIFGKAHYAQKFQGRVTITADESTS

TAYMELSSLRSEDTAVYFCARKFHFVSGSPFGMDVWGQGTTVTVSSASTKGPSVFPLAPSSKSTSGGTAALGCLVKD

YFPEPVTVSWNSGALTSGVHTFPAVLQSSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMHEALHNHYTQKSLSLSPGK

Ab1 kappa light chain - protein
SEQ ID NO: 87

EIVLTQSPATLSLSPGERATLSCRASQSVSSYLAWYQQKPGQAPRLLIYDASNRATGIPARFSGSGSGTDFTLTISS

LEPEDFAVYYCQQRSNWPTFGQGTKVEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

The invention claimed is:

1. An antibody or antigen-binding fragment thereof that specifically binds to the human PD-L1 protein, wherein the antibody comprises the heavy chain CDR sequences of SEQ ID NOs: 13-15 and the light chain CDR sequences of SEQ ID NOs: 16-18.

2. The antibody of claim 1, wherein the antibody further exhibits a total internalization that is higher than the total internalization of an antibody comprising the heavy chain variable region sequence of SEQ ID NO: 1 and the light chain variable region sequence of SEQ ID NO: 2.

3. The antibody of claim 1, wherein the antibody further exhibits an IC50 that is higher than the IC50 of an antibody comprising the heavy chain variable region sequence of SEQ ID NO: 1 and the light chain variable region sequence of SEQ ID NO: 2.

4. The antibody of claim 3, wherein the antibody is conjugated to monomethyl auristatin E (MMAE), and wherein the IC50 is between 3 ng/mL and 20 ng/mL in an MDA-MB-231 cell line.

5. The antibody of claim 3, wherein the antibody is conjugated to camptothecin, and wherein the IC50 is between 15 ng/mL and 55 ng/mL in an MDA-MB-231 cell line.

6. The antibody of claim 1, wherein the antibody comprises the heavy chain variable region sequence of SEQ ID NO: 11 and the light chain variable region sequence of SEQ ID NO: 12.

7. The antibody of claim 1, wherein the antibody comprises the heavy chain sequence of SEQ ID NO: 9 and the light chain sequence of SEQ ID NO: 10.

8. The antibody of claim 1, wherein the fragment is a Fab, Fab', F(ab')$_2$, Fab'-SH, Fv, diabody, linear antibody, or single-chain antibody fragment.

9. The antibody of claim 1, wherein the antibody contains L234A and L235A mutations in the heavy chain of the antibody.

10. The antibody of claim 1, wherein the heavy chain constant region is of the IgG1 isotype.

11. The antibody of claim 1, wherein the antibody is a humanized or chimeric antibody.

12. The antibody of claim 1, wherein the antibody is conjugated to a cytotoxic agent via a linker.

13. The antibody of claim 12, wherein the antibody is conjugated to monomethyl auristatin E (MMAE).

14. The antibody of claim 13, wherein the antibody is conjugated to MMAE via an enzyme-cleavable linker unit.

15. The antibody of claim 14, wherein the enzyme-cleavable linker unit comprises a Val-Cit linker.

16. The antibody of claim 12, wherein the antibody is conjugated to MMAE via a linker forming an antibody-drug conjugate having the structure:

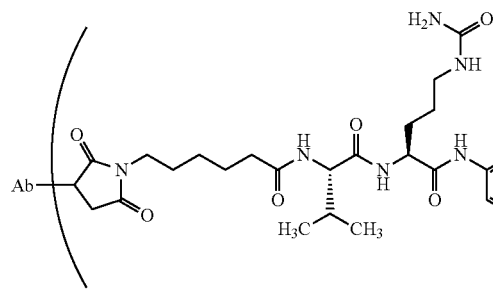
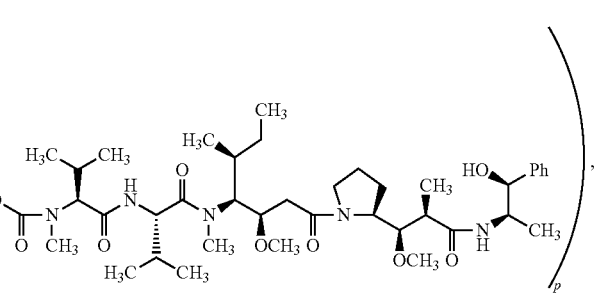

wherein Ab represents the antibody and p ranges from 2 to 10.

17. The antibody of claim 16, wherein p is 4.

18. The antibody of claim 16, wherein p is 8.

19. The antibody of claim 12, wherein the antibody is conjugated to camptothecin.

20. The antibody of claim 19, wherein the antibody is conjugated to camptothecin via an enzyme-cleavable linker unit.

21. The antibody of claim 20, wherein the enzyme-cleavable linker unit comprises a Val-Lys-Gly linker.

22. The antibody of claim 19, wherein the antibody is conjugated to camptothecin via a linker forming an antibody-drug conjugate having the structure:

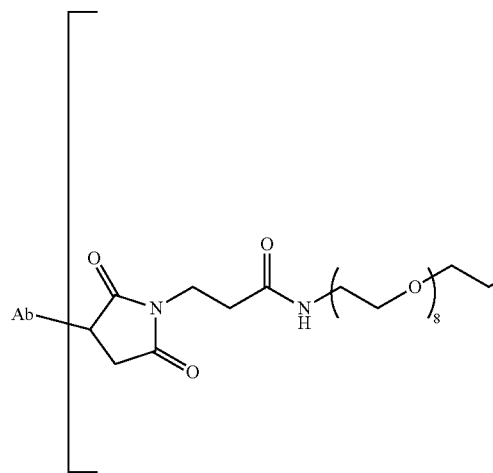

wherein Ab represents the antibody and p ranges from 2 to 10.

23. The antibody of claim 22, wherein p is 4.

24. The antibody of claim 22, wherein p is 8.

25. A pharmaceutical composition that comprises a therapeutically effective amount of the antibody of claim 1 and a pharmaceutically acceptable excipient.

26. A method of treating cancer in a subject, comprising administering to the subject the antibody of claim 1.

27. The method of claim 26, wherein the subject is a human subject.

28. The method of claim 26 or 27, wherein the cancer is melanoma, non-small cell lung cancer (NSCLC), small cell lung cancer (SCLC), head and neck cancer, triple negative breast cancer (TNBC), ovarian cancer, urothelial cancer, hepatocellular carcinoma (HCC), gastric cancer, or cervical cancer.

29. A nucleic acid encoding the antibody as defined by claim 1.

30. A vector comprising the nucleic acid of claim 29.

31. A host cell comprising the nucleic acid of claim 29.

32. The host cell of claim 31, wherein the host cell is a Chinese hamster ovary (CHO) cell.

33. A method of producing an antibody or antigen-binding fragment thereof that specifically binds to the human PD-L1 protein, comprising culturing the host cell of claim 31 or 32 under a condition suitable for production of the antibody.

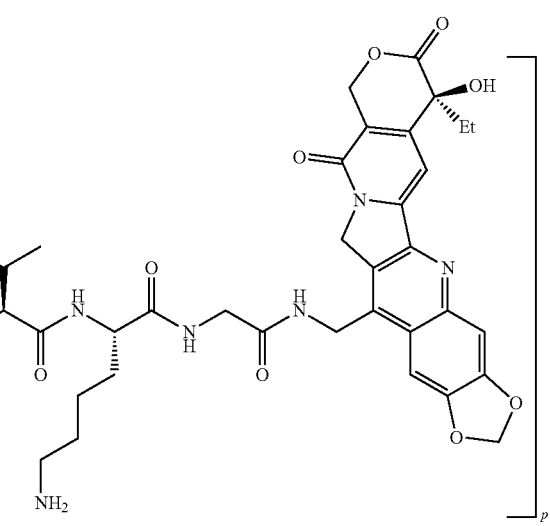

34. A method of producing an antibody drug-conjugate that specifically binds to the human PD-L1 protein, comprising culturing the host cell of claim 31 or 32 under a condition suitable for production of the antibody; and conjugating the antibody to a cytotoxic agent.

35. The method of claim 34, wherein the cytotoxic agent is MMAE or camptothecin.

36. An antibody-drug conjugate comprising an anti-PD-L1 antibody conjugated to a cytotoxic agent via a linker, wherein the antibody comprises the heavy chain variable region sequence of SEQ ID NO: 11 and the light chain variable region sequence of SEQ ID NO: 12.

37. The antibody-drug conjugate of claim 36, wherein the cytotoxic agent is MMAE.

38. A composition comprising the antibody-drug conjugate of claim 36.

39. The antibody-drug conjugate of claim 36, wherein the antibody comprises the heavy chain sequence of SEQ ID NO: 9 and the light chain sequence of SEQ ID NO: 10.

40. The antibody-drug conjugate of claim 39, wherein the cytotoxic agent is MMAE.

41. A composition comprising the antibody-drug conjugate of claim 39.

42. An antibody-drug conjugate comprising an anti-PD-L1 antibody conjugated to vcMMAE, wherein the antibody comprises the heavy chain variable region sequence of SEQ ID NO: 11 and the light chain variable region sequence of SEQ ID NO: 12, and wherein the antibody-drug conjugate has the structure:

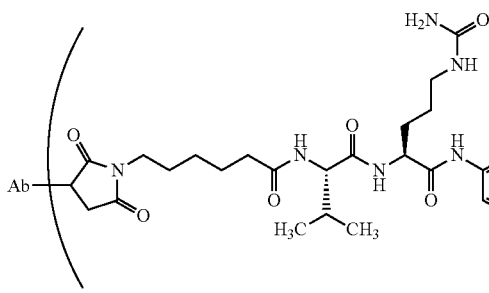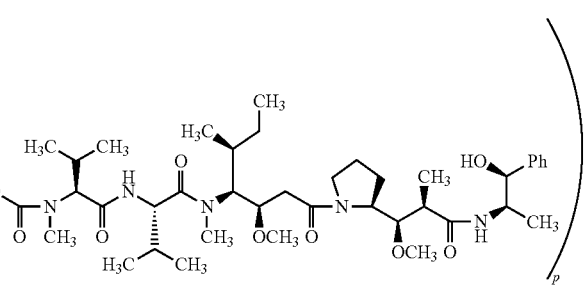

wherein Ab represents the antibody and p ranges from 2 to 10.

43. The antibody-drug conjugate of claim 42, wherein p is 4.

44. An antibody-drug conjugate comprising an anti-PD-L1 antibody conjugated to vcMMAE, wherein the antibody comprises the heavy chain sequence of SEQ ID NO: 9 and the light chain sequence of SEQ ID NO: 10, and wherein the antibody-drug conjugate has the structure:

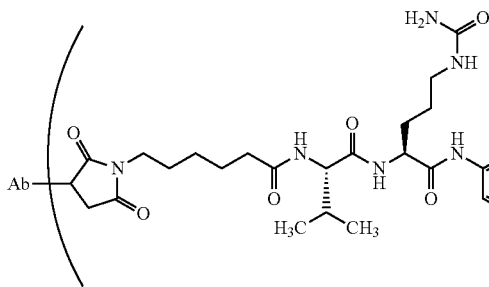

wherein Ab represents the antibody and p ranges from 2 to 10.

45. The antibody-drug conjugate of claim 44, wherein p is 4.

46. A method of treating cancer in a subject, comprising administering to the subject the antibody of claim 12.

47. A method of treating cancer in a subject, comprising administering to the subject an antibody-drug conjugate comprising an anti-PD-L1 antibody conjugated to vcMMAE, wherein the antibody comprises the heavy chain variable region sequence of SEQ ID NO: 11 and the light chain variable region sequence of SEQ ID NO: 12, and wherein the antibody-drug conjugate has the structure:

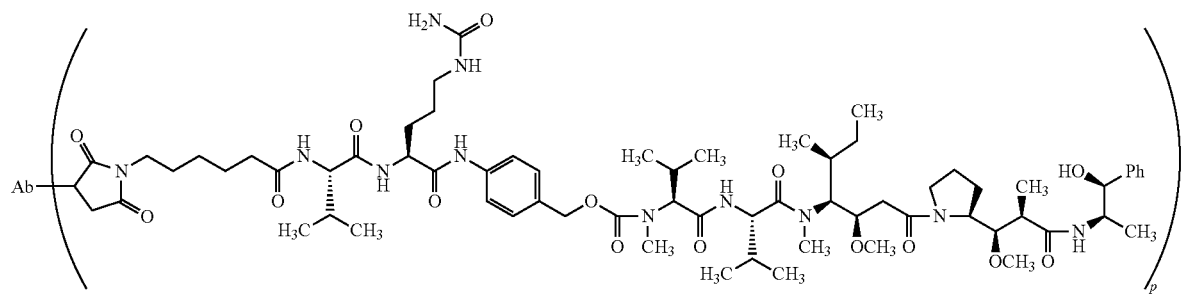

wherein Ab represents the antibody and p ranges from 2 to 10.

48. The method of claim 47, wherein p is 4.

49. The method of claim 47, wherein the antibody comprises the heavy chain sequence of SEQ ID NO: 9 and the light chain sequence of SEQ ID NO: 10.

50. An antibody that specifically binds to the human PD-L1 protein, wherein the antibody comprises the heavy chain variable region sequence of SEQ ID NO: 11 and the light chain variable region sequence of SEQ ID NO: 12.

51. An antibody that specifically binds to the human PD-L1 protein, wherein the antibody comprises the heavy chain sequence of SEQ ID NO: 9 and the light chain sequence of SEQ ID NO: 10.

* * * * *